US009205148B2

(12) United States Patent
Langermann et al.

(10) Patent No.: US 9,205,148 B2
(45) Date of Patent: Dec. 8, 2015

(54) ANTIBODIES AND OTHER MOLECULES THAT BIND B7-H1 AND PD-1

(75) Inventors: Solomon Langermann, Baltimore, MD (US); Linda Liu, Clarksville, MD (US); Shannon Marshall, Baltimore, MD (US); Sheng Yao, Columbia, MD (US)

(73) Assignee: MedImmune, LLC, Gaithersburg, MD (US)

( * ) Notice: Subject to any disclaimer, the term of this patent is extended or adjusted under 35 U.S.C. 154(b) by 117 days.

(21) Appl. No.: 14/111,402

(22) PCT Filed: Apr. 19, 2012

(86) PCT No.: PCT/US2012/034223
§ 371 (c)(1),
(2), (4) Date: Oct. 11, 2013

(87) PCT Pub. No.: WO2012/145493
PCT Pub. Date: Oct. 26, 2012

(65) Prior Publication Data
US 2014/0044738 A1    Feb. 13, 2014

Related U.S. Application Data

(60) Provisional application No. 61/477,414, filed on Apr. 20, 2011.

(51) Int. Cl.
C07K 16/28    (2006.01)
A61K 39/395    (2006.01)
G01N 33/68    (2006.01)

(52) U.S. Cl.
CPC ............ *A61K 39/3955* (2013.01); *C07K 16/28* (2013.01); *C07K 16/2818* (2013.01); *C07K 16/2827* (2013.01); *G01N 33/6854* (2013.01); *C07K 2317/24* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,413,923 A | 5/1995 | Kucherlapati | |
| 5,545,806 A | 8/1996 | Lonberg | |
| 5,569,825 A | 10/1996 | Lonberg | |
| 5,625,126 A | 4/1997 | Lonberg | |
| 5,633,425 A | 5/1997 | Lonberg | |
| 5,661,016 A | 8/1997 | Lonberg | |
| 5,814,318 A | 9/1998 | Lonberg | |
| 5,939,598 A | 8/1999 | Kucherlapati | |
| 6,005,079 A | 12/1999 | Casterman | |
| 6,803,192 B1 | 10/2004 | Chen | |
| 6,808,710 B1 | 10/2004 | Wood | |
| 7,029,674 B2 | 4/2006 | Carreno | |
| 7,101,550 B2 * | 9/2006 | Wood et al. | 424/144.1 |
| 7,488,802 B2 * | 2/2009 | Collins et al. | 530/387.1 |
| 7,521,051 B2 | 4/2009 | Collins | |
| 7,563,869 B2 | 7/2009 | Honjo | |
| 7,595,048 B2 | 9/2009 | Honjo | |
| 7,635,757 B2 | 12/2009 | Freeman | |
| 7,722,868 B2 | 5/2010 | Freeman | |
| 7,794,710 B2 | 9/2010 | Chen | |
| 2004/0241745 A1 | 12/2004 | Honjo | |
| 2005/0037000 A1 | 2/2005 | Stavenhagen | |
| 2005/0059051 A1 | 3/2005 | Chen | |
| 2007/0122378 A1 | 5/2007 | Freeman | |
| 2007/0202100 A1 | 8/2007 | Wood | |
| 2008/0311117 A1 | 12/2008 | Collins | |
| 2009/0055944 A1 | 2/2009 | Korman | |
| 2009/0076250 A1 | 3/2009 | Honjo | |
| 2009/0110667 A1 | 4/2009 | Mozaffarian | |
| 2009/0217401 A1 | 8/2009 | Korman | |
| 2009/0263865 A1 | 10/2009 | Honjo | |
| 2009/0274666 A1 | 11/2009 | Chen | |
| 2009/0297518 A1 | 12/2009 | Honjo | |
| 2009/0313687 A1 | 12/2009 | Popp | |
| 2009/0317368 A1 | 12/2009 | Chen | |
| 2010/0028330 A1 | 2/2010 | Collins | |
| 2010/0040614 A1 | 2/2010 | Ahmed | |

FOREIGN PATENT DOCUMENTS

| | | |
|---|---|---|
| CN | 101213297 | 7/2008 |
| WO | 9404678 | 3/1994 |
| WO | 9425591 | 11/1994 |
| WO | 9633735 | 10/1996 |
| WO | 9634096 | 10/1996 |
| WO | 9824893 | 6/1998 |
| WO | 0114557 | 3/2001 |
| WO | 0139722 | 6/2001 |

(Continued)

OTHER PUBLICATIONS

Agarwal, et al., "The Role Of Positive Costimulatory Molecules In Transplantation And Tolerance," Curr. Opin. Organ Transplant. 13:366-72 (2008).
Agata, et al., "Expression Of The PD-1 Antigen On The Surface Of Stimulated Mouse T And B Lymphocytes," Int. Immunol., 8(5):765-72 (1996).
Al-Laziniki, et al., "Standard Conformations For The Canonical Structures Of Immunoglobulins," J. Molec. Biol., 273:927-948 (1997).
Barber, et al., "CD4 T Cells Promote Rather than Control Tuberculosis in the Absence of PD-I-Mediated Inhibition," J. Immunol., 186:1598-1607 (2011).
Bebbington, et al., "High-Level Expression Of A Recombinant Antibody From Myeloma Cells Using A Glutamine Synthetase Gene As An Amplifiable Selectable Marker," Biotechnology, 10(2):169-75 (1992).
Blank, et al., "Contribution Of The PD-L1/PD-1 Pathway To T-Cell Exhaustion: An Update On Implications For Chronic Infections And Tumor Evasion Cancer," Immunol. Immunother. 56(5):739-45 (2007).

(Continued)

*Primary Examiner* — Ilia Ouspenski
(74) *Attorney, Agent, or Firm* — Pabst Patent Group LLP

(57) ABSTRACT

The present invention relates to antibodies and their antigen-binding fragments and to other molecules that are capable of immunospecifically binding to B7-H1 or PD-1. In some embodiments such molecules are additionally capable of modulating the ability of B7-H1 or B7-DC to bind to PD-1 or are capable of affecting the signaling activity of the B7-H1 or PD-1. The invention additionally concerns the uses of such molecules in the diagnosis and treatment of cancer and other diseases.

22 Claims, 19 Drawing Sheets

(56) References Cited

FOREIGN PATENT DOCUMENTS

| WO | 02086083 | 10/2002 |
|---|---|---|
| WO | 2004056875 | 7/2004 |
| WO | 2006121168 | 11/2006 |
| WO | 2006133396 | 12/2006 |
| WO | 2008083174 | 7/2008 |
| WO | 2010029434 | 3/2010 |
| WO | 2010036959 | 4/2010 |
| WO | 2011110621 | 9/2011 |

OTHER PUBLICATIONS

Brahmer, et al., "Phase II experience with MDX-1106 (ono-4538), an anti-PD-1 monoclonal antibody, in patients with selected refractory or relapsed malignancies", ASCO Meeting Abstracts, J Clin Oncology, 27(15S) (2009).
Brown, et al., "Blockade Of Programmed Death-1 Ligands On Dendritic Cells Enhances T Cell Activation And Cytokine Production," J. Immunol. 170:1257-66 (2003).
Butte, et al., "Interaction of PD-LI and B7-\," Molecular Immunol. 45:3567-3572 (2008).
Carter, et al., "Cell Biology Of HIV-1 Infection Of Macrophages," Ann. Rev. Microbiol. 62:425-43 (2008).
Carter, et al., "PD-I.PD-L inhibitory pathway affects both CD4(+) and CD8(+) T cells and is overcome by IL-2," Eur. J. Immunol. 32(3):634-43 (2002).
Chen, et al., "Expression Of B7-H1 In Inflammatory Renal Tubular Epithelial Cells," Nephron. Exp. Nephrol., 102(3-4):e81-e92 (2005).
Chothia, et al., "Canonical Structures For The Hypervariable Regions Of Immunoglobulins," J. Mol. Biol., 196:901-17 (1987).
Chothia, et al., "Structural determinants in the sequences of immunoglobulin variable domain", J. Mol. Biol., 278: 457-79 1998.
Collins, et al., "The B7 Family Of Immune-regulatory Ligands," Genome Biol., 6(6):223(2005).
Coyle, et al., "The Expanding B7 Superfamily: Increasing Complexity In Costimulatory Signals Regulating T Cell Function," Nature Immunol., 2(3):203-9 (2001).
de Haij, et al., "Renal Tubular Epithelial Cells Modulate T- Cell Responses Via ICOS-L And B7-H1", Kidney Int. 68:2091-2102 (2005).
De Keersmaecker, et al., "Fighting with the Enemy's Weapons? The Role of Costimulatory Molecules in HIV," Curr. Molec. Med., 566-5240/11:1-25 (2011).
Dong, "B7-H1 Pathway And Its Role In The Evasion Of Tumor Immunity," J. Mol. Med. 81:281-7 (2003b).
Dong, et al., "Immune Regulation by Novel Costimulatory Molecules," Immunolog. Res. 28(I):39-48 (2003a).
Dong, et al., "Tumor-Associated B7-H1 Promotes T-Cell Apoptosis: A Potential Mechanism Of Immune Evasion," Nature Med. 8(8):793-800 (2002).
Dorfman, et al., "Programmed Death-1 (PD-1) Is A Marker Of Germinal Center-Associated T Cells And Angioimmunoblastic T-Cell Lymphoma," Am. J. Surg. Pathol. 30(7):802-10 (2006).
Eichbaum, "PD-1 Signaling In HIV And Chronic Viral Infection Potential For Therapeutic Intervention?" Curr. Med. Chem., 18(26):3971-80 (2011).
Elloso, et al., "Expression and Contribution of B7-1 (CD80) and B7-2 (CD86) in the Early Immune Response to Leishmania major Infection," J. Immunol., 162:6708-15 (1999).
Flajnik, et al., "Evolution Of The B7 Family: Co-Evolution Of B7H6 And Nkp30, Identification Of A New B7 Family Member, B7H7, And Of B7's Historical Relationship With The MHC," Immunogenetics, 64(8):571-90 (2012).
Flies, et al., "The New B7s: Playing a Pivotal Role in Tumor Immunity," J. Immunother. 30(3):251-60 (2007).
Foote, et al., "Antibody Framework Residues Affecting The Conformation Of The Hypervariable Loops," J. Molec. Biol., 224:487-99 (1992).
Freeman, et al., "Engagement Of The PD-1 Immunoinhibitory Receptor By A Novel B7 Family Member Leads To Negative Regulation Of Lymphocyte Activation," J. Exp. Med., 192:1-9 (2000).

Grabmeier-Pfistershammer, et al., "Identification of PD-1 as a Unique Marker for Failing Immune Reconstitution in HIV-1-Infected Patients on Treatment," J Acquir. Immune Defic. Syndr., 56(2): 118-24 (2011).
Greenwald, et al., "The B7 Family Revisited," Ann. Rev. Immunol., 23:515-48 (2005).
Gross, et al., "Identification And Distribution Of The Costimulatory Receptor CD28 In The Mouse," J. Immunol., 149:380-8 (1992).
Hallett, et al., "Immunosuppressive Effects Of Multiple Myeloma Are Overcome By PD-L1 Blockade," Biol Blood Marrow Transplant., 17(8):1133-45 (2011).
Hirano, et al., "Blockade of B7-H1 and PD1 by monoclonal antibodies potentiates cancer therapeutic immunity" . Cancer Res., 65(3):1089-96 (2005).
Honegger, et al., "Yet Another Numbering Scheme For Immunoglobulin Variable Domains: An Automatic Modeling And Analysis Tool," J. Molec. Biol., 309(3):657-70 (2001).
Inozume, et al., "Selection Of CD8+PD-1+ Lymphocytes In Fresh Human Melanomas Enriches For Tumor-Reactive T Cells," J. Immunother., 33(9):956-64 (2010).
Ishida, et al., "Induced Expression Of PD-1, A Novel Member Of The Immunoglobulin Gene Superfamily, Upon Programmed Cell Death," EMBO J., 11:3887-95 (1992).
Ishiwata, et al., "Costimulator Responses Induced by Nippostrongylus brasiliensis," J. Immunol., 184:2086-94 (2010).
Jin, et al. "Cooperation Of Tim-3 And PD-1 In CD8 T-Cell Exhaustion During Chronic Viral Infection," PNAS, 107(33):14733-8 (2010).
Katoh, et al., "MAFFT: A Novel Method For Rapid Multiple Sequence Alignment Based On Fast Fourier Transform," Nucleic Acids Res., 30:3059-66 (2002).
Khaitan, et al., "Revisiting Immune Exhaustion During HIV Infection," Curr. HIV/AIDS Rep., 8:4-11 (2011).
Killian, et al., "Natural Suppression of Human Immunodeficiency Virus Type 1 Replication Is Mediated by Memory CD8+ T Cells," J. Virol., 85(4):1696-1705 (2011).
Korman, et al., "Checkpoint Blockade in Cancer Immunotherapy," Adv. Immunol., 90:297-339 (2007).
Latchman, et al., "PD-L2 Is A Second Ligand For PD-1 And Inhibits T Cell Activation," Nat. Immunol., 2:261-8 (2001).
Lazar-Molnar, et al., "Crystal Structure Of The Complex Between Programmed Death-1 (PD-1) And Its Ligand PD-L2," PNAS, 105(30): 10483-8 (2008).
Lazar-Molnar, et al., "Programmed Death-1 (PD-I)-Deficient Mice Are Extraordinarily Sensitive To Tuberculosis," PNAS, 107(30):13402-7 (2010).
Lenschow, et al., "CD28/B7 System of T Cell Costimulation," Ann. Rev. Immunol., 14:233-58 (1996).
Lepenies, et al., "The Role Of Negative Costimulators During Parasitic Infections," Endocr Metab Immune Disord Drug Targets, 8:279-88 (2008).
Lindley, et al., "The Clinical Utility Of Inhibiting CD28-Mediated Costimulation," Immunol. Rev., 229:307-21 (2009).
Linsley, et al., "Intracellular Trafficking Of CTLA4 And Focal Localization Towards Sites Of TCR Engagement," Immunity, 4:535-43 (1996).
Loke, et al., "Emerging Mechanisms Of Immune Regulation: The Extended B7 Family And Regulatory T Cells." Arthritis Res. Ther., 6:208-14 (2004).
Lonberg and Huszar, "Human antibodies from transgenic mice", Int. Rev. Immunol., 13:65-93 (1995).
Marchler-Bauer, et al., "COD: A Conserved Domain Database For The Functional Annotation Of Proteins," Nucleic Acids Res., 39:D225-9 (2011).
Martin, et al., "Structural Families In Loops Of Homologous Proteins: Automatic Classification, Modelling And Application To Antibodies," J. Molec. Biol., 263:800-15 (1996).
Martin-Orozco, et al., "Inhibitory Costimulation And Anti-Tumor Immunity," Semin. Cancer Biol., 17(4):288-98 (2007).
Mazanet, et al., "B7-H1 Is Expressed By Human Endothelial Cells And Suppresses T Cell Cytokine Synthesis," J. Immunol., 169:3581-8 (2002).

(56) References Cited

OTHER PUBLICATIONS

Muyldermans, et al., "Recognition of antigens by single-domain antibody fragments: the superfluous luxury of paired domains", Trends Biochem. Sci., 26:230-5 (2001).
Ni, et al., "PD-1 Modulates Regulatory T Cells And Suppresses T-Cell Responses In HCV-Associated Lymphoma," Immunol. Cell. Biol., 89(4):535-9 (2010).
Nishimura, et al., "Facilitation Of Beta Selection And Modification Of Positive Selection In The Thymus Of PD-1-Deficient Mice," J. Exp. Med., 191:891-8 (2000).
Noursadeghi, et al., "HIV-1 Infection Of Mononuclear Phagocytic Cells: The Case For Bacterial Innate Immune Deficiency In AIDS," Lancet Infect. Dis., 6:794-804 (2006).
Nuttall, et al., "Immunoglobulin VH domains and beyond: design and selection of single-domain binding and targeting reagents", Cur. Pharm. Biotech., 1:253-63 (2000).
Petroff, et al., "B7 Family Molecules: Novel Immunomodulators At The Maternal-Fetal Interface," Placenta, 23:S95-S101 (2002).
Reichmann and Muyldermans, "Single domain antibodies: comparison of camel VH and camelised human VH domains", J. Immunol. Meth., 231:25-38 (1999).
Rodriquez-Garcia, et al., "Expression Of PD-LI And PD-L2 On Human Macrophages Is Up-Regulated By HIV-1 And Differentially Modulated by IL-10," J. Leukocyte Biol., 89(4):507-15 (2010).
Sakai, et al., "PD-1-PD-L1 pathway impairs Th1 immune response in the late stage of infection with Mycobacterium bovis bacillus Calmette-Guerin," Intl. Immunol. 22(12):915-25 (2010).
Sali, et al., "Comparative Protein Modelling by Satisfaction Of Spatial Restraints," J. Molec. Biol., 234:779-815 (1993).
Sarikonda, "Immunosuppressive Mechanisms During Viral Infectious Diseases;" Methods in Molec. Biol., 677:431-47 (2011).
Sharpe, et al., "The B7-CD28 Superfamily," Nature Rev. Immunol., 2:116-26 (2002).
Spahn, et al.,"Ineffective CD8(+) T-Cell Immunity to Adeno-Associated Virus Can Result In Prolonged Liver Injury And Fibrogenesis," Amer. J. Pathol., 179 (5):2370-81 (2011).
Subudhi, et al., "The Balance Of Immune Responses: Costimulation Verse Coinhibition," J. Molec. Med., 83:193-202 (2005).
Thompson, et al., "Tumor B7-H1 is associated with poor prognosis in renal cell carcinoma patients with long-term follow-up", Cancer Res., 66(7):3381-5 (2006).
Titanji, et al., "Acute Depletion Of Activated Memory B Cells Involves The PD-1 Pathway In Rapidly Progressing SIV-Infected Macaques," J. Clin. Invest., 120 (11):3878-90 (2010).
Viglietta, et al., "Modulating Co-Stimulation," Neurotherapeutics, 4:666-75 (2007).
Wang, et al., "Phenotype, Effector Function, And Tissue Localization of PD-1-Expressing Human Follicular Helper T Cell Subsets," BMC Immunol., 12:53, 1-15 (2011a).
Wang, et al., "Co-Signaling Molecules Of The B7-CD28 Family In Positive And Negative Regulation Of T Lymphocyte Responses," Microbes Infect., 6:759-66 (2004).
Wang, et al., "VISTA, A Novel Mouse Ig Superfamily Ligand That Negatively Regulates T Cell Responses," J. Exp. Med., 208(3):577-92 (2011b).
Wu, et al., "Kupjfer Cell Suppression of CD8+ T Cells in Human Hepatocellular Carcinoma Is Mediated by B7-HI/Programmed Death-1 Interactions," Cancer Res., 69(20):8067-75 (2009).
Xu, et al., "Increased B7-H1 Expression on Dendritic Cells Correlates with Programmed Death 1 Expression on T Cells in Simian Immunodeficiency Virus-Infected Macaques and May Contribute to T Cell Dysfunction and Disease Progression," J. Immunol., 185:7340-8 (2010).
Yamazaki, et al., "Expression of Programmed Death 1 Ligands by Murine T Cells and APC," J. Immunol., 169:5538-45 (2002).
Youngblood, "Chronic Virus Infection Enforces Demethylation of the Locus That Encodes PD-1 in Antigen-Specific CD8(+) T Cells," Immunity, 35(3):400-12 (2011).

\* cited by examiner

CHO hPD-1 transfectants h1H3 Var 5 h1H3 Var 6 h1H3 Var 7 h1H3 Var 8

10ng Abs+ a-hIg PE

SEQUENCE LISTING

<160> NUMBER OF SEQ ID NOS: 109

<210> SEQ ID NO 1
<211> LENGTH: 107
<212> TYPE: PRT
<213> ORGANISM: Mus musculus

```
<400> SEQUENCE: 1

Asp Ile Val Met Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Asp Ser Ser Tyr Pro Leu
                85                  90                  95

Thr Phe Gly Ala Gly Thr Lys Val Glu Leu Lys
            100                 105

<210> SEQ ID NO 2
<211> LENGTH: 118
<212> TYPE: PRT
<213> ORGANISM: Mus musculus

<400> SEQUENCE: 2

Glu Val Lys Leu Gln Glu Ser Gly Pro Ser Leu Val Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Val
        35                  40                  45

Gly Tyr Ile Ser Tyr Thr Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Ser Glu Asp Thr Ala Thr Tyr Tyr Cys Ala
                85                  90                  95

Arg Tyr Gly Gly Trp Leu Ser Pro Phe Asp Tyr Trp Gln Gly Thr
            100                 105                 110

Thr Leu Thr Val Ser Ser
        115

<210> SEQ ID NO 3
<211> LENGTH: 107
<212> TYPE: PRT
<213> ORGANISM: Mus musculus

<400> SEQUENCE: 3

Asp Ile Val Thr Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Asp Ser Ser Tyr Pro Leu
```

```
            85                  90                  95
Thr Phe Gly Ala Gly Thr Lys Val Glu Leu Lys
                100                 105

<210> SEQ ID NO 4
<211> LENGTH: 120
<212> TYPE: PRT
<213> ORGANISM: Mus musculus

<400> SEQUENCE: 4

Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Ser Ile Asn Trp Ile Arg Gln Pro Pro Gly Lys Gly Leu Glu Trp Leu
        35                  40                  45

Gly Val Met Trp Ala Gly Gly Thr Asn Ser Asn Ser Val Leu Lys
    50                  55                  60

Ser Arg Leu Ile Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Tyr Tyr Gly Asn Ser Pro Tyr Tyr Ala Ile Asp Tyr Trp Gly Gln
                100                 105                 110

Gly Thr Ser Val Thr Val Ser Ser
            115                 120

<210> SEQ ID NO 5
<211> LENGTH: 113
<212> TYPE: PRT
<213> ORGANISM: Mus musculus

<400> SEQUENCE: 5

Asp Ile Val Met Thr Gln Ser Pro Ser Ser Leu Ala Val Ser Val Gly
1               5                   10                  15

Glu Lys Val Ser Met Gly Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Asp Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
                100                 105                 110

Lys

<210> SEQ ID NO 6
<211> LENGTH: 118
<212> TYPE: PRT
<213> ORGANISM: Mus musculus

<400> SEQUENCE: 6

Glu Val Lys Leu Gln Glu Ser Gly Pro Ser Leu Val Lys Pro Ser Gln
1               5                   10                  15
```

```
Thr Leu Ser Leu Thr Cys Ser Val Thr Gly Tyr Ser Ile Ile Ser Asp
            20                  25                  30

Tyr Trp Asn Trp Ile Arg Lys Phe Pro Gly Asn Lys Leu Glu Tyr Leu
        35                  40                  45

Gly Tyr Ile Ser Tyr Thr Gly Ser Thr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Arg Gly Gly Trp Leu Leu Pro Phe Asp Tyr Trp Gly Gln Gly Thr
            100                 105                 110

Thr Leu Thr Val Ser Ser
            115
```

<210> SEQ ID NO 7
<211> LENGTH: 106
<212> TYPE: PRT
<213> ORGANISM: Mus musculus

<400> SEQUENCE: 7

```
Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Ile Arg Tyr Met
            20                  25                  30

His Trp Tyr Gln Gln Lys Pro Gly Thr Ser Pro Lys Arg Trp Ile Ser
        35                  40                  45

Asp Thr Ser Lys Leu Thr Ser Gly Val Pro Ala Arg Phe Ser Gly Ser
    50                  55                  60

Gly Ser Gly Thr Ser Tyr Ala Leu Thr Ile Ser Ser Met Glu Ala Glu
65                  70                  75                  80

Asp Ala Ala Thr Tyr Tyr Cys His Gln Arg Ser Ser Tyr Pro Trp Thr
                85                  90                  95

Phe Gly Gly Gly Thr Lys Leu Glu Ile Lys
            100                 105
```

<210> SEQ ID NO 8
<211> LENGTH: 118
<212> TYPE: PRT
<213> ORGANISM: Mus musculus

<400> SEQUENCE: 8

```
Glu Val Lys Leu Gln Glu Ser Gly Pro Ser Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Phe Pro Arg Asp Asn Asn Thr Lys Tyr Asn Glu Asn Phe
    50                  55                  60

Lys Gly Lys Ala Thr Leu Thr Val Asp Thr Ser Ser Thr Thr Ala Tyr
65                  70                  75                  80

Met Glu Leu His Ser Leu Thr Ser Glu Asp Ser Ala Val Tyr Phe Cys
                85                  90                  95

Thr Lys Glu Asn Trp Val Gly Asp Phe Asp Tyr Trp Gly Gln Gly Thr
            100                 105                 110
```

```
Thr Leu Thr Leu Ser Ser
            115

<210> SEQ ID NO 9
<211> LENGTH: 106
<212> TYPE: PRT
<213> ORGANISM: Mus musculus

<400> SEQUENCE: 9

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

Tyr Trp Phe Gln Gln Lys Pro Gly Ser Ser Pro Lys Pro Trp Ile Tyr
        35                  40                  45

Ala Thr Phe Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Thr Glu
65                  70                  75                  80

Asp Ala Ala Thr Tyr Tyr Cys Gln Gln Trp Ser Asn Asn Pro Leu Thr
                85                  90                  95

Phe Gly Ala Gly Thr Lys Leu Glu Leu Lys
            100                 105

<210> SEQ ID NO 10
<211> LENGTH: 114
<212> TYPE: PRT
<213> ORGANISM: Mus musculus

<400> SEQUENCE: 10

Glu Val Gln Leu Gln Gln Ser Gly Pro Asp Leu Val Thr Pro Gly Ala
1               5                   10                  15

Ser Val Arg Ile Ser Cys Gln Ala Ser Gly Tyr Thr Phe Pro Asp Tyr
            20                  25                  30

Tyr Met Asn Trp Val Lys Gln Ser His Gly Lys Ser Leu Glu Trp Ile
        35                  40                  45

Gly Asp Ile Asp Pro Asn Tyr Gly Gly Thr Thr Tyr Asn Gln Lys Phe
    50                  55                  60

Lys Gly Lys Ala Ile Leu Thr Val Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ala Leu Thr Asp Trp Gly Gln Gly Thr Ser Leu Thr Val
            100                 105                 110

Ser Ser

<210> SEQ ID NO 11
<211> LENGTH: 106
<212> TYPE: PRT
<213> ORGANISM: Mus musculus

<400> SEQUENCE: 11

Asp Ile Gln Met Thr Gln Phe Pro Ser Ser Leu Cys Ala Ser Gln Gly
1               5                   10                  15

Gly Lys Val Thr Val Thr Cys Lys Ala Ser Gln Asp Ile Asn Asn Tyr
            20                  25                  30

Met Ala Trp Tyr Gln His Lys Pro Gly Lys Gly Pro Arg Leu Leu Ile
        35                  40                  45
```

```
His Tyr Thr Ser Thr Leu Leu Ser Gly Ile Pro Ser Arg Phe Ser Gly
            50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Trp Thr
                 85                  90                  95

Phe Gly Gly Gly Thr Lys Leu Glu Ile Lys
            100                 105
```

<210> SEQ ID NO 12
<211> LENGTH: 119
<212> TYPE: PRT
<213> ORGANISM: Mus musculus

<400> SEQUENCE: 12

```
Glu Val Gln Leu Gln Gln Ser Gly Pro Val Leu Val Lys Pro Gly Ala
 1               5                  10                  15

Ser Val Lys Met Ser Cys Lys Ala Ser Gly Tyr Thr Phe Thr Asp Tyr
                 20                  25                  30

Tyr Met Asn Trp Val Lys Gln Ser His Gly Lys Ser Leu Glu Trp Ile
             35                  40                  45

Gly Asn Ile Asn Pro Tyr Asn Gly Gly Thr Thr Tyr Asn Gln Lys Phe
 50                  55                  60

Lys Gly Lys Ala Thr Leu Thr Val Asp Lys Ser Ser Arg Thr Ala Tyr
 65                  70                  75                  80

Met Glu Ile Asn Ser Leu Thr Ser Glu Asp Ser Ala Val Tyr Tyr Cys
                 85                  90                  95

Ala Arg Gly Arg Ile Tyr Asp Gly Ser Leu Asp Tyr Trp Gly Gln Gly
            100                 105                 110

Thr Ala Leu Thr Val Ser Ser
        115
```

<210> SEQ ID NO 13
<211> LENGTH: 107
<212> TYPE: PRT
<213> ORGANISM: Mus musculus

<400> SEQUENCE: 13

```
Asp Ile Val Met Thr Gln Ser Gln Lys Phe Met Ser Thr Ser Val Gly
 1               5                  10                  15

Asp Arg Val Ser Val Thr Cys Lys Ala Ser Gln Ser Val Asp Thr Asn
                 20                  25                  30

Val Ala Trp Tyr Gln Gln Lys Pro Gly Gln Ser Pro Lys Ala Leu Ile
             35                  40                  45

Phe Ser Ala Ser Tyr Arg Tyr Ser Gly Val Pro Asp Arg Phe Thr Gly
             50                  55                  60

Ser Gly Ser Gly Thr Asp Phe Thr Leu Thr Ile Asn Ser Val Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Ser Gly Thr Lys Leu Glu Ile Lys
            100                 105
```

<210> SEQ ID NO 14
<211> LENGTH: 116
<212> TYPE: PRT
<213> ORGANISM: Mus musculus

<400> SEQUENCE: 14

```
Gln Val Gln Leu Gln Gln Ser Gly Ala Glu Leu Ala Lys Pro Gly Ala
1               5                   10                  15
Ser Val Arg Leu Ser Cys Lys Ala Ser Gly Tyr Thr Phe Thr Asn Tyr
            20                  25                  30
Trp Met His Trp Val Lys Gln Arg Pro Gly Gln Gly Leu Glu Trp Ile
        35                  40                  45
Gly His Ile Asn Pro Ser Ser Gly Phe Thr Thr Tyr Asn Gln Asn Phe
    50                  55                  60
Lys Asp Lys Ala Thr Leu Thr Ala Asp Lys Ser Ser Asn Thr Ala Tyr
65                  70                  75                  80
Met Gln Leu Ser Ser Leu Thr Tyr Glu Asp Ser Ala Val Tyr Phe Cys
                85                  90                  95
Ala Arg Glu Asp Tyr Asp Val Asp Tyr Trp Gly Gln Gly Thr Thr Leu
            100                 105                 110
Thr Val Ser Ser
        115
```

<210> SEQ ID NO 15
<211> LENGTH: 106
<212> TYPE: PRT
<213> ORGANISM: Mus musculus

<400> SEQUENCE: 15

```
Gln Ile Val Leu Thr Gln Ser Pro Ala Leu Met Ser Ala Ser Pro Gly
1               5                   10                  15
Glu Lys Val Thr Met Thr Cys Ser Ala Ser Ser Ser Val Ser Tyr Met
            20                  25                  30
Tyr Trp Tyr Gln Gln Lys Pro Arg Ser Ser Pro Lys Pro Trp Ile Tyr
        35                  40                  45
Leu Thr Ser Asn Leu Ala Ser Gly Val Pro Ala Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Ser Asn Pro Phe Thr
                85                  90                  95
Phe Gly Ser Gly Thr Lys Leu Glu Ile Lys
            100                 105
```

<210> SEQ ID NO 16
<211> LENGTH: 122
<212> TYPE: PRT
<213> ORGANISM: Mus musculus

<400> SEQUENCE: 16

```
Glu Val Gln Leu Val Glu Ser Gly Gly Gly Leu Val Lys Pro Gly Gly
1               5                   10                  15
Ser Leu Lys Leu Ser Cys Ala Ala Ser Gly Phe Thr Phe Ser Asp Tyr
            20                  25                  30
Gly Met His Trp Val Arg Gln Ala Pro Glu Lys Gly Leu Glu Trp Val
        35                  40                  45
Ala Tyr Ile Ser Ser Gly Ser Tyr Thr Ile Tyr Tyr Thr Asp Thr Val
    50                  55                  60
Lys Gly Arg Phe Thr Ile Ser Arg Asp Asn Ala Lys Asn Thr Leu Phe
65                  70                  75                  80
```

-continued

Leu Gln Met Thr Ser Leu Arg Ser Glu Asp Thr Ala Met Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
        115                 120

<210> SEQ ID NO 17
<211> LENGTH: 10
<212> TYPE: PRT
<213> ORGANISM: Mus musculus

<400> SEQUENCE: 17

Arg Ala Ser Ser Ser Val Ser Tyr Ile Tyr
1               5                   10

<210> SEQ ID NO 18
<211> LENGTH: 10
<212> TYPE: PRT
<213> ORGANISM: Mus musculus

<400> SEQUENCE: 18

Ser Ala Ser Ser Ser Ile Arg Tyr Met His
1               5                   10

<210> SEQ ID NO 19
<211> LENGTH: 11
<212> TYPE: PRT
<213> ORGANISM: Mus musculus

<400> SEQUENCE: 19

Lys Ala Ser Gln Asp Val Gly Thr Ala Val Ala
1               5                   10

<210> SEQ ID NO 20
<211> LENGTH: 17
<212> TYPE: PRT
<213> ORGANISM: Mus musculus

<400> SEQUENCE: 20

Lys Ser Ser Gln Ser Leu Leu Tyr Ser Ser Asn Gln Lys Asn Ser Leu
1               5                   10                  15

Ala

<210> SEQ ID NO 21
<211> LENGTH: 11
<212> TYPE: PRT
<213> ORGANISM: Mus musculus

<400> SEQUENCE: 21

Lys Ala Ser Gln Asp Val Gly Thr Ala Val Ala
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Anti-Human B7-H1 Light Chain CDR1 Consensus
      Sequence
<220> FEATURE:
<221> NAME/KEY: MISC_FEATURE
<222> LOCATION: (1)..(1)
<223> OTHER INFORMATION: R, S or K
<220> FEATURE:

```
<221> NAME/KEY: MISC_FEATURE
<222> LOCATION: (2)..(2)
<223> OTHER INFORMATION: A or S
<220> FEATURE:
<221> NAME/KEY: MISC_FEATURE
<222> LOCATION: (4)..(4)
<223> OTHER INFORMATION: R, N, D, Q, E, H, K, M, or S
<220> FEATURE:
<221> NAME/KEY: MISC_FEATURE
<222> LOCATION: (5)..(5)
<223> OTHER INFORMATION: SLLYSS or Absent
<220> FEATURE:
<221> NAME/KEY: MISC_FEATURE
<222> LOCATION: (6)..(6)
<223> OTHER INFORMATION: Absent or N or D
<220> FEATURE:
<221> NAME/KEY: MISC_FEATURE
<222> LOCATION: (7)..(7)
<223> OTHER INFORMATION: A, Q, E, L, K, M, P, S, T, Y, or V
<220> FEATURE:
<221> NAME/KEY: MISC_FEATURE
<222> LOCATION: (8)..(8)
<223> OTHER INFORMATION: Any Amino Acid
<220> FEATURE:
<221> NAME/KEY: MISC_FEATURE
<222> LOCATION: (9)..(9)
<223> OTHER INFORMATION: R, N, S, or T
<220> FEATURE:
<221> NAME/KEY: MISC_FEATURE
<222> LOCATION: (10)..(10)
<223> OTHER INFORMATION: A, R, N, C, Q, E, H, I, L, K, M, F, S, T, Y,
      or V
<220> FEATURE:
<221> NAME/KEY: MISC_FEATURE
<222> LOCATION: (11)..(11)
<223> OTHER INFORMATION: I, L, M, or V
<220> FEATURE:
<221> NAME/KEY: MISC_FEATURE
<222> LOCATION: (12)..(12)
<223> OTHER INFORMATION: A, R, N, Q, E, H, I, K, M, F, S, T, or Y

<400> SEQUENCE: 22

Xaa Xaa Ser Xaa Xaa Xaa Xaa Xaa Xaa Xaa Xaa Xaa
1               5                   10

<210> SEQ ID NO 23
<211> LENGTH: 6
<212> TYPE: PRT
<213> ORGANISM: Mus musculus

<400> SEQUENCE: 23

Ser Leu Leu Tyr Ser Ser
1               5

<210> SEQ ID NO 24
<211> LENGTH: 7
<212> TYPE: PRT
<213> ORGANISM: Mus musculus

<400> SEQUENCE: 24

Ala Thr Phe Asn Leu Ala Ser
1               5

<210> SEQ ID NO 25
<211> LENGTH: 7
<212> TYPE: PRT
<213> ORGANISM: Mus musculus

<400> SEQUENCE: 25

Asp Thr Ser Lys Leu Thr Ser
1               5
```

```
<210> SEQ ID NO 26
<211> LENGTH: 7
<212> TYPE: PRT
<213> ORGANISM: Mus musculus

<400> SEQUENCE: 26

Trp Ala Ser Thr Arg His Thr
1               5

<210> SEQ ID NO 27
<211> LENGTH: 7
<212> TYPE: PRT
<213> ORGANISM: Mus musculus

<400> SEQUENCE: 27

Trp Ala Ser Thr Arg Glu Ser
1               5

<210> SEQ ID NO 28
<211> LENGTH: 7
<212> TYPE: PRT
<213> ORGANISM: Mus musculus

<400> SEQUENCE: 28

Trp Ala Ser Thr Arg His Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Anti-Human B7-H1 Light Chain CDR2 Consensus
      Sequence
<220> FEATURE:
<221> NAME/KEY: MISC_FEATURE
<222> LOCATION: (1)..(1)
<223> OTHER INFORMATION: Any Amino Acid
<220> FEATURE:
<221> NAME/KEY: MISC_FEATURE
<222> LOCATION: (2)..(2)
<223> OTHER INFORMATION: A, C, G, S, T, or V
<220> FEATURE:
<221> NAME/KEY: MISC_FEATURE
<222> LOCATION: (3)..(3)
<223> OTHER INFORMATION: A, C, H, I, L, M, F, S, T, Y, or V
<220> FEATURE:
<221> NAME/KEY: MISC_FEATURE
<222> LOCATION: (4)..(4)
<223> OTHER INFORMATION: R, N, D, Q, E, K, S, or T
<220> FEATURE:
<221> NAME/KEY: MISC_FEATURE
<222> LOCATION: (5)..(5)
<223> OTHER INFORMATION: A, R, Q, L, K, M, S, T, or Y
<220> FEATURE:
<221> NAME/KEY: MISC_FEATURE
<222> LOCATION: (6)..(6)
<223> OTHER INFORMATION: A, R, N, D, Q, E, G, H, K, M, F, P, S, T, or Y
<220> FEATURE:
<221> NAME/KEY: MISC_FEATURE
<222> LOCATION: (7)..(7)
<223> OTHER INFORMATION: A, N, S, or T

<400> SEQUENCE: 29

Xaa Xaa Xaa Xaa Xaa Xaa Xaa
1               5

<210> SEQ ID NO 30
<211> LENGTH: 9
<212> TYPE: PRT
```

<213> ORGANISM: Mus musculus

<400> SEQUENCE: 30

Gln Gln Trp Ser Asn Asn Pro Leu Thr
1               5

<210> SEQ ID NO 31
<211> LENGTH: 9
<212> TYPE: PRT
<213> ORGANISM: Mus musculus

<400> SEQUENCE: 31

His Gln Arg Ser Ser Tyr Pro Trp Thr
1               5

<210> SEQ ID NO 32
<211> LENGTH: 9
<212> TYPE: PRT
<213> ORGANISM: Mus musculus

<400> SEQUENCE: 32

Gln Gln Asp Ser Ser Tyr Pro Leu Thr
1               5

<210> SEQ ID NO 33
<211> LENGTH: 9
<212> TYPE: PRT
<213> ORGANISM: Mus musculus

<400> SEQUENCE: 33

Gln Gln Tyr Tyr Gly Tyr Pro Leu Thr
1               5

<210> SEQ ID NO 34
<211> LENGTH: 9
<212> TYPE: PRT
<213> ORGANISM: Mus musculus

<400> SEQUENCE: 34

Gln Gln Asp Ser Ser Tyr Pro Leu Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Anti-Human B7-H1 Light Chain CDR3 Consensus
      Sequence
<220> FEATURE:
<221> NAME/KEY: MISC_FEATURE
<222> LOCATION: (1)..(1)
<223> OTHER INFORMATION: R, N, Q, E, or H
<220> FEATURE:
<221> NAME/KEY: MISC_FEATURE
<222> LOCATION: (3)..(3)
<223> OTHER INFORMATION: Any Amino Acid
<220> FEATURE:
<221> NAME/KEY: MISC_FEATURE
<222> LOCATION: (4)..(4)
<223> OTHER INFORMATION: A, R, N, C, Q, E, H, I, L, K, M, F, S, T, Y,
      or V
<220> FEATURE:
<221> NAME/KEY: MISC_FEATURE
<222> LOCATION: (5)..(5)
<223> OTHER INFORMATION: N, G or S
<220> FEATURE:
<221> NAME/KEY: MISC_FEATURE
<222> LOCATION: (6)..(6)

```
<223> OTHER INFORMATION: A, R, N, D, C, Q, E, G, H, I, L, K, M, F, P, S,
      T, W, Y, or V
<220> FEATURE:
<221> NAME/KEY: MISC_FEATURE
<222> LOCATION: (8)..(8)
<223> OTHER INFORMATION: A, R, N, D, Q, E, G, H, K, M, P, S, T, or Y

<400> SEQUENCE: 35

Xaa Gln Xaa Xaa Xaa Xaa Pro Xaa Thr
1               5

<210> SEQ ID NO 36
<211> LENGTH: 10
<212> TYPE: PRT
<213> ORGANISM: Mus musculus

<400> SEQUENCE: 36

Gly Tyr Thr Phe Pro Asp Tyr Tyr Met Asn
1               5                   10

<210> SEQ ID NO 37
<211> LENGTH: 10
<212> TYPE: PRT
<213> ORGANISM: Mus musculus

<400> SEQUENCE: 37

Gly Tyr Thr Phe Thr Ser Tyr Asp Ile Asn
1               5                   10

<210> SEQ ID NO 38
<211> LENGTH: 10
<212> TYPE: PRT
<213> ORGANISM: Mus musculus

<400> SEQUENCE: 38

Gly Tyr Ser Ile Thr Ser Asp Tyr Trp Asn
1               5                   10

<210> SEQ ID NO 39
<211> LENGTH: 10
<212> TYPE: PRT
<213> ORGANISM: Mus musculus

<400> SEQUENCE: 39

Gly Tyr Ser Ile Ile Ser Asp Tyr Trp Asn
1               5                   10

<210> SEQ ID NO 40
<211> LENGTH: 10
<212> TYPE: PRT
<213> ORGANISM: Mus musculus

<400> SEQUENCE: 40

Gly Phe Ser Leu Thr Thr Tyr Ser Ile Asn
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Anti-Human B7-H1 Heavy Chain CDR1 Consensus
      Sequence
<220> FEATURE:
<221> NAME/KEY: MISC_FEATURE
<222> LOCATION: (2)..(2)
<223> OTHER INFORMATION: Y or F
```

```
<220> FEATURE:
<221> NAME/KEY: MISC_FEATURE
<222> LOCATION: (3)..(3)
<223> OTHER INFORMATION: T or S
<220> FEATURE:
<221> NAME/KEY: MISC_FEATURE
<222> LOCATION: (4)..(4)
<223> OTHER INFORMATION: I, L, M, or F
<220> FEATURE:
<221> NAME/KEY: MISC_FEATURE
<222> LOCATION: (5)..(5)
<223> OTHER INFORMATION: A, R, N, D, C, Q, E, H, I, L, K, M, P, S, T, W,
      Y, or V
<220> FEATURE:
<221> NAME/KEY: MISC_FEATURE
<222> LOCATION: (6)..(6)
<223> OTHER INFORMATION: N, D, Q, E, K, P, S, or T
<220> FEATURE:
<221> NAME/KEY: MISC_FEATURE
<222> LOCATION: (7)..(7)
<223> OTHER INFORMATION: A, R, N, D, C, Q, E, G, H, I, L, K, M, F, P, S,
      T, Y, or V
<220> FEATURE:
<221> NAME/KEY: MISC_FEATURE
<222> LOCATION: (8)..(8)
<223> OTHER INFORMATION: A, R, N, D, C, Q, E, G, H, I, L, K, M, F, P, S,
      T, Y, or V
<220> FEATURE:
<221> NAME/KEY: MISC_FEATURE
<222> LOCATION: (9)..(9)
<223> OTHER INFORMATION: A, R, C, Q, E, H, I, L, K, M, F, S, T, W, Y,
      or V

<400> SEQUENCE: 41

Gly Xaa Xaa Xaa Xaa Xaa Xaa Xaa Asn
1               5

<210> SEQ ID NO 42
<211> LENGTH: 17
<212> TYPE: PRT
<213> ORGANISM: Mus musculus

<400> SEQUENCE: 42

Asp Ile Asp Pro Asn Tyr Gly Gly Thr Thr Tyr Asn Gln Lys Phe Lys
1               5                   10                  15

Gly

<210> SEQ ID NO 43
<211> LENGTH: 17
<212> TYPE: PRT
<213> ORGANISM: Mus musculus

<400> SEQUENCE: 43

Trp Ile Phe Pro Arg Asp Asn Asn Thr Lys Tyr Asn Glu Asn Phe Lys
1               5                   10                  15

Gly

<210> SEQ ID NO 44
<211> LENGTH: 16
<212> TYPE: PRT
<213> ORGANISM: Mus musculus

<400> SEQUENCE: 44

Tyr Ile Ser Tyr Thr Gly Ser Thr Tyr Tyr Asn Pro Ser Leu Lys Ser
1               5                   10                  15

<210> SEQ ID NO 45
<211> LENGTH: 16
<212> TYPE: PRT
```

<213> ORGANISM: Mus musculus

<400> SEQUENCE: 45

Tyr Ile Ser Tyr Thr Gly Ser Thr Tyr Tyr Asn Pro Ser Leu Lys Ser
1               5                   10                  15

<210> SEQ ID NO 46
<211> LENGTH: 16
<212> TYPE: PRT
<213> ORGANISM: Mus musculus

<400> SEQUENCE: 46

Val Met Trp Ala Gly Gly Gly Thr Asn Ser Asn Ser Val Leu Lys Ser
1               5                   10                  15

<210> SEQ ID NO 47
<211> LENGTH: 17
<212> TYPE: PRT
<213> ORGANISM: Artificial Sequence
<220> FEATURE:
<223> OTHER INFORMATION: Anti-Human B7-H1 Heavy Chain CDR2 Consensus
      Sequence
<220> FEATURE:
<221> NAME/KEY: MISC_FEATURE
<222> LOCATION: (1)..(1)
<223> OTHER INFORMATION: Any Amino Acid
<220> FEATURE:
<221> NAME/KEY: MISC_FEATURE
<222> LOCATION: (2)..(2)
<223> OTHER INFORMATION: I, L, M, F, or V
<220> FEATURE:
<221> NAME/KEY: MISC_FEATURE
<222> LOCATION: (3)..(3)
<223> OTHER INFORMATION: Any Amino Acid
<220> FEATURE:
<221> NAME/KEY: MISC_FEATURE
<222> LOCATION: (4)..(4)
<223> OTHER INFORMATION: P or Absent
<220> FEATURE:
<221> NAME/KEY: MISC_FEATURE
<222> LOCATION: (5)..(5)
<223> OTHER INFORMATION: A, R, N, Q, E, H, K, M, S, T, Y, or V
<220> FEATURE:
<221> NAME/KEY: MISC_FEATURE
<222> LOCATION: (6)..(6)
<223> OTHER INFORMATION: A, R, N, D, C, Q, E, G, H, K, M, F, P, S, T, Y,
      or V
<220> FEATURE:
<221> NAME/KEY: MISC_FEATURE
<222> LOCATION: (7)..(7)
<223> OTHER INFORMATION: N, G, or S
<220> FEATURE:
<221> NAME/KEY: MISC_FEATURE
<222> LOCATION: (8)..(8)
<223> OTHER INFORMATION: N, G or S
<220> FEATURE:
<221> NAME/KEY: MISC_FEATURE
<222> LOCATION: (10)..(10)
<223> OTHER INFORMATION: A, R, N, Q, E, H, K, M, S, T, or Y
<220> FEATURE:
<221> NAME/KEY: MISC_FEATURE
<222> LOCATION: (11)..(11)
<223> OTHER INFORMATION: A, R, N, C, Q, E, H, I, L, K, M, F, S, T, W, Y,
      or V
<220> FEATURE:
<221> NAME/KEY: MISC_FEATURE
<222> LOCATION: (13)..(13)
<223> OTHER INFORMATION: A, D, Q, E, K, P, S, or T
<220> FEATURE:
<221> NAME/KEY: MISC_FEATURE
<222> LOCATION: (14)..(14)
<223> OTHER INFORMATION: A, R, N, D, C, Q, E, G, H, I, L, K, M, F, P, S,
      T, Y, or V
<220> FEATURE:
<221> NAME/KEY: MISC_FEATURE

```
<222> LOCATION: (15)..(15)
<223> OTHER INFORMATION: I, L, M, or F
<220> FEATURE:
<221> NAME/KEY: MISC_FEATURE
<222> LOCATION: (17)..(17)
<223> OTHER INFORMATION: A, G or S

<400> SEQUENCE: 47

Xaa Xaa Xaa Xaa Xaa Xaa Xaa Xaa Thr Xaa Xaa Asn Xaa Xaa Xaa Lys
1               5                   10                  15

Xaa

<210> SEQ ID NO 48

<400> SEQUENCE: 48

000

<210> SEQ ID NO 49
<211> LENGTH: 7
<212> TYPE: PRT
<213> ORGANISM: Mus musculus

<400> SEQUENCE: 49

Glu Asn Trp Val Gly Asp Phe
1               5

<210> SEQ ID NO 50
<211> LENGTH: 8
<212> TYPE: PRT
<213> ORGANISM: Mus musculus

<400> SEQUENCE: 50

Tyr Gly Gly Trp Leu Ser Pro Phe
1               5

<210> SEQ ID NO 51
<211> LENGTH: 8
<212> TYPE: PRT
<213> ORGANISM: Mus musculus

<400> SEQUENCE: 51

Arg Gly Gly Trp Leu Leu Pro Phe
1               5

<210> SEQ ID NO 52
<211> LENGTH: 10
<212> TYPE: PRT
<213> ORGANISM: Mus musculus

<400> SEQUENCE: 52

Tyr Tyr Gly Asn Ser Pro Tyr Tyr Ala Ile
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Anti-Human B7-H1 Heavy Chain CDR3 Consensus
      Sequence
<220> FEATURE:
<221> NAME/KEY: MISC_FEATURE
<222> LOCATION: (1)..(1)
<223> OTHER INFORMATION: A, R, N, Q, E, H, K, M, S, T, or Y
<220> FEATURE:
<221> NAME/KEY: MISC_FEATURE
```

```
<222> LOCATION: (2)..(2)
<223> OTHER INFORMATION: A, R, N, D, C, Q, E, G, H, K, M, F, P, S, T, Y,
      or V
<220> FEATURE:
<221> NAME/KEY: MISC_FEATURE
<222> LOCATION: (3)..(3)
<223> OTHER INFORMATION: Q, G, H, T, or W
<220> FEATURE:
<221> NAME/KEY: MISC_FEATURE
<222> LOCATION: (4)..(7)
<223> OTHER INFORMATION: Any Amino Acid
<220> FEATURE:
<221> NAME/KEY: MISC_FEATURE
<222> LOCATION: (8)..(8)
<223> OTHER INFORMATION: F or Y
<220> FEATURE:
<221> NAME/KEY: MISC_FEATURE
<222> LOCATION: (9)..(9)
<223> OTHER INFORMATION: AI or Absent

<400> SEQUENCE: 53

Xaa Xaa Xaa Xaa Xaa Xaa Xaa Xaa Xaa
1               5

<210> SEQ ID NO 54
<211> LENGTH: 10
<212> TYPE: PRT
<213> ORGANISM: Mus musculus

<400> SEQUENCE: 54

Ser Ala Ser Ser Ser Val Ser Tyr Met Tyr
1               5                   10

<210> SEQ ID NO 55
<211> LENGTH: 11
<212> TYPE: PRT
<213> ORGANISM: Mus musculus

<400> SEQUENCE: 55

Lys Ala Ser Gln Asp Ile Asn Asn Tyr Met Ala
1               5                   10

<210> SEQ ID NO 56
<211> LENGTH: 11
<212> TYPE: PRT
<213> ORGANISM: Mus musculus

<400> SEQUENCE: 56

Lys Ala Ser Gln Ser Val Asp Thr Asn Val Ala
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Anti-Human PD-1 Light Chain CDR1 Consensus
      Sequence
<220> FEATURE:
<221> NAME/KEY: MISC_FEATURE
<222> LOCATION: (1)..(1)
<223> OTHER INFORMATION: N, Q, E, K, or S
<220> FEATURE:
<221> NAME/KEY: MISC_FEATURE
<222> LOCATION: (4)..(4)
<223> OTHER INFORMATION: N, D, Q, E, K, or S
<220> FEATURE:
<221> NAME/KEY: MISC_FEATURE
<222> LOCATION: (5)..(5)
<223> OTHER INFORMATION: N, D, Q, E, or S
<220> FEATURE:
```

-continued

```
<221> NAME/KEY: MISC_FEATURE
<222> LOCATION: (6)..(6)
<223> OTHER INFORMATION: A, C, I, L, M, F, S, T, Y, or V
<220> FEATURE:
<221> NAME/KEY: MISC_FEATURE
<222> LOCATION: (7)..(7)
<223> OTHER INFORMATION: A, R, N, D, C, Q, E, G, H, I, K, M, F, P, S, T,
      Y, or V
<220> FEATURE:
<221> NAME/KEY: MISC_FEATURE
<222> LOCATION: (8)..(8)
<223> OTHER INFORMATION: N, S or T
<220> FEATURE:
<221> NAME/KEY: MISC_FEATURE
<222> LOCATION: (9)..(9)
<223> OTHER INFORMATION: A, R, N, D, Q, E, G, H, K, M, P, S, T, or Y
<220> FEATURE:
<221> NAME/KEY: MISC_FEATURE
<222> LOCATION: (10)..(10)
<223> OTHER INFORMATION: I, L, M, or V
<220> FEATURE:
<221> NAME/KEY: MISC_FEATURE
<222> LOCATION: (11)..(11)
<223> OTHER INFORMATION: A, R, N, C, Q, E, H, I, L, K, M, F, S, T, Y,
      or V

<400> SEQUENCE: 57

Xaa Ala Ser Xaa Xaa Xaa Xaa Xaa Xaa Xaa Xaa
1               5                   10

<210> SEQ ID NO 58
<211> LENGTH: 7
<212> TYPE: PRT
<213> ORGANISM: Mus musculus

<400> SEQUENCE: 58

Leu Thr Ser Asn Leu Ala Ser
1               5

<210> SEQ ID NO 59
<211> LENGTH: 7
<212> TYPE: PRT
<213> ORGANISM: Mus musculus

<400> SEQUENCE: 59

Tyr Thr Ser Thr Leu Leu Ser
1               5

<210> SEQ ID NO 60
<211> LENGTH: 7
<212> TYPE: PRT
<213> ORGANISM: Mus musculus

<400> SEQUENCE: 60

Ser Ala Ser Tyr Arg Tyr Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Anti-Human PD-1 Light Chain CDR2 Consensus
      Sequence
<220> FEATURE:
<221> NAME/KEY: MISC_FEATURE
<222> LOCATION: (1)..(1)
<223> OTHER INFORMATION: A, R, C, Q, I, L, K, M, F, S, T, Y, or V
<220> FEATURE:
<221> NAME/KEY: MISC_FEATURE
<222> LOCATION: (2)..(2)
```

```
<223> OTHER INFORMATION: A, S, T, or V
<220> FEATURE:
<221> NAME/KEY: MISC_FEATURE
<222> LOCATION: (4)..(4)
<223> OTHER INFORMATION: A, R, N, Q, E, H, K, M, S, T, or Y
<220> FEATURE:
<221> NAME/KEY: MISC_FEATURE
<222> LOCATION: (5)..(5)
<223> OTHER INFORMATION: A, R, N, Q, L, K, M, S, T, or Y
<220> FEATURE:
<221> NAME/KEY: MISC_FEATURE
<222> LOCATION: (6)..(6)
<223> OTHER INFORMATION: A, R, C, Q, I, L, K, M, F, S, T, Y, or V

<400> SEQUENCE: 61

Xaa Xaa Ser Xaa Xaa Xaa Ser
1               5

<210> SEQ ID NO 62
<211> LENGTH: 9
<212> TYPE: PRT
<213> ORGANISM: Mus musculus

<400> SEQUENCE: 62

Gln Gln Trp Ser Ser Asn Pro Phe Thr
1               5

<210> SEQ ID NO 63
<211> LENGTH: 8
<212> TYPE: PRT
<213> ORGANISM: Mus musculus

<400> SEQUENCE: 63

Leu Gln Tyr Asp Asn Leu Trp Thr
1               5

<210> SEQ ID NO 64
<211> LENGTH: 9
<212> TYPE: PRT
<213> ORGANISM: Mus musculus

<400> SEQUENCE: 64

Gln Gln Tyr Asn Ser Tyr Pro Tyr Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Anti-Human PD-1 Light Chain CDR3 Consensus
      Sequence
<220> FEATURE:
<221> NAME/KEY: MISC_FEATURE
<222> LOCATION: (1)..(1)
<223> OTHER INFORMATION: A, R, N, Q, L, K, M, S, T, W, Y, or V
<220> FEATURE:
<221> NAME/KEY: MISC_FEATURE
<222> LOCATION: (3)..(3)
<223> OTHER INFORMATION: W or Y
<220> FEATURE:
<221> NAME/KEY: MISC_FEATURE
<222> LOCATION: (4)..(4)
<223> OTHER INFORMATION: N, D, Q, E, or S
<220> FEATURE:
<221> NAME/KEY: MISC_FEATURE
<222> LOCATION: (5)..(5)
<223> OTHER INFORMATION: N, S, or T
<220> FEATURE:
<221> NAME/KEY: MISC_FEATURE
<222> LOCATION: (6)..(6)
```

```
<223> OTHER INFORMATION: A, R, N, C, Q, E, H, I, L, K, M, F, P, S, T, Y,
      or V
<220> FEATURE:
<221> NAME/KEY: MISC_FEATURE
<222> LOCATION: (7)..(7)
<223> OTHER INFORMATION: F, W, or Y
<220> FEATURE:
<221> NAME/KEY: misc_feature
<222> LOCATION: (8)..(8)
<223> OTHER INFORMATION: Xaa can be any naturally occurring amino acid

<400> SEQUENCE: 65

Xaa Gln Xaa Xaa Xaa Xaa Xaa Xaa Thr
1               5

<210> SEQ ID NO 66
<211> LENGTH: 10
<212> TYPE: PRT
<213> ORGANISM: Mus musculus

<400> SEQUENCE: 66

Gly Phe Thr Phe Ser Asp Tyr Gly Met His
1               5                   10

<210> SEQ ID NO 67
<211> LENGTH: 10
<212> TYPE: PRT
<213> ORGANISM: Mus musculus

<400> SEQUENCE: 67

Gly Tyr Thr Phe Thr Asp Tyr Tyr Met Asn
1               5                   10

<210> SEQ ID NO 68
<211> LENGTH: 10
<212> TYPE: PRT
<213> ORGANISM: Mus musculus

<400> SEQUENCE: 68

Gly Tyr Thr Phe Thr Asn Tyr Trp Met His
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Anti-Human PD-1 Heavy Chain CDR1 Consensus
      Sequence
<220> FEATURE:
<221> NAME/KEY: MISC_FEATURE
<222> LOCATION: (2)..(2)
<223> OTHER INFORMATION: F or T
<220> FEATURE:
<221> NAME/KEY: MISC_FEATURE
<222> LOCATION: (5)..(5)
<223> OTHER INFORMATION: S or T
<220> FEATURE:
<221> NAME/KEY: MISC_FEATURE
<222> LOCATION: (6)..(6)
<223> OTHER INFORMATION: N or D
<220> FEATURE:
<221> NAME/KEY: MISC_FEATURE
<222> LOCATION: (8)..(8)
<223> OTHER INFORMATION: A, R, C, Q, E, G, H, K, M, F, S, T, W, Y, or V
<220> FEATURE:
<221> NAME/KEY: MISC_FEATURE
<222> LOCATION: (10)..(10)
<223> OTHER INFORMATION: N or H

<400> SEQUENCE: 69
```

```
Gly Xaa Thr Phe Xaa Xaa Tyr Xaa Met Xaa
1               5                   10
```

<210> SEQ ID NO 70
<211> LENGTH: 17
<212> TYPE: PRT
<213> ORGANISM: Mus musculus

<400> SEQUENCE: 70

```
Tyr Ile Ser Ser Gly Ser Tyr Thr Ile Tyr Tyr Thr Asp Thr Val Lys
1               5                   10                  15
Gly
```

<210> SEQ ID NO 71
<211> LENGTH: 17
<212> TYPE: PRT
<213> ORGANISM: Mus musculus

<400> SEQUENCE: 71

```
Asn Ile Asn Pro Tyr Asn Gly Gly Thr Thr Tyr Asn Gln Lys Phe Lys
1               5                   10                  15
Gly
```

<210> SEQ ID NO 72
<211> LENGTH: 17
<212> TYPE: PRT
<213> ORGANISM: Mus musculus

<400> SEQUENCE: 72

```
His Ile Asn Pro Ser Ser Gly Phe Thr Thr Tyr Asn Gln Asn Phe Lys
1               5                   10                  15
Asp
```

<210> SEQ ID NO 73
<211> LENGTH: 17
<212> TYPE: PRT
<213> ORGANISM: Artificial Sequence
<220> FEATURE:
<223> OTHER INFORMATION: Anti-Human PD-1 Heavy Chain CDR2 Consensus
      Sequence
<220> FEATURE:
<221> NAME/KEY: MISC_FEATURE
<222> LOCATION: (1)..(1)
<223> OTHER INFORMATION: A, R, N, Q, E, H, K, M, S, T, or Y
<220> FEATURE:
<221> NAME/KEY: MISC_FEATURE
<222> LOCATION: (3)..(3)
<223> OTHER INFORMATION: N or S
<220> FEATURE:
<221> NAME/KEY: MISC_FEATURE
<222> LOCATION: (4)..(4)
<223> OTHER INFORMATION: A, D, Q, E, K, P, S, or T
<220> FEATURE:
<221> NAME/KEY: MISC_FEATURE
<222> LOCATION: (5)..(5)
<223> OTHER INFORMATION: A, R, N, D, C, Q, E, G, H, K, M, F, P, S, T, W,
      Y, or V
<220> FEATURE:
<221> NAME/KEY: MISC_FEATURE
<222> LOCATION: (6)..(6)
<223> OTHER INFORMATION: N or S
<220> FEATURE:
<221> NAME/KEY: MISC_FEATURE
<222> LOCATION: (7)..(7)
<223> OTHER INFORMATION: A, R, N, D, C, Q, E, G, H, K, M, F, P, S, T, W,
      Y, or V
<220> FEATURE:
<221> NAME/KEY: MISC_FEATURE

```
<222> LOCATION: (8)..(8)
<223> OTHER INFORMATION: A, R, N, D, C, Q, E, G, H, K, M, F, S, T, W, Y,
      or V
<220> FEATURE:
<221> NAME/KEY: MISC_FEATURE
<222> LOCATION: (9)..(9)
<223> OTHER INFORMATION: A, C, I, L, M, T, or V
<220> FEATURE:
<221> NAME/KEY: MISC_FEATURE
<222> LOCATION: (10)..(10)
<223> OTHER INFORMATION: A, R, N, C, Q, E, H, I, L, K, M, F, S, T, W, Y,
      or V
<220> FEATURE:
<221> NAME/KEY: MISC_FEATURE
<222> LOCATION: (12)..(12)
<223> OTHER INFORMATION: N, S, or T
<220> FEATURE:
<221> NAME/KEY: MISC_FEATURE
<222> LOCATION: (13)..(13)
<223> OTHER INFORMATION: N, D,  Q, E, or S
<220> FEATURE:
<221> NAME/KEY: MISC_FEATURE
<222> LOCATION: (14)..(14)
<223> OTHER INFORMATION: R, N, D, Q, E, K, S, or T
<220> FEATURE:
<221> NAME/KEY: MISC_FEATURE
<222> LOCATION: (15)..(15)
<223> OTHER INFORMATION: I, L, M, W, Y, or V
<220> FEATURE:
<221> NAME/KEY: MISC_FEATURE
<222> LOCATION: (17)..(17)
<223> OTHER INFORMATION: N, D, G, or S

<400> SEQUENCE: 73

Xaa Ile Xaa Xaa Xaa Xaa Xaa Xaa Xaa Xaa Tyr Xaa Xaa Xaa Xaa Lys
1               5                   10                  15

Xaa

<210> SEQ ID NO 74
<211> LENGTH: 13
<212> TYPE: PRT
<213> ORGANISM: Mus musculus

<400> SEQUENCE: 74

Arg Gly Tyr Gly Ser Phe Tyr Glu Tyr Tyr Phe Asp Tyr
1               5                   10

<210> SEQ ID NO 75
<211> LENGTH: 10
<212> TYPE: PRT
<213> ORGANISM: Mus musculus

<400> SEQUENCE: 75

Gly Arg Ile Tyr Asp Gly Ser Leu Asp Tyr
1               5                   10

<210> SEQ ID NO 76
<211> LENGTH: 7
<212> TYPE: PRT
<213> ORGANISM: Mus musculus

<400> SEQUENCE: 76

Glu Asp Tyr Asp Val Asp Tyr
1               5

<210> SEQ ID NO 77
<211> LENGTH: 11
<212> TYPE: PRT
<213> ORGANISM: Artificial Sequence
<220> FEATURE:
```

```
<223> OTHER INFORMATION: Anti-Human PD-1 Heavy Chain CDR3 Consensus
      Sequence
<220> FEATURE:
<221> NAME/KEY: MISC_FEATURE
<222> LOCATION: (1)..(1)
<223> OTHER INFORMATION: A, R, N, D, Q, E, G, H, K, P, S, or T
<220> FEATURE:
<221> NAME/KEY: MISC_FEATURE
<222> LOCATION: (2)..(2)
<223> OTHER INFORMATION: A, R, N, D, Q, E, G, H, K, P, S, or T
<220> FEATURE:
<221> NAME/KEY: MISC_FEATURE
<222> LOCATION: (3)..(3)
<223> OTHER INFORMATION: I, L, M, F, Y, or V
<220> FEATURE:
<221> NAME/KEY: MISC_FEATURE
<222> LOCATION: (4)..(4)
<223> OTHER INFORMATION: A, R, N, D, C, Q, E, G, H, K, M, F, P, S, T, W,
      Y, or V
<220> FEATURE:
<221> NAME/KEY: MISC_FEATURE
<222> LOCATION: (5)..(5)
<223> OTHER INFORMATION: A, R, N, D, C, Q, E, G, H, I, K, M, F, P, S, T,
      Y, or V
<220> FEATURE:
<221> NAME/KEY: MISC_FEATURE
<222> LOCATION: (6)..(6)
<223> OTHER INFORMATION: A, R, N, D, C, Q, E, G, H, K, M, F, S, T, W, Y,
      or V
<220> FEATURE:
<221> NAME/KEY: MISC_FEATURE
<222> LOCATION: (7)..(7)
<223> OTHER INFORMATION: A, R, N, C, Q, E, H, I, L, K, M, F, S, T, Y,
      or V
<220> FEATURE:
<221> NAME/KEY: MISC_FEATURE
<222> LOCATION: (8)..(8)
<223> OTHER INFORMATION: A, R, N, Q, E, H, I, L, K, M, F, P, S, T, W, Y,
      or V
<220> FEATURE:
<221> NAME/KEY: MISC_FEATURE
<222> LOCATION: (9)..(9)
<223> OTHER INFORMATION: YYF or Absent

<400> SEQUENCE: 77

Xaa Xaa Xaa Xaa Xaa Xaa Xaa Xaa Xaa Asp Tyr
1               5                   10

<210> SEQ ID NO 78
<211> LENGTH: 95
<212> TYPE: PRT
<213> ORGANISM: Homo sapiens

<400> SEQUENCE: 78

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 79
<211> LENGTH: 95
<212> TYPE: PRT
```

<213> ORGANISM: Homo sapiens

<400> SEQUENCE: 79

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 80
<211> LENGTH: 12
<212> TYPE: PRT
<213> ORGANISM: Homo sapiens

<400> SEQUENCE: 80

Leu Thr Phe Gly Gly Gly Thr Lys Val Glu Ile Lys
1               5                   10

<210> SEQ ID NO 81
<211> LENGTH: 106
<212> TYPE: PRT
<213> ORGANISM: Artificial Sequence
<220> FEATURE:
<223> OTHER INFORMATION: Humanized Anti-Human B7-H1 Light Chain LC1_1

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Ile
            20                  25                  30

Tyr Trp Phe Gln Gln Lys Pro Gly Gln Ala Pro Arg Leu Leu Ile Tyr
        35                  40                  45

Ala Ala Phe Asn Arg Ala Thr Gly Ile Pro Ala Arg Phe Ser Gly Ser
50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 82
<211> LENGTH: 106
<212> TYPE: PRT
<213> ORGANISM: Artificial Sequence
<220> FEATURE:
<223> OTHER INFORMATION: Humanized Anti-Human B7-H1 Light Chain LC1_2

<400> SEQUENCE: 82

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Ile
            20                  25                  30

```
Tyr Trp Phe Gln Gln Lys Pro Gly Gln Ser Pro Arg Pro Leu Ile Tyr
        35                  40                  45

Ala Ala Phe Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 83
<211> LENGTH: 106
<212> TYPE: PRT
<213> ORGANISM: Artificial Sequence
<220> FEATURE:
<223> OTHER INFORMATION: Humanized Anti-Human B7-H1 Light Chain LC1_3

<400> SEQUENCE: 83

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Ile
                20                  25                  30

Tyr Trp Phe Gln Gln Lys Pro Gly Gln Ser Pro Arg Pro Leu Ile Tyr
        35                  40                  45

Ala Thr Phe Asn Leu Ala Ser Gly Ile Pro Ala Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 84
<211> LENGTH: 106
<212> TYPE: PRT
<213> ORGANISM: Artificial Sequence
<220> FEATURE:
<223> OTHER INFORMATION: Humanized Anti-Human B7-H1 Light Chain LC2_1

<400> SEQUENCE: 84

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Gly Val Ser Tyr Ile
                20                  25                  30

Tyr Trp Phe Gln Gln Lys Pro Gly Lys Ala Pro Lys Leu Leu Ile Tyr
        35                  40                  45

Ala Ala Phe Asn Leu Ala Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105
```

-continued

<210> SEQ ID NO 85
<211> LENGTH: 106
<212> TYPE: PRT
<213> ORGANISM: Artificial Sequence
<220> FEATURE:
<223> OTHER INFORMATION: Humanized Anti-Human B7-H1 Light Chain LC2_2

<400> SEQUENCE: 85

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Gly Val Ser Tyr Ile
            20                  25                  30

Tyr Trp Phe Gln Gln Lys Pro Gly Lys Ala Pro Lys Pro Leu Ile Tyr
        35                  40                  45

Ala Ala Phe Asn Leu Ala Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 86
<211> LENGTH: 106
<212> TYPE: PRT
<213> ORGANISM: Artificial Sequence
<220> FEATURE:
<223> OTHER INFORMATION: Humanized Anti-Human B7-H1 Light Chain LC2_3

<400> SEQUENCE: 86

Asp Ile Gln Leu Thr Gln Ser Pro Ser Ile Leu Ser Ala Ser Val Gly
1               5                   10                  15

Asp Arg Val Thr Ile Thr Cys Arg Ala Ser Ser Ser Val Ser Tyr Ile
            20                  25                  30

Tyr Trp Phe Gln Gln Lys Pro Gly Lys Ala Pro Lys Pro Leu Ile Tyr
        35                  40                  45

Ala Thr Phe Asn Leu Ala Ser Gly Val Pro Ser Arg Phe Ser Gly Ser
    50                  55                  60

Gly Ser Gly Thr Ser Tyr Thr Leu Thr Ile Ser Ser Leu Gln Pro Glu
65                  70                  75                  80

Asp Phe Ala Thr Tyr Tyr Cys Gln Gln Trp Ser Asn Asn Pro Leu Thr
                85                  90                  95

Phe Gly Gln Gly Thr Lys Val Glu Ile Lys
            100                 105

<210> SEQ ID NO 87
<211> LENGTH: 98
<212> TYPE: PRT
<213> ORGANISM: Homo sapiens

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe

```
                    50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg

<210> SEQ ID NO 88
<211> LENGTH: 100
<212> TYPE: PRT
<213> ORGANISM: Homo sapiens

<400> SEQUENCE: 88

Glu Val Gln Leu Val Glu Ser Gly Gly Gly Leu Trp Gln Pro Gly Arg
 1               5                  10                  15

Ser Leu Arg Leu Ser Cys Thr Ala Ser Gly Phe Thr Phe Gly Asp Tyr
                 20                  25                  30

Ala Met Ser Trp Val Arg Gln Ala Pro Gly Lys Gly Leu Glu Trp Val
             35                  40                  45

Gly Phe Ile Arg Ser Lys Ala Tyr Gly Gly Thr Thr Glu Tyr Ala Ala
     50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 89
<211> LENGTH: 16
<212> TYPE: PRT
<213> ORGANISM: Homo sapiens

<400> SEQUENCE: 89

Asp Ala Phe Asp Ile Trp Gly Gln Gly Thr Met Val Thr Val Ser Ser
 1               5                  10                  15

<210> SEQ ID NO 90
<211> LENGTH: 114
<212> TYPE: PRT
<213> ORGANISM: Artificial Sequence
<220> FEATURE:
<223> OTHER INFORMATION: Humanized Anti-Human B7-H1 Heavy Chain HC1_1

<400> SEQUENCE: 90

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Pro Asp Tyr
                 20                  25                  30

Tyr Met Asn Trp Val Arg Gln Ala Pro Gly Gln Gly Leu Glu Trp Met
             35                  40                  45

Gly Asp Ile Asp Pro Asn Tyr Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Ala Leu Thr Asp Trp Gly Gln Gly Thr Met Val Thr Val
```

Ser Ser

<210> SEQ ID NO 91
<211> LENGTH: 114
<212> TYPE: PRT
<213> ORGANISM: Artificial Sequence
<220> FEATURE:
<223> OTHER INFORMATION: Humanized Anti-Human B7-H1 Heavy Chain HC1_2

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Ser Leu Glu Trp Met
        35                  40                  45

Gly Asp Ile Asp Pro Asn Tyr Gly Gly Thr Asn Tyr Asn Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 92
<211> LENGTH: 114
<212> TYPE: PRT
<213> ORGANISM: Artificial Sequence
<220> FEATURE:
<223> OTHER INFORMATION: Humanized Anti-Human B7-H1 Heavy Chain HC1_3

<400> SEQUENCE: 92

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Tyr Met Asn Trp Val Arg Gln Ala Pro Gly Gln Ser Leu Glu Trp Met
        35                  40                  45

Gly Asp Ile Asp Pro Asn Tyr Gly Gly Thr Asn Tyr Asn Gln Lys Phe
    50                  55                  60

Gln Gly Arg Val Thr Met Thr Val Asp Arg Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser

<210> SEQ ID NO 93
<211> LENGTH: 114
<212> TYPE: PRT
<213> ORGANISM: Artificial Sequence
<220> FEATURE:
<223> OTHER INFORMATION: Humanized Anti-Human B7-H1 Heavy Chain HC2_1

<400> SEQUENCE: 93

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Tyr Thr Phe Pro Asp Tyr
                20                  25                  30

Tyr Met Asn Trp Val Arg Gln Ala Pro Gly Lys Gly Leu Glu Trp Val
            35                  40                  45

Gly Asp Ile Asp Pro Asn Tyr Gly Thr Thr Tyr Ala Ala Ser Val
        50                  55                  60

Lys Gly Arg Phe Thr Ile Ser Val Asp Arg Ser Lys Ser Ile Ala Tyr
65                  70                  75                  80

Leu Gln Met Ser Ser Leu Lys Thr Glu Asp Thr Ala Val Tyr Tyr Cys
                85                  90                  95

Thr Arg Gly Ala Leu Thr Asp Trp Gly Gln Gly Thr Met Val Thr Val
            100                 105                 110

Ser Ser
```

<210> SEQ ID NO 94
<211> LENGTH: 114
<212> TYPE: PRT
<213> ORGANISM: Artificial Sequence
<220> FEATURE:
<223> OTHER INFORMATION: Humanized Anti-Human B7-H1 Heavy Chain HC2_2

<400> SEQUENCE: 94

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Tyr Thr Phe Pro Asp Tyr
                20                  25                  30

Tyr Met Asn Trp Val Arg Gln Ala Pro Gly Lys Gly Leu Glu Trp Val
            35                  40                  45

Gly Asp Ile Asp Pro Asn Tyr Gly Thr Thr Tyr Asn Ala Ser Val
        50                  55                  60

Lys Gly Arg Phe Thr Ile Ser Val Asp Arg Ser Lys Ser Ile Ala Tyr
65                  70                  75                  80

Leu Gln Met Ser Ser Leu Lys Thr Glu Asp Thr Ala Val Tyr Tyr Cys
                85                  90                  95

Ala Arg Gly Ala Leu Thr Asp Trp Gly Gln Gly Thr Met Val Thr Val
            100                 105                 110

Ser Ser
```

<210> SEQ ID NO 95
<211> LENGTH: 114
<212> TYPE: PRT
<213> ORGANISM: Artificial Sequence
<220> FEATURE:
<223> OTHER INFORMATION: Humanized Anti-Human B7-H1 Heavy Chain HC2_3

<400> SEQUENCE: 95

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Tyr Thr Phe Pro Asp Tyr
                20                  25                  30

Tyr Met Asn Trp Val Arg Gln Ala Pro Gly Lys Gly Leu Glu Trp Val
            35                  40                  45

Gly Asp Ile Asp Pro Asn Tyr Gly Thr Thr Tyr Asn Gln Ser Val
        50                  55                  60
```

-continued

```
Lys Gly Arg Phe Thr Ile Ser Val Asp Arg Ser Lys Ser Ile Ala Tyr
 65                  70                  75                  80

Leu Gln Met Ser Ser Leu Lys Thr Glu Asp Thr Ala Val Tyr Tyr Cys
                 85                  90                  95

Ala Arg Gly Ala Leu Thr Asp Trp Gly Gln Gly Thr Met Val Thr Val
            100                 105                 110

Ser Ser
```

<210> SEQ ID NO 96
<211> LENGTH: 12
<212> TYPE: PRT
<213> ORGANISM: Homo sapiens

<400> SEQUENCE: 96

```
Cys Thr Phe Gly Gln Gly Thr Lys Leu Glu Ile Lys
  1               5                  10
```

<210> SEQ ID NO 97
<211> LENGTH: 106
<212> TYPE: PRT
<213> ORGANISM: Artificial Sequence
<220> FEATURE:
<223> OTHER INFORMATION: Humanized Anti-Human PD-1 Light Chain LC1_1

<400> SEQUENCE: 97

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Ser Ser Val Ser Tyr Met
             20                  25                  30

Tyr Trp Tyr Gln Gln Lys Pro Gly Gln Ala Pro Arg Leu Leu Ile Tyr
         35                  40                  45

Leu Ala Ser Asn Arg Ala Thr Gly Ile Pro Ala Arg Phe Ser Gly Ser
     50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Phe Thr
                 85                  90                  95

Phe Gly Gln Gly Thr Lys Leu Glu Ile Lys
            100                 105
```

<210> SEQ ID NO 98
<211> LENGTH: 106
<212> TYPE: PRT
<213> ORGANISM: Artificial Sequence
<220> FEATURE:
<223> OTHER INFORMATION: Humanized Anti-Human PD-1 Light Chain LC1_2

<400> SEQUENCE: 98

```
Gln Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Val Ser Tyr Met
             20                  25                  30

Tyr Trp Tyr Gln Gln Lys Pro Gly Gln Ala Pro Arg Leu Leu Ile Tyr
         35                  40                  45

Leu Thr Ser Asn Arg Ala Thr Gly Ile Pro Ala Arg Phe Ser Gly Ser
     50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Phe Thr
```

```
                    85                  90                  95

Phe Gly Gln Gly Thr Lys Leu Glu Ile Lys
                100                 105

<210> SEQ ID NO 99
<211> LENGTH: 106
<212> TYPE: PRT
<213> ORGANISM: Artificial Sequence
<220> FEATURE:
<223> OTHER INFORMATION: Humanized Anti-Human PD-1 Light Chain LC2_1

<400> SEQUENCE: 99

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
                20                  25                  30

Tyr Trp Tyr Gln Gln Lys Pro Gly Lys Ala Pro Lys Leu Leu Ile Tyr
            35                  40                  45

Leu Ala Ser Asn Leu Ala Ser Gly Val Pro Ser Arg Phe Ser Gly Ser
        50                  55                  60

Gly Ser Gly Thr Glu Tyr Thr Leu Thr Ile Ser Ser Leu Glu Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Leu Glu Ile Lys
                100                 105

<210> SEQ ID NO 100
<211> LENGTH: 106
<212> TYPE: PRT
<213> ORGANISM: Artificial Sequence
<220> FEATURE:
<223> OTHER INFORMATION: Humanized Anti-Human PD-1 Light Chain LC2_2

<400> SEQUENCE: 100

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Tyr Trp Tyr Gln Gln Lys Pro Gly Lys Ala Pro Lys Leu Leu Ile Tyr
            35                  40                  45

Leu Thr Ser Asn Leu Ala Ser Gly Val Pro Ser Arg Phe Ser Gly Ser
        50                  55                  60

Gly Ser Gly Thr Glu Tyr Thr Leu Thr Ile Ser Ser Leu Glu Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Leu Glu Ile Lys
                100                 105

<210> SEQ ID NO 101
<211> LENGTH: 98
<212> TYPE: PRT
<213> ORGANISM: Homo sapiens

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Ser Met Asn Trp Val Arg Gln Ala Pro Gly Lys Gly Leu Glu Trp Val
            35                  40                  45
Ser Tyr Ile Ser Ser Ser Ser Thr Ile Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg

<210> SEQ ID NO 102
<211> LENGTH: 98
<212> TYPE: PRT
<213> ORGANISM: Homo sapiens

<400> SEQUENCE: 102

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Ala Met His Trp Val Arg Gln Ala Pro Gly Gln Arg Leu Glu Trp Met
        35                  40                  45
Gly Trp Ile Asn Ala Gly Asn Gly Asn Thr Lys Tyr Ser Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg

<210> SEQ ID NO 103
<211> LENGTH: 9
<212> TYPE: PRT
<213> ORGANISM: Homo sapiens

<400> SEQUENCE: 103

Trp Gly Gln Gly Thr Thr Val Thr Val
1               5

<210> SEQ ID NO 104
<211> LENGTH: 122
<212> TYPE: PRT
<213> ORGANISM: Artificial Sequence
<220> FEATURE:
<223> OTHER INFORMATION: Humanized Anti-Human PD-1 Heavy Chain HC1_1

<400> SEQUENCE: 104

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Gly Met His Trp Val Arg Gln Ala Pro Gly Lys Gly Leu Glu Trp Val
        35                  40                  45
Ser Tyr Ile Ser Ser Gly Ser Ser Thr Ile Tyr Tyr Ala Asp Ser Val
    50                  55                  60
Lys Gly Arg Phe Thr Ile Ser Arg Asp Asn Ala Lys Asn Thr Leu Tyr
65                  70                  75                  80
```

Leu Gln Met Ser Ser Leu Arg Ala Glu Asp Thr Ala Val Tyr Tyr Cys
                    85                  90                  95

Ala Arg Arg Gly Tyr Gly Ser Phe Tyr Glu Tyr Tyr Phe Asp Tyr Trp
                100                 105                 110

Gly Gln Gly Thr Thr Val Thr Val Ser Ser
            115                 120

<210> SEQ ID NO 105
<211> LENGTH: 122
<212> TYPE: PRT
<213> ORGANISM: Artificial Sequence
<220> FEATURE:
<223> OTHER INFORMATION: Humanized Anti-Human PD-1 Heavy Chain HC1_2

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Tyr Ile Ser Ser Gly Ser Tyr Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Arg Gly Tyr Gly Ser Phe Tyr Glu Tyr Tyr Phe Asp Tyr Trp
                100                 105                 110

Gly Gln Gly Thr Thr Val Thr Val Ser Ser
            115                 120

<210> SEQ ID NO 106
<211> LENGTH: 122
<212> TYPE: PRT
<213> ORGANISM: Artificial Sequence
<220> FEATURE:
<223> OTHER INFORMATION: Humanized Anti-Human PD-1 Heavy Chain HC1_3

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Tyr Ile Ser Ser Gly Ser Tyr Thr Ile Tyr Ser Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Arg Gly Tyr Gly Ser Phe Tyr Glu Tyr Tyr Phe Asp Tyr Trp
                100                 105                 110

Gly Gln Gly Thr Thr Val Thr Val Ser Ser
            115                 120

<210> SEQ ID NO 107
<211> LENGTH: 122
<212> TYPE: PRT
<213> ORGANISM: Artificial Sequence
<220> FEATURE:
<223> OTHER INFORMATION: Humanized Anti-Human PD-1 Heavy Chain HC2_1

<400> SEQUENCE: 107

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Gly Met His Trp Val Arg Gln Ala Pro Gly Gln Arg Leu Glu Trp Met
        35                  40                  45

Gly Tyr Ile Ser Ser Gly Ser Ser Thr Ile Tyr Tyr Ser Gln Lys Phe
    50                  55                  60

Gln Gly Arg Val Thr Ile Thr Arg Asp Asn Ser Ala Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
        115                 120
```

<210> SEQ ID NO 108
<211> LENGTH: 122
<212> TYPE: PRT
<213> ORGANISM: Artificial Sequence
<220> FEATURE:
<223> OTHER INFORMATION: Humanized Anti-Human PD-1 Heavy Chain HC2_2

<400> SEQUENCE: 108

```
Glu Val Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Asp Tyr
            20                  25                  30

Gly Met His Trp Val Arg Gln Ala Pro Gly Gln Arg Leu Glu Trp Met
        35                  40                  45

Gly Tyr Ile Ser Ser Gly Ser Tyr Thr Ile Tyr Tyr Ser Gln Lys Phe
    50                  55                  60

Gln Gly Arg Val Thr Ile Thr Arg Asp Asn Ser Ala Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
        115                 120
```

<210> SEQ ID NO 109
<211> LENGTH: 122
<212> TYPE: PRT
<213> ORGANISM: Artificial Sequence
<220> FEATURE:
<223> OTHER INFORMATION: Humanized Anti-Human PD-1 Heavy Chain HC2_3

<400> SEQUENCE: 109

```
Glu Val Gln Leu Val Gln Ser Gly Ala Glu Val Lys Lys Pro Gly Ala
1               5                   10                  15
```

```
Ser Val Lys Val Ser Cys Ala Ala Ser Gly Phe Thr Phe Ser Asp Tyr
            20              25                  30

Gly Met His Trp Val Arg Gln Ala Pro Gly Gln Arg Leu Glu Trp Val
        35              40              45

Ala Tyr Ile Ser Ser Gly Ser Tyr Thr Ile Tyr Tyr Ser Gln Lys Phe
50                      55                  60

Gln Gly Arg Val Thr Ile Thr Arg Asp Asn Ser Ala Ser Thr Leu Tyr
65              70              75                      80

Met Glu Leu Ser Ser Leu Arg Ser Glu Asp Thr Ala Val Tyr Tyr Cys
                85              90                  95

Ala Arg Arg Gly Tyr Gly Ser Phe Tyr Glu Tyr Tyr Phe Asp Tyr Trp
            100             105             110

Gly Gln Gly Thr Thr Leu Thr Val Ser Ser
        115             120
```

ANTIBODIES AND OTHER MOLECULES THAT BIND B7-H1 AND PD-1

CROSS-REFERENCE TO RELATED APPLICATIONS

This application claims priority to U.S. Patent Application No. 61/477,414 (filed on Apr. 20, 2011; pending), which application is herein incorporated by reference in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

1. Field of the Invention

The present invention relates to antibodies and their antigen-binding fragments and to other molecules that are capable of immunospecifically binding to B7-H1 or PD-1. In some embodiments such molecules are additionally capable of modulating the ability of B7-H1 or B7-DC to bind to PD-1 or are capable of affecting the signaling activity of the B7-H1 or PD-1. The invention additionally concerns the uses of such molecules in the diagnosis and the treatment of cancer and other diseases.

2. Description of Related Art

A. Cell Mediated Immune Responses

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, natural killer cells (NK), and antigen-specific cytotoxic T-lymphocytes by T cells, and the release of various cytokines in response to the recognition of an antigen (Dong, C. et al. (2003) "*Immune Regulation by Novel Costimulatory Molecules*," Immunolog. Res. 28(1):39-48).

The ability of T cells to optimally mediate an immune response against an antigen requires two distinct signaling interactions (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). First, antigen that has been arrayed on the surface of antigen-presenting cells (APC) must be presented to an antigen-specific naive CD4$^+$ T cell. Such presentation delivers a signal via the T cell receptor (TCR) that directs the T cell to initiate an immune response that will be specific to the presented antigen. Second, a series of co-stimulatory and inhibitory signals, mediated through interactions between the APC and distinct T cell surface molecules, triggers first the activation and proliferation of the T cells and ultimately their inhibition. Thus, the first signal confers specificity to the immune response whereas the second signal serves to determine the nature, magnitude and duration of the response.

The immune system is tightly controlled by costimulatory and co-inhibitory ligands and receptors. These molecules provide the second signal for T cell activation and provide a balanced network of positive and negative signals to maximize immune responses against infection while limiting immunity to self (Wang, L. et al. (Mar. 7, 2011) "*VISTA, A Novel Mouse Ig Superfamily Ligand That Negatively Regulates T Cell Responses*," J. Exp. Med. 10.1084/jem.20100619:1-16; Lepenies, B. et al. (2008) "*The Role Of Negative Costimulators During Parasitic Infections*," Endocrine, Metabolic & Immune Disorders—Drug Targets 8:279-288). Of particular importance is binding between the B7.1 (CD80) and B7.2 (CD86) ligands of the Antigen Presenting Cell and the CD28 and CTLA-4 receptors of the CD4$^+$ T-lymphocyte (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). Binding of B7.1 or of B7.2 to CD28 stimulates T cell activation; binding of B7.1 or B7.2 to CTLA-4 inhibits such activation (Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T cells (Gross, J., et al. (1992) "*Identification And Distribution Of The Costimulatory Receptor CD28 In The Mouse*," J. Immunol. 149:380-388), whereas CTLA4 expression is rapidly up-regulated following T-cell activation (Linsley, P. et al. (1996) "*Intracellular Trafficking Of CTLA4 And Focal Localization Towards Sites Of TCR Engagement*," Immunity 4:535-543). Since CTLA4 is the higher affinity receptor (Sharpe, A. H. et al. (2002) "*The B7-CD28 Superfamily*," Nature Rev. Immunol. 2:116-126), binding first initiates T cell proliferation (via CD28) and then inhibits it (via nascent expression of CTLA4), thereby dampening the effect when proliferation is no longer needed.

Further investigations into the ligands of the CD28 receptor have led to the identification and characterization of a set of related B7 molecules (the "B7 Superfamily") (Coyle, A. J. et al. (2001) "*The Expanding B7 Superfamily: Increasing Complexity In Costimulatory Signals Regulating T Cell Function*," Nature Immunol. 2(3):203-209; Sharpe, A. H. et al. (2002) "*The B7-CD28 Superfamily*," Nature Rev. Immunol. 2:116-126; Greenwald, R. J. et al. (2005) "*The B7 Family Revisited*," Ann. Rev. Immunol. 23:515-548; Collins, M. et al. (2005) "*The B7 Family Of Immune-Regulatory Ligands*," Genome Biol. 6:223.1-223.7; Loke, P. et al. (2004) "*Emerging Mechanisms Of Immune Regulation: The Extended B7 Family And Regulatory T Cells*," Arthritis Res. Ther. 6:208-214; Korman, A. J. et al. (2007) "*Checkpoint Blockade in Cancer Immunotherapy*," Adv. Immunol. 90:297-339; Flies, D. B. et al. (2007) "*The New B7s: Playing a Pivotal Role in Tumor Immunity*," J. Immunother. 30(3):251-260; Agarwal, A. et al. (2008) "*The Role Of Positive Costimulatory Molecules In Transplantation And Tolerance*," Curr. Opin. Organ Transplant. 13:366-372; Lenschow, D. J. et al. (1996) "*CD28/B7 System of T Cell Costimulation*," Ann. Rev. Immunol. 14:233-258; Wang, S. et al. (2004) "*Co-Signaling Molecules Of The B7-CD28 Family In Positive And Negative Regulation Of T Lymphocyte Responses*," Microbes Infect. 6:759-766). There are currently several known members of the family: B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) "*The B7 Family Of Immune-Regulatory Ligands*," Genome Biol. 6:223.1-223.7; Flajnik, M. F. et al. (2012) "*Evolution Of The*

*B7 Family: Co-Evolution Of B7H6 And Nkp30, Identification Of A New B7 Family Member, B7H7, And Of B7's Historical Relationship With The MHC,*" Immunogenetics epub doi.org/10.1007/s00251-012-0616-2).

B. B7-H1/PD1 Interactions

1. B7-H1

B7-H1 (PD-L1, CD274) is a particularly significant member of the B7 Superfamily as it is pivotally involved in shaping the immune response to tumors (Flies, D. B. et al. (2007) "*The New B7s: Playing a Pivotal Role in Tumor Immunity,*" J. Immunother. 30(3):251-260; U.S. Pat. Nos. 6,803,192; 7,794,710; United States Patent Application Publication Nos. 2005/0059051; 2009/0055944; 2009/0274666; 2009/0313687; PCT Publication No. WO 01/39722; WO 02/086083). B7-H1 is an approximately 33 kDa type 1 transmembrane protein. It has been speculated to play a major role in suppressing the immune system during particular events such as pregnancy, tissue allografts, autoimmune disease and other disease states such as hepatitis.

B7-H1 is broadly expressed in different human and mouse tissues, such as heart, placenta, muscle, fetal liver, spleen, lymph nodes, and thymus for both species as well as liver, lung, and kidney in mouse only (Martin-Orozco, N. et al. (2007) "*Inhibitory Costimulation And Anti-Tumor Immunity,*" Semin. Cancer Biol. 17(4):288-298). In humans, B7-H1 protein expression has been found in human endothelial cells (Chen, Y. et al. (2005) "*Expression of B7-H1 in Inflammatory Renal Tubular Epithelial Cells,*" Nephron. Exp. Nephrol. 102:e81-e92; de Haij, S. et al. (2005) "*Renal Tubular Epithelial Cells Modulate T-Cell Responses Via ICOS-L And B7-H1*" Kidney Int. 68:2091-2102; Mazanet, M. M. et al. (2002) "*B7-H1 Is Expressed By Human Endothelial Cells And Suppresses T Cell Cytokine Synthesis,*" J. Immunol. 169: 3581-3588), myocardium (Brown, J. A. et al. (2003) "*Blockade Of Programmed Death-1 Ligands On Dendritic Cells Enhances T Cell Activation And Cytokine Production,*" J. Immunol. 170:1257-1266), syncyciotrophoblasts (Petroff, M. G. et al. (2002) "*B7 Family Molecules: Novel Immunomodulators At The Maternal-Fetal Interface,*" Placenta 23:S95-S101), resident macrophages of some tissues, or in macrophages that have been activated with interferon (IFN)-γ or tumor necrosis factor (TNF)-α (Latchman, Y. et al. (2001) "*PD-L2 Is A Second Ligand For PD-1 And Inhibits T Cell Activation,*" Nat. Immunol 2:261-268), and in tumors (Dong, H. (2003) "*B7-H1 Pathway And Its Role In The Evasion Of Tumor Immunity,*" J. Mol. Med. 81:281-287). In the mouse, B7-H1 protein expression is found in heart endothelium, islets cells of the pancreas, small intestines, and placenta (Martin-Orozco, N. et al. (2007) "*Inhibitory Costimulation And Anti-Tumor Immunity,*" Semin. Cancer Biol. 17(4):288-298).

2. PD-1

Programmed Death-1 ("PD-1") is a receptor of B7-H1 and B7-DC. PD-1 is an approximately 31 kD type I membrane protein member of the extended CD28/CTLA4 family of T cell regulators (Ishida, Y. et al. (1992) "*Induced Expression Of PD-1, A Novel Member Of The Immunoglobulin Gene Superfamily, Upon Programmed Cell Death,*" EMBO J. 11:3887-3895; United States Patent Application Publication No. 2007/0202100; 2008/0311117; 2009/00110667; U.S. Pat. Nos. 6,808,710; 7,101,550; 7,488,802; 7,635,757; 7,722,868; PCT Publication No. WO 01/14557). Compared to CTLA4, PD-1 more broadly negatively regulates immune responses.

PD-1 is expressed on activated T cells, B cells, and monocytes (Agata, Y. et al. (1996) "*Expression Of The PD-1 Antigen On The Surface Of Stimulated Mouse T And B Lymphocytes,*" Int. Immunol. 8(5):765-772; Yamazaki, T. et al. (2002) "*Expression Of Programmed Death 1 Ligands By Murine T Cells And APC,*" J. Immunol. 169:5538-5545) and at low levels in natural killer (NK) T cells (Nishimura, H. et al. (2000) "*Facilitation Of Beta Selection And Modification Of Positive Selection In The Thymus Of PD-1-Deficient Mice,*" J. Exp. Med. 191:891-898; Martin-Orozco, N. et al. (2007) "*Inhibitory Costimulation And Anti-Tumor Immunity,*" Semin. Cancer Biol. 17(4):288-298).

The extracellular region of PD-1 consists of a single immunoglobulin (Ig)V domain with 23% identity to the equivalent domain in CTLA4 (Martin-Orozco, N. et al. (2007) "*Inhibitory Costimulation And Anti-Tumor Immunity,*" Semin. Cancer Biol. 17(4):288-298). The extracellular IgV domain is followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals (Ishida, Y. et al. (1992) "*Induced Expression Of PD-1, A Novel Member Of The Immunoglobulin Gene Superfamily, Upon Programmed Cell Death,*" EMBO J. 11:3887-3895; Blank, C. et al. (Epub 2006 Dec. 29) "*Contribution Of The PD-L1/PD-1 Pathway To T-Cell Exhaustion: An Update On Implications For Chronic Infections And Tumor Evasion* Cancer," Immunol. Immunother. 56(5):739-745).

Antibodies capable of immunospecifically binding to murine PD-1 have been reported (see, e.g., Agata, T. et al. (1996) "*Expression Of The PD-1 Antigen On The Surface Of Stimulated Mouse T And B Lymphocytes,*" Int. Immunol. 8(5): 765-772).

C. The Interactions of B7-H1 and PD-1

Interaction of B7-H1 and PD-1 has been found to provide a crucial negative co-stimulatory signal to T and B cells (Martin-Orozco, N. et al. (2007) "*Inhibitory Costimulation And Anti-Tumor Immunity,*" Semin. Cancer Biol. 17(4):288-298) and functions as a cell death inducer (Ishida, Y. et al. (1992) "*Induced Expression Of PD-1, A Novel Member Of The Immunoglobulin Gene Superfamily, Upon Programmed Cell Death,*" EMBO J. 11:3887-3895; Subudhi, S. K. et al. (2005) "*The Balance Of Immune Responses: Costimulation Verse Coinhibition,*" J. Molec. Med. 83:193-202).

Interaction between low concentrations of the PD-1 receptor and the B7-H1 ligand results in the transmission of an inhibitory signal that strongly inhibits the proliferation of antigen-specific $CD8^+$ T cells; at higher concentrations the interactions with PD-1 do not inhibit T-cell proliferation but markedly reduce the production of multiple cytokines (Sharpe, A. H. et al. (2002) "*The B7-CD28 Superfamily,*" Nature Rev. Immunol. 2:116-126). T-cell proliferation and cytokine production by both resting and previously activated CD4 and CD8 T cells, and even naive T cells from umbilical-cord blood, have been found to be inhibited by soluble B7-H1-Fc fusion proteins (Freeman, G. J. et al. (2000) "*Engagement Of The PD-1 Immunoinhibitory Receptor By A Novel B7 Family Member Leads To Negative Regulation Of Lymphocyte Activation,*" J. Exp. Med. 192:1-9; Latchman, Y. et al. (2001) "*PD-L2 Is A Second Ligand For PD-1 And Inhibits T Cell Activation,*" Nature Immunol. 2:261-268; Carter, L. et al. (2002) "*PD-1:PD-L inhibitory pathway affects both CD4(+) and CD8(+) T cells and is overcome by IL-2,*" Eur. J. Immunol. 32(3):634-643; Sharpe, A. H. et al. (2002) "*The B7-CD28 Superfamily,*" Nature Rev. Immunol. 2:116-126).

B7-H1-PD-1 interactions lead to cell cycle arrest in G0-G1 but do not increase cell death (Latchman, Y. et al. (2001) "*PD-L2 Is A Second Ligand For PD-1 And Inhibits T Cell Activation,*" Nature Immunol. 2:261-268; Carter, L. et al.

(2002) "*PD-1:PD-L inhibitory pathway affects both CD4(+) and CD8(+) T cells and is overcome by IL-2*," Eur. J. Immunol. 32(3):634-643). Thus, B7-H1-PD-1 complexing has the ability to antagonize the B7-CD28 signal when antigenic stimulation is weak or limiting, and plays a key role in down-regulating T-cell responses.

The signal transduction mediated by B7-H1 and PD-1 is complex. Both molecules additionally bind to other proteins. B7-H1 is capable of binding to B7-1 (CD80) (Butte, M. J. et al. (2008) "*Interaction of PD-L1 and B7-1*," Molecular Immunol. 45:3567-3572); PD-1 is capable of binding to B7-DC (PD-L2) (Lázár-Molnár, E. et al. (2008) "*Crystal Structure Of The Complex Between Programmed Death-1 (PD-1) And Its Ligand PD-L2*," Proc. Natl. Acad. Sci. (USA) 105(30):10483-10488). B7-1 interacts with CD28 to deliver a co-stimulatory signal for T-cell activation that is important in the early stages of immune response (Elloso, M. M. et al. (1999) "Expression and Contribution of B7-1 (CD80) and B7-2 (CD86) in the Early Immune Response to *Leishmania major* Infection," J. Immunol. 162:6708-6715). B7-DC is a strong stimulator of T cells, enhancing T cell proliferation and IFN-γ production. However, it also exhibits an inhibitory effect on the immune response via its interaction with PD-1 (Ishiwata, K. et al. (epub Jan. 10, 2010) "*Costimulator Responses Induced by Nippostrongylus brasiliensis*," J. Immunol. 184:2086-2094). Microbes and tumors appear to have exploited PD-1 and B7-H1 to evade eradication by the immune system. Differences in binding affinities to the various receptors and ligands that interact with PD-1 and B7-H1 have been proposed to provide distinct functional outcomes of blockade of PD-1 and B7-H1 in disease models (Butte, M. J. et al. (2008) "*Interaction of PD-L1 and B7-1*," Molecular Immunol. 45:3567-3572). The PD-1 pathway has also been implicated as playing a key role in the impairment of immune function during chronic infection ("T cell exhaustion"), and a blockade of PD-1 function is able to restore many T cell functions (Rodríquez-García, M. et al. (Nov. 19, 2010) "*Expression Of PD-L1 And PD-L2 On Human Macrophages Is Up-Regulated By HIV-1 And Differentially Modulated By IL-10*," J. Leukocyte Biol. 89: doi:10.1189/jlb.0610327:1-9).

The role of B7-H1 and PD-1 in inhibiting T cell activation and proliferation has suggested that these biomolecules might serve as therapeutic targets for treatments of inflammation and cancer. The use of anti-PD1 antibodies to treat infections and tumors and up-modulate an adaptive immune response has been proposed (see, United States Patent Application Publication Nos. 2010/0040614; 2010/0028330; 2004/0241745; 2008/0311117; 2009/0217401; U.S. Pat. Nos. 7,521,051; 7,563,869; 7,595,048; PCT Publications Nos. WO 2004/056875; WO 2008/083174). Conversely, agents that modulate the interaction of PD-1 with B7-H1 have been suggested to have utility in up- or down-modulating the immune response (see, U.S. Pat. Nos. 7,029,674; 7,488,802; United States Patent Application Publications Nos. 2007/0122378; 2009/0076250; 2009/0110667; 2009/0263865; 2009/0297518; PCT Publication No. WO 2006/133396). Likewise, the use of anti-B7-H1 antibodies to treat infections and tumors and up-modulate an adaptive immune response has been proposed (United States Patent Application Publication Nos. 2009/0055944; 2009/0274666; 2009/0317368; U.S. Pat. Nos. 6,803,192; 7,794,710; PCT Publications Nos. WO 01/39722; WO 02/086083).

Nevertheless, despite all such advances a need remains for compositions capable of modulating the interaction between B7-H1 and PD-1. The present invention is directed to such compositions and their use to treat cancer and other diseases and conditions.

SUMMARY OF THE INVENTION

The present invention relates to antibodies and their antigen-binding fragments and to other molecules that are capable of immunospecifically binding to B7-H1 or PD-1. In some embodiments such molecules are additionally capable of modulating the ability of B7-H1 to bind to PD-1 or are capable of affecting the signaling activity of the B7-H1 or PD-1. The invention additionally concerns the uses of such molecules in the diagnosis and treatment of cancer and other diseases.

In detail, the invention provides a molecule, comprising an antigen-binding fragment of an antibody that immunospecifically binds to B7-H1 or PD-1, and in particular human B7-H1 or human PD-1, preferably expressed on the surface of a live cell at an endogenous or transfected concentration. The invention particularly concerns the embodiment of such a molecule wherein the antigen-binding fragment binds to B7-H1, and wherein the live cell is a tumor cell, a pathogen-infected cell or an Antigen Presenting Cell as well as the embodiment of such a molecule wherein the antigen-binding fragment binds to PD-1, and wherein the live cell is a T cell.

The present invention relates to antibodies and their antigen-binding fragments and to other molecules that are capable of immunospecifically binding to B7-H1 or PD-1. In some embodiments such molecules are additionally capable of modulating the ability of B7-H1 to bind to PD-1 or are capable of affecting the signaling activity of the B7-H1 or PD-1. The invention additionally concerns the uses of such molecules in the diagnosis and treatment of cancer and other diseases.

In detail, the invention provides a molecule, comprising an antigen-binding fragment of an antibody that immunospecifically binds to B7-H1 or PD-1, and in particular human B7-H1 or human PD-1, preferably expressed on the surface of a live cell at an endogenous or transfected concentration. The invention particularly concerns the embodiment of such a molecule wherein the antigen-binding fragment binds to B7-H1, and wherein the live cell is a tumor cell, a pathogen-infected cell or an Antigen Presenting Cell as well as the embodiment of such a molecule wherein the antigen-binding fragment binds to PD-1, and wherein the live cell is a T cell.

The invention further concerns the embodiment of such molecules wherein the molecule is a monoclonal antibody, a human antibody, a chimeric antibody or a humanized antibody. The invention includes the embodiments wherein such antibodies are monospecific, bispecific, trispecific or multispecific.

The invention further concerns the embodiment of such molecules or antibodies which binds to B7-H1, and wherein the antigen-binding fragment thereof comprises six CDRs, wherein the CDRs comprise at least one consensus CDR of the CDRs of anti-B7-H1 antibodies 1E12, 1F4, 2G11, 3B6, and 3D10 with all remaining CDRs selected from:
(A) the three light chain and the three heavy chain CDRs of anti-B7-H1 antibody 1E12;
(B) the three light chain and the three heavy chain CDRs of anti-B7-H1 antibody 1F4;
(C) the three light chain and the three heavy chain CDRs of anti-B7-H1 antibody 2G11;
(D) the three light chain and the three heavy chain CDRs of anti-B7-H1 antibody 3B6; or
(E) the three light chain and the three heavy chain CDRs of anti-B7-H1 antibody 3D10.

The invention further concerns the embodiment of such molecules or antibodies which binds to B7-H1, and wherein the antigen-binding fragment thereof comprises six CDRs, wherein the six CDRs are:
(A) the three light chain and the three heavy chain CDRs of anti-B7-H1 antibody 1E12;
(B) the three light chain and the three heavy chain CDRs of anti-B7-H1 antibody 1F4;
(C) the three light chain and the three heavy chain CDRs of anti-B7-H1 antibody 2G11;
(D) the three light chain and the three heavy chain CDRs of anti-B7-H1 antibody 3B6; or
(E) the three light chain and the three heavy chain CDRs of anti-B7-H1 antibody 3D10.

The invention further concerns the embodiment of such antibodies, wherein the antibody binds to B7-H1 and comprises a variable domain of antibody h3D10 Var 1, h3D10 Var 2, h3D10 Var 3, h3D10 Var 4, h3D10 Var 5, h3D10 Var 6, h3D10 Var 7, h3D10 Var 8, h3D10 Var 9, h3D10 Var 10, h3D10 Var 11, h3D10 Var 12, h3D10 Var 13, or h3D10 Var 14.

The invention further concerns the embodiment of the above-described molecules or antibodies, wherein the molecules or antibodies bind to PD-1, and wherein the antigen-binding fragment comprises six CDRs, wherein the CDRs comprise at least one consensus CDR of the CDRs of anti-PD-1 antibodies 1E3, 1E8 and 1H3 with all remaining CDRs selected from:
(A) the three light chain and the three heavy chain CDRs of anti-PD-1 antibody 1E3;
(B) the three light chain and the three heavy chain CDRs of anti-PD-1 antibody 1E8; or
(C) the three light chain and the three heavy chain CDRs of anti-PD-1 antibody 1H3.

The invention further concerns the embodiment of such antibodies, wherein the six CDRs are:
(A) the three light chain and the three heavy chain CDRs of anti-PD-1 antibody 1E3;
(B) the three light chain and the three heavy chain CDRs of anti-PD-1 antibody 1E8; or
(C) the three light chain and the three heavy chain CDRs of anti-PD-1 antibody 1H3.

The invention further concerns the embodiment of such antibodies, wherein the antibody binds to PD-1 and comprises a variable domain of antibody h1H3 Var 1, h1H3 Var 2, h1H3 Var 3, h1H3 Var 4, h1H3 Var 5, h1H3 Var 6, h1H3 Var 7, h1H3 Var 8, h1H3 Var 9, h1H3 Var 10, h1H3 Var 11, h1H3 Var 12, h1H3 Var 13, or h1H3 Var 14.

The invention further concerns the embodiment of the above-described molecules or antibodies, wherein the molecule or antibody is detectably labeled or comprises a conjugated toxin, drug, receptor, enzyme, receptor ligand.

The invention further concerns the embodiment of the above-described molecules or antibodies, wherein the molecule or antibody:
(A) modulates signal transduction mediated by B7-H1 or PD-1;
(B) attenuates the ability of B7-H1 to bind to a B7-H1 receptor or attenuates the ability of PD-1 to bind to a PD-1 ligand;
(C) agonizes B7-H1 or PD-1 mediated signal transduction;
(D) mediates T cell proliferation; or
(E) enhances the production of IFN-γ.

The invention further concerns a pharmaceutical composition comprising a therapeutically effective amount of any of the above-described molecules or antibodies, and a physiologically acceptable carrier or excipient. The invention further concerns the use of such pharmaceutical composition in the treatment of cancer, autoimmune disease, infectious disease, or a disease affecting T cell number or health. The invention further concerns the use of such pharmaceutical composition, wherein the treatment is prophylactic, and is provided in advance of any symptom of the cancer, the autoimmune disease, the infectious disease, or the disease affecting T cell number or health, or for the treatment of conditions incident to transplantation.

The invention further concerns the use of any of the above-described molecules or antibodies for diagnosing cancer, autoimmune disease (especially graft vs. host disease), infectious disease (especially a chronic viral disease), or a disease affecting T cell number or health in a subject by assaying cells of the subject for their ability to bind to B7-H1 or PD-1.

The invention particularly concerns the embodiment of such molecules, antibodies and compositions, wherein the B7-H1 is human B7-H1 and the PD-1 is human PD-1.

The invention particularly concerns a method for diagnosing a disease (especially cancer) in a subject comprising assaying cells of the subject for their ability to bind to any of the above-described B7-H1 binding molecules, wherein the method provides a cytologic assay for diagnosing the presence of the disease in the subject.

The invention additionally concerns a method for diagnosing a disease (especially a disease affecting T cell number and/or health) in a subject comprising assaying cells of the subject for their ability to bind to a PD-1 binding molecule, wherein the method provides a cytologic assay for diagnosing the presence and/or progression of the disease in the subject, or for assessing a subject's response to treatment.

DETAILED DESCRIPTION OF THE INVENTION

Figure 1:
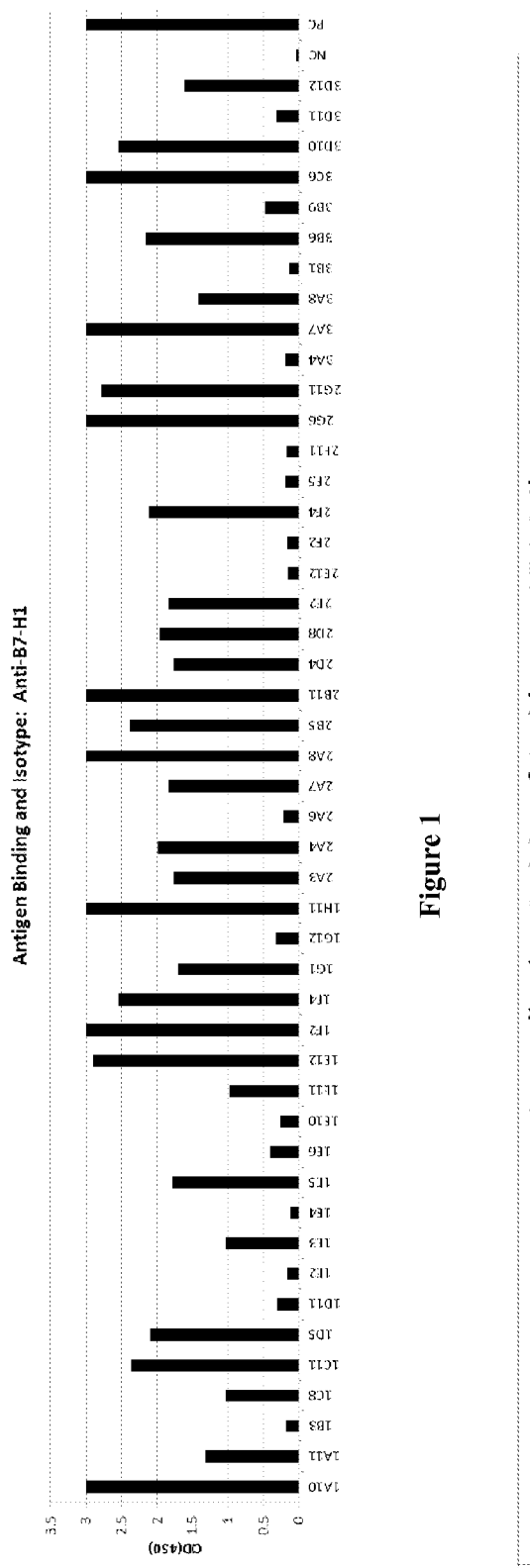
FIG. 1 shows the binding of tested hybridoma supernatants for antibody that bind to B7-H1. Positive control (PC): 1:1000 diluted sera from the mouse used for hybridoma generation; Negative control (NC): 5% milk/PBS. Data is shown for binding to B7-H1-Fc and detection with anti-mouse IgG.

The present invention relates to antibodies and their antigen-binding fragments and to other molecules that are capable of immunospecifically binding to B7-H1 or PD-1. In some embodiments such molecules are additionally capable of modulating the ability of B7-H1 or B7-DC to bind to PD-1 or are capable of affecting the signaling activity of B7-H1 or PD-1. The invention additionally concerns the uses of such molecules in the treatment of cancer and other diseases.

A molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen (and in particular, the antigens: B7-H1 or PD-1) if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein the term "modulate" relates to a capacity to alter an effect or result. In particular, the invention relates to molecules (especially antibodies or their antigen-binding fragments that immunospecifically bind human B7-H1 or human PD-1) that are capable of modulating the binding between B7-H1 and PD-1 and/or of modulating the signal transduction that occurs as a consequence of B7-H1-PD-1 binding. Such modulation may result in attenuating or in completely blocking the ability of B7-H1 to bind to PD-1. In a further embodiment, such modulation may attenuate or completely neutralize the ability of B7-H1 or PD-1 to mediate signal transduction. In a further embodiment, such modulation may enhance or otherwise agonize signal transduction through B7-H1 or PD-1, either by 1) enhancing the interaction between B7-H1 and PD-1 and facilitating B7-H1-PD-1 binding or ii) directly binding to B7-H1 and PD-1 and thus mimicking the activity of the endogenous ligand, etc. In a still further embodiment, such modulation may alter the nature of the interaction between B7-H1 and PD-1 so as to alter the nature of the elicited signal transduction. For example, the molecules of the present invention can, by binding to B7-H1 or PD-1, alter the ability of such molecules to bind to other ligands and receptor (e.g., affecting the ability of PD-1 to bind to B7-DC or the ability of B7-H1 to bind to B7-1 (CD80)) and thereby alter their overall activity. Preferably, such modulation will provide at least a 10% change in a measurable immune system activity, more preferably, at least a 50% change in such activity, or at least a 2-fold, 5-fold, 10-fold, or still more preferably, at least a 100-fold change in such activity.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia, C. et al. (1987) "Canonical Structures For The Hypervariable Regions Of Immunoglobulins," *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat.

No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies of the invention). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind antigen. Such fragments include Fab', $F(ab')_2$, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized antibodies are particularly preferred for in vivo use in humans, however, murine antibodies or antibodies of other species may be advantageously employed for many uses (for example, in vitro or in situ detection assays, acute in vivo use, etc.). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530, 101, and 5,585,089), veneering or resurfacing (EP 592,106; EP 519,596; Padlan, 1991, *Molecular Immunology* 28(4/5): 489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332).

The invention particularly concerns "humanized antibodies" (see, e.g., European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J. Immunol.* 169:1119-25; Caldas et al., 2000, *Protein Eng.* 13:353-60; Morea et al., 2000, *Methods* 20:267-79; Baca et al., 1997, *J. Biol. Chem.* 272:10678-84; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-73; Jones et al., 1986, *Nature* 321:522-525; Reichmann et al., 1988, *Nature* 332:323-329; and Presta, 1992, *Curr. Op. Struct. Biol.* 2:593-596). As used herein, the term "humanized antibody" refers to an immunoglobulin comprising a human framework region and one or more CDR's from a non-human (usually a mouse or rat)

immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to a FcγRIIB polypeptide, that has been altered by the introduction of amino acid residue substitutions, deletions or additions (i.e., mutations).

The antibodies used in the methods of the present invention may be monospecific. Also of interest are bispecific antibodies, trispecific antibodies or antibodies of greater multispecificity that exhibit specificity to different targets in addition to B7-H1 or PD-1. In a preferred embodiment, such multispecific antibodies would exhibit specificity to different immune cell target(s). For example, such antibodies may bind to both B7-H1 and B7-DC and thus modulate both PD-1 dependent responses. Conversely, such antibodies may bind to PD-1 and B7-1 and interfere with both B7-H1 dependent responses. In another embodiment, the multispecific antibody binds to molecules (receptors or ligands) involved in alternative immunomodulatory pathways, such as CTLA4, TIM3, TIM4, OX40, CD40, GITR, 4-1-BB, B7-H4, LIGHT or LAG3, in order to enhance the immunomodulatory effects. Furthermore, the multispecific antibody may bind to effecter molecules such as cytokines (e.g., IL-7, IL-15, IL-12, IL-4 TGF-beta, IL-10, IL-17, IFNg, Flt3, BLys) and chemokines (e.g., CCL21), which may be particularly relevant for modulating both acute and chronic immune responses.

Additionally, multispecific antibodies may bind to an antigen that is important for targeting the antibody to a particular cell type or tissue. For example such antibodies that bind both PD-1 and CD27 (or B7-H1 and CD27) can help co-localize activated memory B-cells ($mB_{Act}$) and antigen presenting cells (APCs) so that the PD-1 arrayed by such APCs can interact with ligands on the surface of the $mB_{Act}$ B-cells to promote the survival of the $mB_{Act}$ B-cells. Since a loss of $mB_{Act}$ B-cells is a precipitating event in the progression of HIV-infection to AIDS (Titanji, K. et al. (2010) "*Acute Depletion Of Activated Memory B Cells Involves The PD-1 Pathway In Rapidly Progressing SIV-Infected Macaques,*" J. Clin. Invest. 120(11):3878-3890), antibodies that bind both PD-1 and CD27 have utility in the treatment of HIV infection and in preventing or delaying the onset of AIDS. As discussed above, the PD-1 pathway has been implicated as playing a key role in the impairment of immune function during chronic HIV infection ("T cell exhaustion") (Khaitan, A. et al. (2011) "*Revisiting Immune Exhaustion During HIV Infection,*" Curr. HIV/AIDS Rep. 8:4-11; Rodríquez-García, M. et al. (Nov. 19, 2010) "*Expression Of PD-L1 And PD-L2 On Human Macrophages Is Up-Regulated By HIV-1 And Differentially Modulated By IL-10,*" J. Leukocyte Biol. 89: doi:10.1189/jlb.0610327:1-9; Grabmeier-Pfistershammer, K. et al. (2011) "*Identification of PD-1 as a Unique Marker for Failing Immune Reconstitution in HIV-1-Infected Patients on Treatment,*" J Acquir. Immune Defic. Syndr. 56(2):118-124). Macrophages have been shown to contribute significantly to the initial steps of HIV infection (Carter, C. A. et al. (2008) "*Cell Biology Of HIV-1 Infection Of Macrophages,*" Ann. Rev. Microbiol. 62:425-443; Noursadeghi, M. et al. (2006) "*HIV-1 Infection Of Mononuclear Phagocytic Cells: The Case For Bacterial Innate Immune Deficiency In AIDS,*" Lancet Infect. Dis. 6:794-804). Accordingly, antibodies (particularly if conjugated to a toxin) that bind to PD-1 and to a macrophage-specific marker (such as CD14, CD68, CD163, TLR2 etc.) have utility in preventing HIV infection. Additionally, antibodies that bind to multiple markers of T cell exhaustion (e.g., PD-1 and any or all of: CTLA4, TIM3, TIM4 or LAG-3) have utility in the treatment or diagnosis of immune responsiveness. Other target antigens of interest include cancer cell markers.

Additionally, it has been found that PD-1$^+$ CD8$^+$ cells have anti-HIV activity (Killian, M. S. et al. (2011) "*Natural Suppression of Human Immunodeficiency Virus Type* 1 *Replication Is Mediated by Memory CD8$^+$ T Cells,*" J. Virol. 85(4): 1696-1705). Thus antibodies that bind to both PD-1 and CD8 have utility in, for example, an ex vivo means for isolating and producing an enriched population of such cells for ultimate use in the treatment of HIV infection and AIDS in patients.

Other markers that may be used in such anti-PD-1 or anti-B7-H1 bispecific, trispecific or multispecific antibodies include CD4, CD8, CD25 and CTLA-4 (see, De Keersmaecker, B. et al. (2011) ("*Fighting with the Enemy's Weapons? The Role of Costimulatory Molecules in HIV,*" Curr. Molec. Med. 566-5240/11: 1-25; and Sarikonda, G. (2011) "*Immunosuppressive Mechanisms During Viral Infectious Diseases*;" Methods in Molec. Biol. 677:431-447, both herein incorporated by reference).

Similarly, although CD4 T cells are required to slow the growth and spread of *M. tuberculosis*, PD-1-mediated inhibition is also required to prevent CD4$^+$ T cells from promoting severe disease (Barber, D. L. et al. (2011) "*CD4 T Cells Promote Rather than Control Tuberculosis in the Absence of PD-1-Mediated Inhibition,*" J. Immunol. 186:1598-1607; Sakai, S. et al. (2010) "*PD-1-PD-L1 pathway impairs $T_h1$ immune response in the late stage of infection with Mycobacterium bovis bacillus Calmette-Guérin,*" Intl. Immunol. 22(12):915-925; Lázár-Molnár, E. et al. (2010) "*Programmed Death-1 (PD-1)-Deficient Mice Are Extraordinarily Sensitive To Tuberculosis,*" Proc. Natl. Acad. Sci. (USA) 107(30):13402-13407). Thus, antibodies that bind to CD4 and PD-1 have utility in the treatment of tuberculosis and in preventing or delaying the onset of tuberculosis.

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, *J. Mol. Biol.* 278: 457-479 for a listing of human framework regions).

A humanized or chimeric antibody of the invention may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, an antibody of the invention also comprises at least a portion of an immunoglobulin constant region (Fc), typically that of a human immunoglobulin. The constant domains of the antibodies of the invention may be selected with respect to the proposed function of the antibody, in particular the effector function which may be required. In some embodiments, the constant domains of the antibodies of the invention are (or comprise) human IgA, IgD, IgE, IgG or IgM domains. In a specific embodiment, human IgG constant domains, especially of the IgG1 and IgG3 isotypes are used, when the humanized antibodies of the invention is intended for therapeutic uses and antibody effector functions such as antibody-dependent cell-mediated cytotoxicity (ADCC) and complement-dependent cytotoxicity (CDC) activity are needed. For example, PD-1 is highly expressed on T cells as well as rare peripheral T cell lymphomas such as Angioimmunoblastic T-cell lymphoma (AITL). Anti-PD-1 antibodies with ADCC or CDC activity are particularly relevant as therapeutic agents for treating such cancers. In alternative embodiments, IgG2 and IgG4 isotypes are used when the antibody of the invention is intended for therapeutic purposes and antibody effector function is not required. For example, if you want to increase the activity of T cells by targeting PD-1 on the surface of T cells, then effector functions that would kill the T cell may be undesirable. The invention encompasses Fc constant domains comprising one or more amino acid modifications which alter antibody effector functions such as those disclosed in U.S. Patent Application Publication Nos. 2005/0037000 and 2005/0064514.

In some embodiments, the antibody of the invention contains both the light chain as well as at least the variable domain of a heavy chain. In other embodiments, the antibody of the invention may further comprise one or more of the CH1, hinge, CH2, CH3, and CH4 regions of the heavy chain. The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain may be of the $IgG_2$ class. The antibody of the invention may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, J. *Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions (see, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, *Nature* 332:323).

The antibodies of the present invention may be produced by any method known in the art useful for the production of polypeptides, e.g., in vitro synthesis, recombinant DNA production, and the like. Preferably, the humanized antibodies are produced by recombinant DNA technology. The antibodies of the invention may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

An exemplary process for the production of the recombinant chimeric antibodies of the invention may comprise the following: a) constructing, by conventional molecular biology methods, an expression vector that encodes and expresses an antibody heavy chain in which the CDRs and variable region of the murine anti-B7-H1 (or anti-PD-1)

monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-B7-H1 (or anti-PD-1) monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized antibodies of the invention may comprise the following: a) constructing, by conventional molecular biology methods, an expression vector that encodes and expresses an antibody heavy chain in which the CDRs and a minimal portion of the variable region framework that are required to retain donor antibody binding specificity are derived from a non-human immunoglobulin, such as the murine anti-B7-H1 (or anti-PD-1) monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the murine anti-B7-H1 (or anti-PD-1) monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant antibody of the invention may be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands). Furthermore, codon usage may by optimized when host cell is selected to account for species specific codon usage bias and enhance protein expression. For example, for CHO cell expression the DNA encoding the antibodies may incorporate codons used preferentially by *Cricetulus griseus* (from where Chinese Hamster ovaries cells are derived. Methods of codon optimization may be employed to facilitate improved expression by a desired host cell (see, e.g., Wohlgemuth, I. et al. (2011) *"Evolutionary Optimization Of Speed And Accuracy Of Decoding On The Ribosome,"* Philos. Trans. R. Soc. Lond. B Biol. Sci. 366(1580):2979-2986; Jestin, J. L. et al. (2009) *"Optimization Models And The Structure Of The Genetic Code,"* J. Mol. Evol. 69(5):452-457; Bollenbach, T. et al. (2007) *"Evolution And Multilevel Optimization Of The Genetic Code,"* Genome Res. 17(4):401-404; Kurland, C. G. et al. (1984) *"Optimization Of Translation Accuracy,"* Prog. Nucleic Acid Res. Mol. Biol. 31:191-219; Grosjean, H. et al. (1982) *"Preferential Codon Usage In Prokaryotic Genes: The Optimal Codon-Anticodon Interaction Energy And The Selective Codon Usage In Efficiently Expressed Genes,"* Gene 18(3): 199-209).

Any of the above-described antibodies can be used to generate anti-idiotype antibodies using techniques well known to those skilled in the art (see, e.g., Greenspan, N. S. et al. (1989) *"Idiotypes: Structure And Immunogenicity,"* FASEB J. 7:437-444; and Nisinoff, A. (1991) *"Idiotypes: Concepts And Applications,"* J. Immunol. 147(8):2429-2438).

The binding properties of any of the above antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman, U. et al. (1995) *"Phage Display Of Disulfide-Stabilized Fv Fragments,"* J. Immunol. Methods, 182:41-50, 1995; Ames, R. S. et al. (1995) *"Conversion Of Murine Fabs Isolated From A Combinatorial Phage Display Library To Full Length Immunoglobulins,"* J. Immunol. Methods, 184:177-186; Kettleborough, C. A. et al. (1994) *"Isolation Of Tumor Cell-Specific Single-Chain Fv From Immunized Mice Using Phage-Antibody Libraries And The Re-Construction Of Whole Antibodies From These Antibody Fragments,"* Eur. J. Immunol., 24:952-958, 1994; Persic, L. et al. (1997) *"An Integrated Vector System For The Eukaryotic Expression Of Antibodies Or Their Fragments After Selection From Phage Display Libraries,"* Gene, 187: 9-18; Burton, D. R. et al. (1994) *"Human Antibodies From Combinatorial Libraries,"* Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT Publication WO 92/22324; Mullinax, R. L. et al. (1992) "Expression Of A Heterodimeric Fab Antibody Protein In One Cloning Step," BioTechniques, 12(6):864-869; and Sawai et al. (1995) "Direct Production Of The Fab Fragment Derived From The Sperm Immobilizing Antibody Using Polymerase Chain Reaction And cDNA Expression Vectors," Am. J. Reprod. Immunol. 34:26-34; and Better, M. et al. (1988) "Escherichia coli Secretion Of An Active Chimeric Antibody Fragment," Science 240:1041-1043). Examples of techniques which can be used to produce single-chain Fvs and antibodies include those described in U.S. Pat. Nos. 4,946,778 and 5,258,498; Huston, J. S. et al. (1991) "Protein Engineering Of Single-Chain Fv Analogs And Fusion Proteins," Methods in Enzymology 203:46-88; Shu, L. et al., "Secretion Of A Single-Gene-Encoded Immunoglobulin From Myeloma Cells," Proc. Natl. Acad. Sci. (USA) 90:7995-7999; and Skerra. A. et al. (1988) "Assembly Of A Functional Immunoglobulin Fv Fragment In Escherichia coli," Science 240: 1038-1040.

Phage display technology can be used to increase the affinity of an antibody of the invention for B7-H1 and/or PD-1. This technique would be useful in obtaining high affinity antibodies that could be used in the combinatorial methods of the invention. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "Antibody Engineering By Codon-Based Mutagenesis In A Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "Stepwise In Vitro Affinity Maturation Of Vitaxin, An Alphav Beta3-Specific Humanized Mab," Proc. Natl. Acad. Sci. (USA) 95(11):6037-6042; Yelton, D. E. et al. (1995) "Affinity Maturation Of The BR96 Anti-Carcinoma Antibody By Codon-Based Mutagenesis," J. Immunol. 155:1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarity Determining Regions In The Center Of The Antibody Binding Site," J. Mol. Biol. 263:551-567).

The invention thus contemplates the use of random mutagenesis in concert with methods of phage display to identify improved CDRs and/or variable regions. Phage display technology can alternatively be used to increase (or decrease) CDR affinity by directed mutagenesis (e.g., affinity maturation or "CDR-walking"). This technique uses the target antigen or an antigenic fragment thereof to identify antibodies having CDRs that bind with higher (or lower) affinity to the antigen when compared with the initial or parental antibody (see, e.g., Glaser, S. M. et al. (1992) "Antibody Engineering By Codon-Based Mutagenesis In A Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased (or decreased) avidity to the antigen (e.g., ELISA) (see Wu, H. et al. (1998) "Stepwise In Vitro Affinity Maturation Of Vitaxin, An Alphav Beta3-Specific Humanized Mab," Proc. Natl. Acad. Sci. (USA) 95(11):6037-6042; Yelton, D. E. et al. (1995) "Affinity Maturation Of The BR96 Anti-Carcinoma Antibody By Codon-Based Mutagenesis," J. Immunol. 155:1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarily Determining Regions In The Center Of The Antibody Binding Site," J. Mol. Biol. 263:551-567).

Methods for accomplishing such affinity maturation are described for example in: Krause, J. C. et al. (2011) "An Insertion Mutation That Distorts Antibody Binding Site Architecture Enhances Function Of A Human Antibody," MBio. 2(1) pii: e00345-10. doi: 10.1128/mBio.00345-10; Kuan, C. T. et al. (2010) "Affinity-Matured Anti-Glycoprotein NMB Recombinant Immunotoxins Targeting Malignant Gliomas And Melanomas," Int. J. Cancer 10.1002/ijc.25645; Hackel, B. J. et al. (2010) "Stability And CDR Composition Biases Enrich Binder Functionality Landscapes," J. Mol. Biol. 401(1):84-96; Montgomery, D. L. et al. (2009) "Affinity Maturation And Characterization Of A Human Monoclonal Antibody Against HIV-1 gp41," MAbs 1(5):462-474; Gustchina, E. et al. (2009) "Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth," Virology 393(1):112-119; Finlay, W. J. et al. (2009) "Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions," J. Mol. Biol. 388(3):541-558; Bostrom, J. et al. (2009) "Improving Antibody Binding Affinity And Specificity For Therapeutic Development," Methods Mol. Biol. 525:353-376; Steidl, S. et al. (2008) "In Vitro Affinity Maturation Of Human GM-CSF Antibodies By Targeted CDR-Diversification," Mol. Immunol. 46(1):135-144; and Barderas, R. et al. (2008) "Affinity maturation of antibodies assisted by in silico modeling," Proc. Natl. Acad. Sci. (USA) 105(26):9029-9034.

The invention particularly contemplates the production and use of "derivatives" of any of the above-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. Such amino acids may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha (1 - - - 6) Dextran Increases Its Affinity For Antigen*," J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143(8): 2595-2601; Routledge, E. G. et al. (1995) "*The Effect Of Aglycosylation On The Immunogenicity Of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity*.," J. Biol. Chem. 277(30): 26733-26740).

In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Substitutions, additions or deletions in the derivatized antibodies may be in the Fc region of the antibody and may thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821. In some embodiments, the invention encompasses antibodies that have altered affinity for an activating FcγR, e.g., FcγRIIIA. Preferably such modifications also have an altered Fc-mediated effector function. Modifications that affect Fc-mediated effector function are well known in the art (see U.S. Pat. No. 6,194,551, and WO 00/42072). In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized antibodies of the invention may be engineered to increase biological half-lives (see, e.g. U.S. Pat. No. 6,277,375). For example, humanized antibodies of the invention may be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies of the invention may also be modified by the methods and coupling agents described by Davis et al. (See U.S. Pat. No. 4,179,337) in order to provide compositions that can be injected into the mammalian circulatory system with substantially no immunogenic response.

The invention encompasses modification of framework residues of the humanized antibodies of the invention. Framework residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "*Reshaping Human Antibodies For Therapy*," Nature 332: 323-327).

The present invention also encompasses anti-human B7-H1 and anti-human PD-1 antibodies (and more preferably, humanized antibodies) and antigen-binding fragments thereof that are recombinantly fused or chemically conjugated (including both covalently and non-covalently conjugations) to a heterologous molecule (i.e., an unrelated molecule). The fusion does not necessarily need to be direct, but may occur through linker sequences.

The Fc portion of the fusion the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "*Humanized Porcine VCAM-Specific Monoclonal Antibodies With Chimeric Igg2/G4 Constant Regions Block Human Leukocyte Binding To Porcine Endothelial Cells*," Mol. Immun. 34(6):441-452, Swann, P. G. (2008) "*Considerations For The Development Of Therapeutic Monoclonal Antibodies*," Curr. Opin. Immun. 20:493-499 (2008), and Presta, L. G. (2008) "*Molecular Engineering And Design Of Therapeutic Antibodies*," Curr. Opin. Immun. 20:460-470. In some embodiments the Fc region is the native IgG1, IgG2, or IgG4 Fc region. In some embodiments the Fc region is a hybrid, for example a chimeric consisting of IgG2/IgG4 Fc constant regions. Modications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduce binding to FcR which increase their half-life. Representative IG2-4 hybrids and IgG4 mutants are described in Angal, S. et al. (1993) "*A Single Amino Acid Substitution Abolishes The Heterogeneity Of Chimeric Mouse/Human (IgG4) Antibody*," Molec. Immunol. 30(1): 105-108; Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells*," Mol. Immun. 34(6):441-452; and U.S. Pat. No. 6,982,323. In some embodiments the IgG1 and/or IgG2 domain is deleted for example, Angal et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890. Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

In one embodiment such heterologous molecules are polypeptides having at least 10, at least 20, at least 30, at least 40, at least 50, at least 60, at least 70, at least 80, at least 90 or at least 100 amino acids. Such heterologous molecules may alternatively be enzymes, hormones, cell surface receptors, drug moieties, such as: toxins (such as abrin, ricin A, pseudomonas exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, monomethyl auristatin F (MMAF), monomethyl auristatin E (MMAE; e.g., vedotin) and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CON- TROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al. (1982) "*The Preparation And Cytotoxic Properties Of Antibody-Toxin Conjugates*," Immunol. Rev. 62:119-158; Carter, P. J. et al. (2008) "*Antibody-Drug Conjugates for Cancer Therapy*," Cancer J. 14(3):154-169; Alley, S. C. et al. (2010) "*Antibody-Drug Conjugates: Targeted Drug Delivery For Cancer*," Curr. Opin. Chem. Biol. 14(4):529-537; Carter, P. et al. (2005) "*Designer Antibody-Based Therapeutics For Oncology*," Amer. Assoc. Cancer Res. Educ. Book. 2005(1): 147-154; Carter, P. J. et al. (2008) "*Antibody-Drug Conjugates For Cancer Therapy*," Cancer J. 14(3):154-169; Chari, R. V. J. (2008) "*Targeted Cancer Therapy: Conferring Specificity To Cytotoxic Drugs*," Acc. Chem Res. 41(1):98-107; Doronina, S. O. et al. (2003) "*Development Of Potent Monoclonal Antibody Auristatin Conjugates For Cancer Therapy*," Nat. Biotechnol. 21(7):778-784; Ducry, L. et al. (2010) "*Antibody-Drug Conjugates: Linking Cytotoxic Payloads To Monoclonal Antibodies*," Bioconjug Chem. 21(1):5-13; Senter, P. D. (2009) "*Potent Antibody Drug Conjugates For Cancer Therapy*," Curr. Opin. Chem. Biol. 13(3):235-244; and Teicher, B. A. (2009) "*Antibody-Drug Conjugate Targets*," Curr Cancer Drug Targets. 9(8):982-1004.

Any of the molecules of the present invention can be fused to marker sequences, such as a peptide, to facilitate purification. In preferred embodiments, the marker amino acid sequence is a hexa-histidine peptide, the hemagglutinin "HA" tag, which corresponds to an epitope derived from the influenza hemagglutinin protein (Wilson, I. A. et al. (1984) "*The Structure Of An Antigenic Determinant In A Protein*," Cell, 37:767-778) and the "flag" tag (Knappik, A. et al. (1994) "*An Improved Affinity Tag Based On The FLAG Peptide For The Detection And Purification Of Recombinant Antibody Fragments*," Biotechniques 17(4):754-761).

The present invention also encompasses antibodies or their antigen-binding fragments that are conjugated to a diagnostic or therapeutic agent or any other molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

The molecules of the present invention can be conjugated to a second antibody to form an antibody heteroconjugate as described by Segal in U.S. Pat. No. 4,676,980. Such heteroconjugate antibodies may additionally bind to haptens (such as fluorescein, etc.), or to cellular markers (e.g., 4-1-BB, B7-H4, CD4, CD8, CD14, CD25, CD27, CD40, CD68, CD163, CTLA4, GITR, LAG-3, OX40, TIM3, TIM4, TLR2, LIGHT, ICOS, B7-H3, B7-H7, B7-H7CR, CD70, CD47, etc.) or to cytokines (e.g., IL-7, IL-15, IL-12, IL-4 TGF-beta, IL-10, IL-17, IFNγ, Flt3, BLys) or chemokines (e.g., CCL21), etc.

The molecules of the present invention may be attached to solid supports, which are particularly useful for immunoassays or purification of the target antigen or of other molecules that are capable of binding to target antigen that has been immobilized to the support via binding to an antibody or antigen-binding fragment of the present invention. Such solid supports include, but are not limited to, glass, cellulose, polyacrylamide, nylon, polystyrene, polyvinyl chloride or polypropylene.

The present invention additionally includes nucleic acid molecules (DNA or RNA) that encode any such antibodies, fusion proteins or fragments, as well as vector molecules (such as plasmids) that are capable of transmitting or of replication such nucleic acid molecules. The nucleic acids can be single-stranded, double-stranded, may contain both single-stranded and double-stranded portions.

A. Preferred Modulator Compositions of the Present Invention

The invention particularly concerns antibodies that immunospecifically bind to B7-H1 or to PD-1 and/or modulate the ability of B7-H1 to bind to PD-1 in a subject. As used herein, a "subject" is preferably a mammal such as a non-primate (e.g., cows, pigs, horses, cats, dogs, rats etc.) and a primate (e.g., monkey and human), most preferably a human. The invention thus particularly relates to humanized antibodies, and antigen-binding fragments thereof, that immunospecifically bind to human B7-H1 or to human PD-1 and modulate the ability of B7-H1 to bind to PD-1 in a human or in human tissue (in situ or ex vivo).

Most preferably, such antibodies and antigen-binding fragments will possess sufficient avidity to modulate the ability of B7-H1 (especially when expressed at an endogenous concentration and) arrayed on the surface of a subject's APC to bind to PD-1 (especially when expressed at an endogenous concentration and) arrayed on the surface of a T cell of such subject and vice versa. The term "endogenous concentration"

refers to the level at which an endogenous molecule is natively expressed (i.e., in the absence of expression vectors or recombinant promoters) in a normal, cancer or infected cell.

In one embodiment, such modulation will comprise inhibiting or otherwise interfering with the binding of such (preferably endogenously expressed and) arrayed B7-H1 and such (preferably endogenously expressed and) arrayed PD-1. In an alternative embodiment, such modulation will comprise an enhancement or otherwise facilitate the binding of endogenously expressed and arrayed B7-H1 and endogenously expressed and arrayed PD-1. In yet another embodiment, such modulation includes direct agonism whereby binding of the anti-B7-H1 or anti-PD-1 triggers signal transduction through the corresponding receptor.

(1) Preferred Anti-Human B7-H1 Antibodies and Their CDRs

In accordance with the present invention, such molecules can be produced by screening hybridoma lines for those that produce antibody that are immunospecific for human B7-H1, and then optionally screening amongst such lines for those exhibiting modulating activity (e.g., neutralizing activity, agonizing activity, altered signal transducing activity, etc.). The invention particularly provides anti-human B7-H1 clones: 1E12, 1F4, 2G11, 3B6, and 3D10.

The antibodies expressed by the anti-human B7-H1 clones were sequenced to reveal their variable domains. CDR sequences are shown in bold and underlined:

```
Anti-Human B7-H1 Clone 1E12
Light Chain Variable Region:
                                                        (SEQ ID NO: 1)
DIVMTQSHKL MSTSVGDRVS ITCKASQDVG TAVAWYQQKP GQSPKLLIYW

ASTRHTGVPD RFTGSGSGTD FTLTISNVQS EDLADYFCQQ DSSYPLTFGA

GTKVELK

Heavy Chain Variable Region:
                                                        (SEQ ID NO: 2)
EVKLQESGPS LVKPSQTLSL TCSVTGYSIT SDYWNWIRKF PGNKLEYVGY

ISYTGSTYYN PSLKSRISIT RDTSKNQYYL QLNSVTSEDT ATYYCARYGG

WLSPFDYWGQ GTTLTVSS

Anti-Human B7-H1 Clone 1F4
Light Chain Variable Region:
                                                        (SEQ ID NO: 3)
DIVTTQSHKL MSTSVGDRVS ITCKASQDVG TAVAWYQQKP GQSPKLLIYW

ASTRHTGVPD RFTGSGSGTD FTLTISNVQS EDLADYFCQQ DSSYPLTFGA

GTKVELK

Heavy Chain Variable Region:
                                                        (SEQ ID NO: 4)
EVQLQESGPG LVAPSQSLSI TCTVSGFSLT TYSINWIRQP PGKGLEWLGV

MWAGGGTNSN SVLKSRLIIS KDNSKSQVFL KMNSLQTDDT ARYYCARYYG

NSPYYAIDYW GQGTSVTVSS

Anti-Human B7-H1 Clone 2G11
Light Chain Variable Region:
                                                        (SEQ ID NO: 5)
DIVMTQSPSS LAVSVGEKVS MGCKSSQSLL YSSNQKNSLA WYQQKPGQSP

KLLIDWASTR ESGVPDRFTG SGSGTDFTLT ISSVKAEDLA VYYCQQYYGY

PLTFGAGTKL ELK

Heavy Chain Variable Region:
                                                        (SEQ ID NO: 6)
EVKLQESGPS LVKPSQTLSL TCSVTGYSII SDYWNWIRKF PGNKLEYLGY

ISYTGSTYYN PSLKSRISIT RDTSKNQYYL QLNSVTTEDT ATYYCARRGG

WLLPFDYWGQ GTTLTVSS
```

Anti-Human B7-H1 Clone 3B6
Light Chain Variable Region:
(SEQ ID NO: 7)
DIVMTQSPAI MSASPGEKVT MTCSASSSIR YMHWYQQKPG TSPKRWISDT

SKLTSGVPAR FSGSGSGTSY ALTISSMEAE DAATYYCHQR SSYPWTFGGG

TKLEIK

Heavy Chain Variable Region:
(SEQ ID NO: 8)
EVKLQESGPS LVKPGASVKL SCKASGYTFT SYDINWVKQR PGQGLEWIGW

IFPRDNNTKY NENFKGKATL TVDTSSTTAY MELHSLTSED SAVYFCTKEN

WVGDFDYWGQ GTTLTLSS

Anti-Human B7-H1 Clone 3D10:
Light Chain Variable Region:
(SEQ ID NO: 9)
QIVLSQSPAI LSASPGEKVT MTCRASSSVS YIYWFQQKPG SSPKPWIYAT

FNLASGVPAR FSGSGSGTSY SLTISRVETE DAATYYCQQW SNNPLTFGAG

TKLELK

Heavy Chain Variable Region:
(SEQ ID NO: 10)
EVQLQQSGPD LVTPGASVRI SCQASGYTFP DYYMNWVKQS HGKSLEWIGD

IDPNYGGTTY NQKFKGKAIL TVDRSSTAY MELRSLTSED SAVYYCARGA

LTDWGQGTSL TVSS (2) Preferred Anti-Human PD-1 Antibodies and Their CDRs

Alternatively such antibodies can be produced by screening hybridoma lines for those that produce antibody that are immunospecific for human PD-1, and then screening amongst such lines for those exhibiting modulating activity (e.g., neutralizing activity, agonizing activity, altered signal transducing activity, etc.). The invention particularly provides anti-human PD-1 clones: 1E3, 1E8, and 1H3.

The antibodies expressed by the anti-human PD-1 clones were sequenced to reveal their variable domains. CDR sequences are shown in bold and underlined:

Anti-Human PD-1 Clone 1E3:
Light Chain Variable Region:
(SEQ ID NO: 11)
DIQMTQFPSS LCASQGGKVT VTCKASQDIN NYMAWYQHKP GKGPRLLIHY

TSTLLSGIPS RFSGSGSGRD YSFSISNLEP EDIATYYCLQ YDNLWTFGGG

TKLEIK

Heavy Chain Variable Region:
(SEQ ID NO: 12)
EVQLQQSGPV LVKPGASVKM SCKASGYTFT DYYMNWVKQS HGKSLEWIGN

INPYNGGTTY NQKFKGKATL TVDKSSRTAY MEINSLTSED SAVYYCARGR

IYDGSLDYWG QGTALTVSS

Anti-Human PD-1 Clone 1E8:
Light Chain Variable Region:
(SEQ ID NO: 13)
DIVMTQSQKF MSTSVGDRVS VTCKASQSVD TNVAWYQQKP GQSPKALIFS

ASYRYSGVPD RFTGSGSGTD FTLTINSVQS EDLAEYFCQQ YNSYPYTFGS

GTKLEIK

Heavy Chain Variable Region:
(SEQ ID NO: 14)
QVQLQQSGAE LAKPGASVRL SCKASGYTFT NYWMHWVKQR PGQGLEWIGH

INPSSGFTTY NQNFKDKATL TADKSSNTAY MQLSSLTYED SAVYFCARED

YDVDYWGQGT TLTVSS

Anti-Human PD-1 Clone 1H3:

Light Chain Variable Region:

(SEQ ID NO: 15)

QIVLTQSPAL MSASPGEKVT MTCSASSSVS YMYWYQQKPR SSPKPWIYLT

SNLASGVPAR FSGSGSGTSY SLTISSMEAE DAATYYCQQW SSNPFTFGSG

TKLEIK

Heavy Chain Variable Region:

(SEQ ID NO: 16)

EVQLVESGGG LVKPGGSLKL SCAASGFTFS DYGMHWVRQA PEKGLEWVAY

ISSGSYTIYY TDTVKGRFTI SRDNAKNTLF LQMTSLRSED TAMYYCARRG

YGSFYEYYFD YWGQGTTLTV SS (3) Consensus CDRs of the Anti-Human B7-H1 and Anti-Human PD-1 Antibodies of the Present Invention Analyses of the CDRs of the identified antibodies were conducted in order to identify consensus CDR sequences and likely variant CDR sequences that would provide similar binding attributes. Such variant CDRs were computed using Blosum62.iij analysis according to Table 1. Table 1 presents the Blosum62.iij substitution scores. The higher the score the more conservative the substitution and thus the more likely the substitution will not affect function.

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The present invention permits the formation of novel antibodies and antigen-binding fragments having 1, 2, 3, 4, 5 or 6 variant CDRs. Because the methods of the present invention have identified a substantial number of distinct CDRs, the invention permits a recognition of CDR residues that are likely to be required in any variant of a particular identified CDR. Such residues are shown in boldface in Table 2, Table 3, Table 4 and Table 5. For those residues that are found to vary among the compared CDRs, the substitution scores of Table 1 provide a means for determining the identities of permitted substitutions. For example, if a particular residue of a particular CDR is found to vary as R or S, then since R and S have a substitution score of −1, any substitution for R or S having a substitution score of −1 or greater are as likely as the observed variants (R or S) (or are more likely than R or S) to create a variant CDR having binding attributes that are sufficiently similar to those of the particular CDR to permit the variant CDR to be employed in lieu thereof so as to form a functional anti-B7-H1 or anti-PD-1 antibody or antigen-binding fragment. For each position, the selection of a residue having a higher substitution score is preferred over the selection of a residue having a lower substitution score.

Table 2 presents an analysis of the light chain CDRs of the anti-B7-H1 antibodies and provides the consensus sequence of the observed and preferred variant light chain anti-B7-H1 CDRs of the present invention.

TABLE 2

Anti-Human B7-H1 Light Chain CDRs

Light Chain CDR1

| Antibody | Sequence | | | | | | | | | | | SEQ ID NO |
|---|---|---|---|---|---|---|---|---|---|---|---|---|
| 3D10 | R | A | S | S | | S | V | S | Y | I | Y | 17 |
| 3B6 | S | A | S | S | | S | I | R | Y | M | H | 18 |
| 1E12 | K | A | S | Q | | D | V | G | T | A | V | 19 |
| 2G11 | K | S | S | Q | SLLYSS | N | Q | K | N | S | L | A | 20 |
| 1F4 | K | A | S | Q | | D | V | G | T | A | V | A | 21 |
| Light Chain CDR1 Consensus Sequence: | X1 | X2 | S | X3 | X4 | X5 | X6 | X7 | X8 | X9 | X10 | X11 | 22 |

X1 are substitutions of R/K/S or substitutions having an equal or greater substitution score (i.e., ≥+2): R, S or K
X2 are substitutions of A/S or substitutions having an equal or greater substitution score (i.e., ≥+1): A or S
X3 are substitutions of Q/S or substitutions having an equal or greater substitution score (i.e., ≥0): R, N, D, Q, E, H, K, M, or S
X4 is SLLYSS (SEQ ID NO: 23) or is absent
X5 is absent or substitutions of D/N or substitutions having an equal or greater substitution score (i.e., ≥+1): N or D
X6 are substitutions of S/V/Q or substitutions having an equal or greater substitution score (i.e., ≥0): A, Q, E, L, K, M, P, S, T, Y, or V
X7 are substitutions of V/I/G/K or substitutions having an equal or greater substitution score (i.e., ≥−4): Any Amino Acid
X8 are substitutions of S/R/T/N or substitutions having an equal or greater substitution score (i.e., ≥0): R, N, S, or T
X9 are substitutions of Y/A/S or substitutions having an equal or greater substitution score (i.e., ≥−2): A, R, N, C, Q, E, H, I, L, K, M, F, S, T, Y, or V
X10 are substitutions of I/M/L/V or substitutions having an equal or greater substitution score (i.e., ≥+1): I, L, M, or V
X11 are substitutions of Y/A/H or substitutions having an equal or greater substitution score (i.e., ≥−2): A, R, N, Q, E, H, I, K, M, F, S, T, or Y Light Chain CDR2

| Antibody | Sequence | | | | | | | SEQ ID NO |
|---|---|---|---|---|---|---|---|---|
| 3D10 | A | T | F | N | L | A | S | 24 |
| 3B6 | D | T | S | K | L | T | S | 25 |
| 1E12 | W | A | S | T | R | H | T | 26 |
| 2G11 | W | A | S | T | R | E | S | 27 |

TABLE 2 -continued

Anti-Human B7-H1 Light Chain CDRs

| | | | | | | | | | SEQ ID NO |
|---|---|---|---|---|---|---|---|---|---|
| 1F4 | | W | A | S | T | R | H | T | 28 |
| Light Chain CDR2 Consensus Sequence: | | X1 | X2 X3 | X4 | X5 | X6 | | X7 | 29 |

X1 are substitutions of A/D/W or substitutions having an equal or greater substitution score (i.e., ≥-4): Any Amino Acid
X2 are substitutions of T/A or substitutions having an equal or greater substitution score (i.e., ≥0): A, C, G, S, T, or V
X3 are substitutions of F/S or substitutions having an equal or greater substitution score (i.e., ≥-2): A, C, H, I, L, M, F, S, T, Y, or V
X4 are substitutions of N/K/T or substitutions having an equal or greater substitution score (i.e., ≥-1): R, N, D, Q, E, K, S, or T
X5 are substitutions of L/R or substitutions having an equal or greater substitution score (i.e., ≥-2): A, R, Q, L, K, M, S, T, or Y
X6 are substitutions of A/T/H/E or substitutions having an equal or greater substitution score (i.e., ≥-2): A, R, N, D, Q, E, G, H, K, M, F, P, S, T, or Y
X7 are substitutions of S/T or substitutions having an equal or greater substitution score (i.e., ≥+1): A, N, S, or T

Light Chain CDR3

| Antibody | | | | | Sequence | | | | | SEQ ID NO |
|---|---|---|---|---|---|---|---|---|---|---|
| 3D10 | Q | Q | W | S | N | N | P | L | T | 30 |
| 3B6 | H | Q | R | S | S | Y | P | W | T | 31 |
| 1E12 | Q | Q | D | S | S | Y | P | L | T | 32 |
| 2G11 | Q | Q | Y | Y | G | Y | P | L | T | 33 |
| 1F4 | Q | Q | D | S | S | Y | P | L | T | 34 |
| Light Chain CDR3 Consensus Sequence: | X1 | Q | X2 | X3 | X4 | X5 | P | X6 | T | 35 |

X1 are substitutions of Q/H or substitutions having an equal or greater substitution score (i.e., ≥0): R, N, Q, E, or H
X2 are substitutions of W/R/D/Y or substitutions having an equal or greater substitution score (i.e., ≥-4): Any Amino Acid
X3 are substitutions of S/Y or substitutions having an equal or greater substitution score (i.e., ≥-2): A, R, N, C, Q, E, H, I, L, K, M, F, S, T, Y, or V
X4 are substitutions of N/S/G or substitutions having an equal or greater substitution score (i.e., ≥0): N, G, or S
X5 are substitutions of N/Y or substitutions having an equal or greater substitution score (i.e., ≥0): A, R, N, D, C, Q, E, G, H, I, L, K, M, F, P, S, T, W, Y, or V
X6 are substitutions of K/S or substitutions having an equal or greater substitution score (i.e., ≥-2): A, R, N, D, Q, E, G, H, K, M, P, S, T, or Y Table 3 presents an analysis of the heavy chain CDRs of the anti-B7-H1 antibodies and provides the consensus sequence of the observed and preferred variant anti-B7-H1 heavy chain CDRs of the present invention.

TABLE 3

Anti-Human B7-H1 Heavy Chain CDRs

Heavy Chain CDR1

| Antibody | | | | | Sequence | | | | | SEQ ID NO |
|---|---|---|---|---|---|---|---|---|---|---|
| 3D10 | G | Y | T | F | P | D | Y | Y | M | N | 36 |
| 3B6 | G | Y | T | F | T | S | Y | D | I | N | 37 |
| 1E12 | G | Y | S | I | T | S | D | Y | W | N | 38 |
| 2G11 | G | Y | S | I | I | S | D | Y | W | N | 39 |
| 1F4 | G | F | S | L | T | T | Y | S | I | N | 40 |

TABLE 3 -continued

Anti-Human B7-H1 Heavy Chain CDRs

| Heavy Chain CDR1 Consensus Sequence: | G | X1 | X2 | X3 | X4 | X5 | X6 | X7 | X8 | N | 41 |
|---|---|---|---|---|---|---|---|---|---|---|---|

X1 are substitutions of Y/F or substitutions having an equal or greater substitution score (i.e., ≥+3): Y or F
X2 are substitutions of T/S or substitutions having an equal or greater substitution score (i.e., ≥+1): T or S
X3 are substitutions of F/I/L or substitutions having an equal or greater substitution score (i.e., ≥0): I, L, M, or F
X4 are substitutions of P/T/I or substitutions having an equal or greater substitution score (i.e., ≥-3): A, R, N, D, C, Q, E, H, I, L, K, M, P, S, T, W, Y, or V
X5 are substitutions of D/S/T or substitutions having an equal or greater substitution score (i.e., ≥-1): N, D, Q, E, K, P, S, or T
X6 are substitutions of Y/D or substitutions having an equal or greater substitution score (i.e., ≥-3): A, R, N, D, C, Q, E, G, H, I, L, K, M, F, P, S, T, Y, or V
X7 are substitutions of Y/D/S or substitutions having an equal or greater substitution score (i.e., ≥0): A, R, N, D, C, Q, E, G, H, I, L, K, M, F, P, S, T, Y, or V
X8 are substitutions of M/I/W or substitutions having an equal or greater substitution score (i.e., ≥-3): A, R, C, Q, E, H, I, L, K, M, F, S, T, W, Y, or V Heavy Chain CDR2

| Antibody | Sequence | | | | | | | | | | | | | | | SEQ ID NO |
|---|---|---|---|---|---|---|---|---|---|---|---|---|---|---|---|---|
| 3D10 | D | I | D | P | N | Y | G | G | T | T | Y | N | Q | K | F | K | G | 42 |
| 3B6 | W | I | F | P | R | D | N | N | T | K | Y | N | E | N | F | K | G | 43 |
| 1E12 | Y | I | S |   | Y | T | G | S | T | Y | Y | N | P | S | L | K | S | 44 |
| 2G11 | Y | I | S |   | Y | T | G | S | T | Y | Y | N | P | S | L | K | S | 45 |
| 1F4 | V | M | W |   | A | G | G | G | T | N | S | N | S | V | L | K | S | 46 |
| Heavy Chain CDR2 Consensus Sequence: | X1 | X2 | X3 | X4 | X5 | X6 | X7 | X8 | T | X9 | X10 | N | X11 | X12 | X13 | K | X14 | 47 |

X1 are substitutions of D/W/Y/V or substitutions having an equal or greater substitution score (i.e., ≥-4): Any Amino acid
X2 are substitutions of I/M or substitutions having an equal or greater substitution score (i.e., ≥+1): I, L, M, F, or V
X3 are substitutions of D/F/S/W or substitutions having an equal or greater substitution score (i.e., ≥-4): Any Amino Acid
X4 is P or absent
X5 are substitutions of N/R/Y/A or substitutions having an equal or greater substitution score (i.e., ≥-2): A, R, N, Q, E, H, K, M, S, T, Y, or V
X6 are substitutions of Y/D/T/G or substitutions having an equal or greater substitution score (i.e., ≥-3): A, R, N, D, C, Q, E, G, H, K, M, F, P, S, T, Y, or V
X7 are substitutions of N/G or substitutions having an equal or greater substitution score (i.e., ≥0): N, G, or S
X8 are substitutions of N/G/S or substitutions having an equal or greater substitution score (i.e., ≥0): N, G, or S
X9 are substitutions of K/T/Y/N or substitutions having an equal or greater substitution score (i.e., ≥-2): A, R, N, Q, E, H, K, M, S, T, or Y
X10 are substitutions of Y/S or substitutions having an equal or greater substitution score (i.e., ≥-2): A, R, N, C, Q, E, H, I, L, K, M, F, S, T, W, Y, or V
X11 are substitutions of Q/E/P/S or substitutions having an equal or greater substitution score (i.e., ≥-1): A, D, Q, E, K, P, S, or T
X12 are substitutions of K/N/S/V or substitutions having an equal or greater substitution score (i.e., ≥-3): A, R, N, D, C, Q, E, G, H, I, L, K, M, P, S, T, Y, or V
X13 are substitutions of F/L or substitutions having an equal or greater substitution score (i.e., ≥0): I, L, M, or F
X14 are substitutions of G/S or substitutions having an equal or greater substitution score (i.e., ≥0): A, G, or S TABLE 3 -continued Anti-Human B7-H1 Heavy Chain CDRs Heavy Chain CDR3

| Antibody | Sequence | | | | | | | | | SEQ ID NO |
|---|---|---|---|---|---|---|---|---|---|---|
| 3D10 | | | G | A | L | | | | | 48 |
| 3B6 | | E | N | W | V | G | D | F | | 49 |
| 1E12 | Y | G | G | W | L | S | P | F | | 50 |
| 2G11 | R | G | G | W | L | L | P | F | | 51 |
| 1F4 | Y | Y | G | N | S | P | Y | Y | AI | 52 |
| Heavy Chain CDR3 Consensus Sequence: | X1 | X2 | X3 | X4 | X5 | X6 | X7 | X8 | X9 | 53 |

X1 are substitutions of E/Y/R or substitutions having an equal or greater substitution score (i.e., ≥-2): A, R, N, Q, E, H, K, M, S, T, or Y
X2 are substitutions of N/G/Y or substitutions having an equal or greater substitution score (i.e., ≥-3): A, R, N, D, C, Q, E, G, H, K, M, F, P, S, T, Y, or V
X3 are substitutions of G/W or substitutions having an equal or greater substitution score (i.e., ≥-2): Q, G, H, T, or W
X4 are substitutions of A/V/W/N or substitutions having an equal or greater substitution score (i.e., ≥-4): Any Amino Acid
X5 are substitutions of L/G/S or substitutions having an equal or greater substitution score (i.e., ≥-4): Any Amino Acid
X6 are substitutions of D/S/L/P or substitutions having an equal or greater substitution score (i.e., ≥-4): Any Amino Acid
X7 are substitutions of F/P/Y or substitutions having an equal or greater substitution score (i.e., ≥-4): Any Amino Acid
X8 are substitutions of F/Y or substitutions having an equal or greater substitution score (i.e., ≥+3): F or Y
X9 is AI or absent Thus, in addition to antibodies and antigen-binding fragments thereof that possess the CDRs of the anti-B7-H1 antibodies: 1E12, 1F4, 2G11, 3B6, and 3D10, the invention additionally provides antibodies and antigen-binding fragments thereof that possess CDRs having the above-described light and/or heavy chain consensus sequences.

Table 4 presents an analysis of the light chain CDRs of the anti-PD-1 antibodies and provides the consensus sequence of the observed and preferred variant light chain anti-PD-1 CDRs of the present invention.

TABLE 4

Anti-Human PD-1 Light Chain CDRs

Light Chain CDR1

| Antibody | Sequence | | | | | | | | | | SEQ ID NO |
|---|---|---|---|---|---|---|---|---|---|---|---|
| 1H3 | S | A | S | S | | S | V | S | Y | M | Y | 54 |
| 1E3 | K | A | S | Q | D | I | N | N | Y | M | A | 55 |
| 1E8 | K | A | S | Q | S | V | D | T | N | V | A | 56 |
| Light Chain CDR1 Consensus Sequence: | X1 | A | S | X2 | X3 | X4 | X5 | X6 | X7 | X8 | X9 | 57 |

X1 are substitutions of K/S or substitutions having an equal or greater substitution score (i.e., ≥0): N, Q, E, K, or S
X2 are substitutions of S/Q or substitutions having an equal or greater substitution score (i.e., ≥0): N, D, Q, E, K, or S
X3 is absent or are substitutions of D/S or substitutions having an equal or greater substitution score (i.e., ≥0): N, D, Q, E, or S
X4 are substitutions of S/I/V or substitutions having an equal or greater substitution score (i.e., ≥-2): A, C, I, L, M, F, S, T, Y, or V
X5 are substitutions of V/N/D or substitutions having an equal or greater substitution score (i.e., ≥-3): A, R, N, D, C, Q, E, G, H, I, K, M, F, P, S, T, Y, or V
X6 are substitutions of S/N/T or substitutions having an equal or greater substitution score (i.e., ≥0): N, S, or T TABLE 4 -continued Anti-Human PD-1 Light Chain CDRs X7 are substitutions of Y/N or substitutions having an equal or greater
substitution score (i.e., ≥-2): A, R, N, D, Q, E, G, H, K, M, P, S, T, or Y
X8 are substitutions of M/N or substitutions having an equal or greater
substitution score (i.e., ≥+1): I, L, M, or V
X9 are substitutions of Y/A or substitutions having an equal or greater
substitution score (i.e., ≥-2): A, R, N, C, Q, E, H, I, L, K, M, F, S, T,
Y, or V Light Chain CDR2

| Antibody | Sequence | | | | | | SEQ ID NO |
|---|---|---|---|---|---|---|---|
| 1H3 | L | T | S | N | L | A | S | 58 |
| 1E3 | Y | T | S | T | L | L | S | 59 |
| 1E8 | S | A | S | Y | R | Y | S | 60 |
| Light Chain CDR2 Consensus Sequence: | X1 | X2 | S | X3 | X4 | X5 | S | 61 |

X1 are substitutions of L/Y/S or substitutions having an equal or greater
substitution score (i.e., ≥-2): A, R, C, Q, I, L, K, M, F, S, T, Y, or V
X2 are substitutions of T/A or substitutions having an equal or greater
substitution score (i.e., ≥0): A, S, T, or V
X3 are substitutions of N/T/Y or substitutions having an equal or greater
substitution score (i.e., ≥2): A, R, N, Q, E, H, K, M, S, T, or Y
X4 are substitutions of L/R or substitutions having an equal or greater
substitution score (i.e., ≥-2): A, R, N, Q, L, K, M, S, T, or Y
X5 are substitutions of A/L/Y or substitutions having an equal or greater
substitution score (i.e., ≥-2): A, R, C, Q, I, L, K, M, F, S, T, Y, or V Light Chain CDR3

| Antibody | Sequence | | | | | | | | SEQ ID NO |
|---|---|---|---|---|---|---|---|---|---|
| 1H3 | Q | Q | W | S | S | N | P | F | T | 62 |
| 1E3 | L | Q | Y | D | N | L |   | W | T | 63 |
| 1E8 | Q | Q | Y | N | S | Y |   | P | T | 64 |
| Light Chain CDR3 Consensus Sequence: | X1 | Q | X2 | X3 | X4 | X5 | X6 | X7 | T | 65 |

X1 are substitutions of Q/L or substitutions having an equal or greater
substitution score (i.e., ≥-2): A, R, N, Q, L, K, M, S, T, W, Y, or V
X2 are substitutions of W/Y or substitutions having an equal or greater
substitution score (i.e., ≥+2): W or Y
X3 are substitutions of S/D/N or substitutions having an equal or greater
substitution score (i.e., ≥0): N, D, Q, E, or S
X4 are substitutions of S/N or substitutions having an equal or greater
substitution score (i.e., ≥+1): N, S, or T
X5 are substitutions of N/L/Y or substitutions having an equal or greater
substitution score (i.e., ≥-3): A, R, N, C, Q, E, H, I, L, K, M, F, P,
S, T, Y, or V
X6 is absent or P
X7 are substitutions of F/W/Y or substitutions having an equal or greater
substitution score (i.e., ≥+1): F, W, or Y Table 5 presents an analysis of the heavy chain CDRs of the anti-PD-1 antibodies and provides the consensus sequence of the observed and preferred variant anti-PD-1 heavy chain CDRs of the present invention.

TABLE 5

Anti-Human PD-1 Heavy Chain CDRs

Heavy Chain CDR1

| Antibody | Sequence | | | | | | | | | SEQ ID NO |
|---|---|---|---|---|---|---|---|---|---|---|
| 1H3 | G | F | T | F | S | D | Y | G | M | H | 66 |
| 1E3 | G | Y | T | F | T | D | Y | Y | M | N | 67 |
| 1E8 | G | Y | T | F | T | N | Y | W | M | H | 68 |
| Heavy Chain CDR1 Consensus Sequence: | G | X1 | T | F | X2 | X3 | Y | X4 | M | X5 | 69 |

TABLE 5 -continued

Anti-Human PD-1 Heavy Chain CDRs

X1 are substitutions of F/Y or substitutions having an equal or greater substitution score (i.e., ≥+3): F or Y
X2 are substitutions of S/T or substitutions having an equal or greater substitution score (i.e., ≥+1): S or T
X3 are substitutions of D/N or substitutions having an equal or greater substitution score (i.e., ≥+1): N or D
X4 are substitutions of G/Y/W or substitutions having an equal or greater substitution score (i.e., ≥-3): A, R, C, Q, E, G, H, K, M, F, S, T, W, Y, or V
X5 are substitutions of H/N or substitutions having an equal or greater substitution score (i.e., ≥+1): N or H Heavy Chain CDR2

| Antibody | Sequence | SEQ ID NO |
|---|---|---|
| 1H3 | Y I S S G S Y T I Y Y T D T V K G | 70 |
| 1E3 | N I N P Y N G T T Y N Q K F K G | 71 |
| 1E8 | H I N P S S G T T Y N Q N F K D | 72 |
| Heavy Chain CDR2 Consensus Sequence: | x1 I X2 X3 X4 X5 X6 X7 X8 X9 Y X10 X11 X12 X13 K X14 | 73 |

X1 are substitutions of Y/N/H or substitutions having an equal or greater substitution score (i.e., ≥-2): A, R, N, Q, E, H, K, M, S, T, or Y
X2 are substitutions of S/N or substitutions having an equal or greater substitution score (i.e., ≥+1): N or S
X3 are substitutions of S/P or substitutions having an equal or greater substitution score (i.e., ≥-1): A, D, Q, E, K, P, S, or T
X4 are substitutions of G/Y/S or substitutions having an equal or greater substitution score (i.e., ≥-3): A, R, N, D, C, Q, E, G, H, K, M, F, P, S, T, W, Y, or V
X5 are substitutions of S/N or substitutions having an equal or greater substitution score (i.e., >0): N or S
X6 are substitutions of Y/G or substitutions having an equal or greater substitution score (i.e., ≥-3): A, R, N, D, C, Q, E, G, H, K, M, F, P, S, T, W, Y, or V
X7 are substitutions of T/G/F or substitutions having an equal or greater substitution score (i.e., ≥-3): A, R, N, D, C, Q, E, G, H, K, M, F, S, T, W, Y, or V
X8 are substitutions of I/T or substitutions having an equal or greater substitution score (i.e., ≥-1): A, C, I, L, M, T, or V
X9 are substitutions of Y/T or substitutions having an equal or greater substitution score (i.e., ≥-2): A, R, N, C, Q, E, H, I, L, K, M, F, S, T, W, Y, or V
X10 are substitutions of T/N or substitutions having an equal or greater substitution score (i.e., ≥0): N, S, or T
X11 are substitutions of D/Q or substitutions having an equal or greater substitution score (i.e., ≥0): N, D, Q, E, or S
X12 are substitutions of T/K/N or substitutions having an equal or greater substitution score (i.e., ≥-1): R, N, D, Q, E, K, S, or T
X13 are substitutions of V/F or substitutions having an equal or greater substitution score (i.e., ≥-1): I, L, M, W, Y, or V
X14 are substitutions of G/D or substitutions having an equal or greater substitution score (i.e., ≥-1): N, D, G, or S Heavy Chain CDR3

| Antibody | Sequence | SEQ ID NO |
|---|---|---|
| 1H3 | R G Y G S F Y E YYF D Y | 74 |
| 1E3 | G R I Y D G S L D Y | 75 |
| 1E8 | E D Y D V D Y | 76 |
| Heavy Chain CDR3 Consensus Sequence: | X1 X2 X3 X4 X5 X6 X7 X8 X9 D Y | 77 |

X1 are substitutions of R/G/E or substitutions having an equal or greater substitution score (i.e., ≥-2): A, R, N, D, Q, E, G, H, K, P, S, or T
X2 are substitutions of G/R/D or substitutions having an equal or greater substitution score (i.e., ≥-2): A, R, N, D, Q, E, G, H, K, P, S, or T
X3 are substitutions of Y/I or substitutions having an equal or greater substitution score (i.e., ≥-1): I, L, M, F, Y, or V
X4 are substitutions of Y/G/D or substitutions having an equal or greater substitution score (i.e., ≥-3): A, R, N, D, C, Q, E, G, H, K, M, F, P, S, T, W, Y, or V TABLE 5 -continued Anti-Human PD-1 Heavy Chain CDRs

```
X5 are substitutions of S/D/V or substitutions having an equal or greater substitution
score (i.e., ≥-3): A, R, N, D, C, Q, E, G, H, I, K, M, F, P,
S, T, Y, or V
X6 is absent or are substitutions of F/G or substitutions having an equal or greater
substitution score (i.e., ≥-3): A, R, N, D, C, Q, E, G, H, K, M, F, S, T, W, Y, or V
X7 is absent or are substitutions of Y/S or substitutions having an equal or greater
substitution score (i.e., ≥-2): A, R, N, C, Q, E, H, I, L, K, M, F, S, T, Y, or V
X8 is absent or are substitutions of E/L or substitutions having an equal or greater
substitution score (i.e., ≥-3): A, R, N, Q, E, H, I, L, K, M, F, P, S, T, W, Y, or V
X9 is absent or is YYF
```

Thus, in addition to antibodies and antigen-binding fragments thereof that possess the CDRs of the anti-PD-1 antibodies: 1E3, 1E8, and 1H3, the invention additionally provides antibodies and antigen-binding fragments thereof that possess CDRs having the above-described light and/or heavy chain consensus sequences.

The present invention encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by any of the above clones, and which exhibit immunospecific binding to B7-H1 or PD-1. The present invention further encompasses antibodies or fragments thereof that comprise a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the above-listed clones and which exhibit immunospecific binding to B7-H1 or PD-1. The determination of percent identity of two amino acid sequences can be determined by BLAST protein comparison.

In a specific embodiment, an antibody or an antigen-binding fragment thereof of the present invention will comprise one, two, three, four, five, or more preferably, all six of the CDRs of the above-described preferred antibodies and will exhibit the ability to bind to human B7-H1 or PD-1.

B. Therapeutic and Prophylactic Uses of the Preferred Compositions of the Present Invention The invention particularly relates to the therapeutic and/or prophylactic use of molecules (especially antibodies or their antigen-binding fragments) that immunospecifically bind human B7-H1 or human PD-1, and/or that are capable of modulating the binding between B7-H1 and PD-1 as such molecules (B7-H1 or PD-1) are endogenously expressed and arrayed in a subject (e.g., a human patient) and/or are capable of modulating signaling via PD-1 or B7-H1.

As used herein, the terms "treat," "treating," "treatment" and "therapeutic use" refer to the elimination, reduction or amelioration of one or more symptoms of a disease or disorder exacerbated by the interactions of B7-H1 and PD-1. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ ed., 2002).

1. Uses of Up-Modulators of the Immune System

In a preferred embodiment, such antibodies and fragments bind to these antigens at one or more sites to B7-H1 or PD-1 proximal to and disruptive of the B7-H1-PD-1 binding site. As discussed above, interactions between PD-1 and B7-H1 inhibit the proliferation of T cells and reduce the production of multiple cytokines (see, Sharpe, A. H. et al. (2002) "*The B7-CD28 Superfamily*," Nature Rev. Immunol. 2:116-126). Thus, in a preferred embodiment, the administration of the molecules of the present invention to a subject up-modulates the immune system of the subject by antagonizing B7-H1-PD-1 binding. In another embodiment, the avidity and/or affinity of the anti-PD-1 antibody may be such that it only binds to (and blocks B7-H1 binding to) T cells that express very high levels of PD-1, which are the exhausted or dysfunctional T cells, and thus allow specific targeting of this cell population. Thus, the invention relates to the use of the antibodies of the present invention to mediate increased production of IFN-γ. Thus, it relates to the use of such antibodies in the treatment of diseases and conditions that are treatable with IFN-γ, such as ovarian and other forms of cancer, chronic granulomatous disease, osteopetrosis, Friedreich's ataxia, etc. Additionally, the invention particularly relates to the use of the antibodies of the present invention to mediate increased T cell proliferation. Thus, it relates to the use of such antibodies in the treatment of diseases and conditions that are treatable by increasing T cell proliferation, such as: AIDS; severe combined immunodeficiency (SCID); Omenn syndrome; Cartilage-hair hypoplasia; T cell loss or ablation incident to organ or tissue transplantation or chemotherapy; hypogammaglobulinemia; X-linked agammaglobulinemia; Transient hypogammaglobulinemia; dysgammaglobulinemia; IgA deficiency •IgG deficiency; •IgM deficiency; •hyper IgM syndrome; •Wiskott-Aldrich syndrome; •hyper-IgE syndrome; common variable immunodeficiency; ICF syndrome; thymic hypoplasia (e.g.; Di George's syndrome; Nezelof syndrome; Ataxia telangiectasia); purine nucleoside phosphorylase deficiency; adenosine deaminase deficiency; •ZAP70 deficiency; •Bare lymphocyte syndrome; leukopenia; lymphocytopenia (e.g.; idiopathic CD4+ lymphocytopenia); or a complement deficiency. The invention particularly relates to the use of the antibodies of the present invention to mediate both increased production of IFN-γ and increased T cell proliferation.

Up-modulation of the immune system is particularly desirable in the treatment of cancers and chronic infections, and thus the present invention has utility in the treatment of such disorders. Both PD-1 and B7-H1 are over-expressed upon HIV infection (Xu, Huanbin et al. (2010) "*Increased B7-H1 Expression on Dendritic Cells Correlates with Programmed Death* 1 *Expression on T Cells in Simian Immunodeficiency Virus-Infected Macaques and May Contribute to T Cell Dysfunction and Disease Progression*," J. Immunol. 185:7340-7348; Grabmeier-Pfistershammer, K. et al. (2011) "*Identification of PD-*1 *as a Unique Marker for Failing Immune Reconstitution in HIV-*1*-Infected Patients on Treatment*," J Acquir. Immune Defic. Syndr. 56(2):118-124). Thus, expression of B7-H1 on such cells may be used to diagnose HIV in humans. Thus, the anti-PD-1 and anti-B7-H1 antibodies of the present invention have particular utility as therapeutics for HIV infection and AIDS treatment. As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

Cancers and related disorders that can be treated or prevented by methods and compositions of the present invention include, but are not limited to, the following: leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DL-BCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, non-glial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The antibodies and antibody fragments of the present invention are particularly useful for the treatment of cancers that are associated with cells (e.g., exhausted T cells, B cells, monocytes, etc.) that express abnormally high levels of PD-1 (Youngblood, B. (2011) "*Chronic Virus Infection Enforces Demethylation Of The Locus That Encodes PD-1 In Antigen-Specific CD8(+) T Cells*," Immunity 35(3):400-412; Spahn, J. et al. (2011) "*Ineffective CD8(+) T-Cell Immunity To Adeno-Associated Virus Can Result In Prolonged Liver Injury And Fibrogenesis*," Amer. J. Pathol. 179(5):2370-2381; Wang, C. et al. (2011) "*Phenotype, Effector Function, And Tissue Localization Of PD-1-Expressing Human Follicular Helper T Cell Subsets*," BMC Immunol. 12:53, 1-15; Eichbaum, Q. (2011) "*PD-1 Signaling In HIV And Chronic Viral Infection Potential For Therapeutic Intervention?*" Curr. Med. Chem. 18(26):3971-3980; Hallett, W. H. et al. (2011) "*Immunosuppressive Effects Of Multiple Myeloma Are Overcome By PD-L1 Blockade*," Biol Blood Marrow Transplant. 17(8):1133-1145; Ni, L. et al. (2010) "*PD-1 Modulates Regulatory T Cells And Suppresses T-Cell Responses In HCV-Associated Lymphoma*," Immunol. Cell. Biol. 89(4):535-539; Inozume, T. et al. (2010) "*Selection Of CD8+PD-1+ Lymphocytes In Fresh Human Melanomas Enriches For Tumor-Reactive T Cells*," J. Immunother. 33(9):956-964; and Jin, H. T. et al. (2010) "*Cooperation Of Tim-3 And PD-1 In CD8 T-Cell Exhaustion During Chronic Viral Infection*," Proc. Natl. Acad. Sci. (USA) 107(33):14733-14738).

Similar to its application to tumors as discussed above, the antibodies and antigen-binding fragments of the present invention can be used alone, or as an adjuvant, in combination with vaccines or with antimibrobial agents, to stimulate the immune response against toxins or self-antigens or against pathogens (e.g., viruses, such as HIV, HTLV, hepatitis virus, influenza virus, respiratory syncytial virus, vaccinia virus, rabies virus; bacteria, such as those of *Mycobacteria, Staphylococci, Streptococci, Pneumonococci, Meningococci, Conocci, Klebsiella, Proteus, Serratia, Pseudomonas, Legionella, Corynebacteria, Salmonella, Vibrio, Clostridia, Bacilli, Pasteurella, Leptospirosis, Bordatella*, and particularly such pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus *Mucorales* (*mucor, absidia, rhizophus*), *Sporothrix* (*schenkii*), *Blastomyces* (*dermatitidis*), *Paracoccidioides* (*brasiliensis*), *Coccidioides* (*immitis*) and *Histoplasma* (*capsulatuma*), *Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi*, etc.), *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia*, or *Trypanosoma*, etc. Thus, the antibodies and antigen-binding fragments of the present invention have utility in the treatment of infectious disease.

2. Uses of Down-Modulators of the Immune System

In an alternative embodiment, the anti-B7-H1 or anti-PD-1 antibodies of the present invention are employed to produce anti-idiotypic peptides or antibodies (Wallmann, J. et al. (2010) "*Anti-Ids in Allergy: Timeliness of a Classic Concept*," World Allergy Organiz J 3(6):195-201; Nardi, M. et al. (2000) "*Antiidiotype Antibody Against Platelet Anti-Gpiiia Contributes To The Regulation Of Thrombocytopenia In HIV*-1-*ITP Patients*," J. Exp. Med. 191(12):2093-2100) or mimetics (Zang, Y. C. et al. (2003) "*Human Anti-Idiotypic T Cells Induced By TCR Peptides Corresponding To A Common CDR3Sequence Motif In Myelin Basic Protein-Reactive T Cells*," Int. Immunol. 15(9):1073-1080; Loiarro, M. et al. (Epub 2010 Apr. 8) "*Targeting TLR/IL-1R Signalling In Human Diseases*," Mediators Inflamm. 2010:674363) of B7-H1 or PD-1. Such molecules serve as surrogates for B7-H1 or PD-1, and thus their administration to a subject down-modulates the immune system of such subject by mimicking or facilitating B7-H1-PD-1 binding. Such molecules have utility in the treatment of graft vs. host disease. Similarly, agonist antibodies that i) enhance binding between such antibodies and such receptor/ligand or ii) trigger signal transduction when bound directly to B7-H1 or PD-1, have utility as agonists of B7-H1-PD-1 signaling and thus have utility in the treatment of inflammation and autoimmune disease, by directly or indirectly agonizing receptor activity.

Bi-specific antibodies, exhibiting immunospecific binding to both PD-1 and B7-H1 are capable of binding to both APC and T-cells, and thus facilitate the co-localization of APCs and T-cells. Such co-localization facilitates the ability of such cells to bind together via B7-H1 and PD-1 molecules that are not complexed with antibody, or by co-inhibitory molecules. Such binding provides down modulation of the immune system of the recipient.

Down-modulation of the immune system is desirable in the treatment of inflammatory and auto-immune diseases, and graft vs. host disease (GvHD). Examples of autoimmune disorders that may be treated by administering the antibodies of the present invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis.

Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Thus, the antibodies and antigen-binding fragments of the present invention have utility in the treatment of inflammatory and auto-immune diseases.

C. Methods of Administration

Various delivery systems are known and can be used to administer the therapeutic or prophylactic compositions of the present invention, e.g., encapsulation in liposomes, microparticles, microcapsules, recombinant cells capable of expressing the antibody or fusion protein, receptor-mediated endocytosis (see, e.g., Wu and Wu, 1987, *J. Biol. Chem.* 262:4429-4432), construction of a nucleic acid as part of a retroviral or other vector, etc.

Methods of administering a humanized antibody of the invention include, but are not limited to, injection, as by parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody of the invention, care must be taken to use materials to which the antibody or the fusion protein does not absorb.

In some embodiments, the humanized or chimeric antibodies of the invention are formulated in liposomes for targeted delivery of the antibodies of the invention. Liposomes are vesicles comprised of concentrically ordered phopsholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545.

The invention also encompasses methods of preparing liposomes with a prolonged serum half-life, i.e., enhanced circulation time, such as those disclosed in U.S. Pat. No.

5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome, see, e.g., Bendas et al., 2001 *BioDrugs*, 15(4): 215-224; Allen et al., 1987 *FEBS Lett.* 223: 42-6; Klibanov et al., 1990 *FEBS Lett.*, 268: 235-7; Blum et al., 1990, *Biochim. Biophys. Acta.*, 1029: 91-7; Torchilin et al., 1996, *J. Liposome Res.* 6: 99-116; Litzinger et al., 1994, *Biochim. Biophys. Acta*, 1190: 99-107; Maruyama et al., 1991, *Chem. Pharm. Bull.*, 39: 1620-2; Klibanov et al., 1991, *Biochim Biophys Acta*, 1062; 142-8; Allen et al., 1994, *Adv. Drug Deliv. Rev,* 13: 285-309. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody of the invention, e.g., F(ab'), may be conjugated to the liposomes using previously described methods, see, e.g., Martin et al., 1982, *J. Biol. Chem.* 257: 286-288.

The humanized or chimeric antibodies of the invention may also be formulated as immunoliposomes. Immunoliposomes refer to a liposomal composition, wherein an antibody of the invention or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, Stealth Liposomes, Boca Rotan: CRC Press, 233-44; Hansen et al., 1995, *Biochim. Biophys. Acta*, 1239: 133-144. In most preferred embodiments, immunoliposomes for use in the methods and compositions of the invention are further sterically stabilized. Preferably, the humanized antibodies of the invention are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phosphatidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry*, 35: 1100-1105; Loughrey et al., 1987, *Biochim. Biophys. Acta*, 901: 157-160; Martin et al., 1982, *J. Biol. Chem.* 257: 286-288; Martin et al., 1981, *Biochemistry,* 20: 4429-38. Although not intending to be bound by a particular mechanism of action, immunoliposomal formulations comprising an antibody of the invention are particularly effective as therapeutic agents, since they deliver the antibody to the cytoplasm of the target cell, i.e., the cell comprising the receptor to which the antibody binds. The immunoliposomes preferably have an increased half-life in blood, specifically target cells, and can be internalized into the cytoplasm of the target cells thereby avoiding loss of the therapeutic agent or degradation by the endolysosomal pathway.

The immunoliposomal compositions of the invention comprise one or more vesicle forming lipids, an antibody of the invention or a fragment or derivative thereof, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are well known in the art and encompassed within the invention. For a review of immunoliposomes and methods of preparing them, see, e.g., U.S. Patent Application Publication No. 2003/0044407; PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports,* 22(2): 267-281; Bendas et al., 2001 *BioDrugs*, 14(4): 215-224, J. Thomas August, ed., 1997, Gene Therapy: Advances in Pharmacology, Volume 40, Academic Press, San Diego, Calif., p. 399-435.

The invention also provides that the humanized or chimeric antibodies of the invention are packaged in a hermetically sealed container, such as an ampoule or sachette, indicating the quantity of antibody. In one embodiment, the antibodies of the invention are supplied as a dry sterilized lyophilized powder or water free concentrate in a hermetically sealed container and can be reconstituted, e.g., with water or saline to the appropriate concentration for administration to a subject. Preferably, the antibodies of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies of the invention should be stored at between 2 and 8° C. in their original container and the antibodies should be administered within 12 hours, preferably within 6 hours, within 5 hours, within 3 hours, or within 1 hour after being reconstituted. In an alternative embodiment, antibodies of the invention are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the antibodies.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For antibodies encompassed by the invention, the dosage administered to a patient is typically 0.01 mg/kg to 100 mg/kg of the patient's body weight. Preferably, the dosage administered to a patient is between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. In particular, the invention contemplates that the dosage administered to a patient is 0.2 mg/kg, 0.3 mg/kg, 1 mg/kg, 3 mg/kg, 6 mg/kg or 10 mg/kg. A dose as low as 0.01 mg/kg is predicted to would show appreciable pharmacodynamic effects. Dose levels of 0.10-1 mg/kg are predicted to be most appropriate. Higher doses (e.g., 1-30 mg/kg) would also be expected to be active. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations comprising one or more antibodies of the invention. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760. In one embodiment, a pump may be used in a controlled release system (See Langer, supra; Sefton, 1987, *CRC Crit. Ref Biomed. Eng.* 14:20; Buchwald et al., 1980, Surgery 88:507; and Saudek et al., 1989, *N. Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; See also Levy et al., 1985, *Science* 228:190; During et al., 1989, Ann. Neurol. 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533). Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760.

In a specific embodiment wherein the therapeutic or prophylactic composition of the invention is a nucleic acid encoding an antibody of the invention or an antigen-binding fragment thereof, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

Treatment of a subject with a therapeutically or prophylactically effective amount of antibodies of the invention can include a single treatment or, preferably, can include a series of treatments.

D. Pharmaceutical Compositions

The compositions of the invention include bulk drug compositions useful in the manufacture of pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of humanized antibodies of the invention and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, surfactant, cryoprotectant or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, polysorbate-80 and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

E. Kits

The invention provides a pharmaceutical pack or kit comprising one or more containers filled with humanized antibodies of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more humanized antibodies of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

F. Diagnostic Methods

The antibodies of the invention and their antigen-binding fragments can be used for diagnostic purposes, such as to detect, diagnose, or monitor diseases, disorders or infections associated with B7-H1 or PD-1 expression. The invention provides for the detection or diagnosis of a disease, disorder or infection, particularly an autoimmune disease comprising: (a) assaying the expression of B7-H1 or of PD-1 in cells or in a tissue sample of a subject using one or more antibodies (or fragments thereof) that immunospecifically bind to such antigens; and (b) comparing the level of the antigen with a control level, e.g., the level in a normal tissue sample, or before treatment, whereby an increase or decrease in the assayed level of antigen compared to the control level of the antigen is indicative of the disease, disorder or infection, or of the subject's response to treatment. Thus, the invention also provides for monitoring the progression of a disease, disorder or infection, comprising: (a) assaying the expression of B7-H1 or of PD-1 in cells or in a tissue sample of a subject at one point in time using one or more antibodies (or fragments thereof) that immunospecifically bind to such antigens; and (b) comparing the level of expression of B7-H1 or of PD-1 in cells or in a tissue sample of a subject at another point in time, or over a time course, whereby an increase or decrease in the assayed level of antigen is indicative of the progression of disease, disorder or infection. The invention additionally provides for monitoring the response to treatment, comprising: (a) assaying the expression of B7-H1 or of PD-1 in cells or in a tissue sample of a subject prior to treatment with one or more antibodies (or fragments thereof) that immunospecifically bind to such antigens; and (b) assaying the expression of B7-H1 or of PD-1 in cells or in a tissue sample of a subject prior at one or more time points after treatment, and comparing the level of the antigen over time, whereby an increase or decrease in the assayed level of antigen compared to the pre-treatment level of the antigen is indicative of a response to treatment. Such antibodies and fragments are preferably employed in immunoassays, such as the enzyme linked immunosorbent assay (ELISA), the radioimmunoassay (RIA) and fluorescence-activated cell sorting (FACS).

One aspect of the invention relates to the use of such antibodies and fragments, and particularly such antibodies and fragments that bind to human B7-H1, as reagents for IHC analysis in cells of an in vitro or in situ tissue sample or in vivo. For example, since B7-H1 is expressed by cancer cells but not by normal tissue (Dong, H. (2003) "*B7-H1 Pathway And Its Role In The Evasion Of Tumor Immunity*," J. Mol. Med. 81:281-287), detection of its presence on a cell by such cell's binding to such antibodies or fragments is indicative and diagnostic of a cancer cell. Thus, the present invention provides a cytologic assay for diagnosing the presence of cancer in a subject.

The presence of B7-H1 on tumor cells has been found to enhance apoptosis of T cells that respond to the tumor (U.S. Pat. No. 7,794,710). Thus, by determining the extent or degree to which tumor cells of a cancer patient exhibit B7-H1 on their surfaces, the present invention provides a means for determining the clinical significance of the cancer, and the extent to which it will be refractory to an immune response.

Similarly, B7-H1 is expressed on lymphoid and mucosal dendritic cells (both myeloid and plasmacytoid dendritic cells), and its expression significantly increases after SIV infection (Xu, Huanbin et al. (2010) "*Increased B7-H1 Expression on Dendritic Cells Correlates with Programmed Death* 1 *Expression on T Cells in Simian Immunodeficiency Virus-Infected Macaques and May Contribute to T Cell Dysfunction and Disease Progression*," J. Immunol. 185:7340-7348). Thus, expression of B7-H1 on such cells may be used to diagnose HIV in humans. Additionally, it has been found that PD-1 expression on CD8+ cells is increased in the context of HIV infection (Killian, M. S. et al. (2011) "*Natural Suppression of Human Immunodeficiency Virus Type* 1 *Replication Is Mediated by Memory CD8$^+$ T Cells*," J. Virol. 85(4):1696-1705). Thus antibodies that bind to both PD-1 and CD8 have particular utility in the diagnosis of HIV infection and AIDS progression.

A further aspect of the invention relates to the use of such antibodies and fragments, and particularly such antibodies and fragments that bind to human PD-1. PD-1 has particular utility as a marker of chronic immune activation and T-cell exhaustion. Its expression is enhanced on T cells of viremic HIV-infected patient and correlates with the viral load in these patients (Khaitan, A. et al. (2011) "*Revisiting Immune Exhaustion During HIV Infection*," Curr. HIV/AIDS Rep. 8:4-11; Grabmeier-Pfistershammer, K. et al. (2011) "*Identification of PD-*1 *as a Unique Marker for Failing Immune Reconstitution in HIV-*1*-Infected Patients on Treatment*," J Acquir. Immune Defic. Syndr. 56(2):118-124). Thus, PD-1 has particular utility as a marker of HIV progression. Most preferably PD-1 expression will be assessed using flow cytometry. Through the use of such antibodies and fragments, T cells (which express PD-1) can be analyzed for multiple parameters (e.g., cell counting, cell size, phenotype and cellular health, etc.) even though present in heterogeneous preparations. Thus, in concert with antibodies to PD-1 and their antigen-binding fragments, such methods can be used to diagnose the extent or severity of AIDS, leukemias, and other disease affecting T cell number and health. Methods of flow cytometry that may be adapted to the purposes of the present invention are disclosed in and in Peters, J. M. et al. (2011) "*Multiparameter Flow Cytometry In The Diagnosis And Management Of Acute Leukemia*," Arch. Pathol. Lab. Med. 135(1):44-54; Meyerson, H. J. (2010) "*A Practical Approach To The Flow Cytometric Detection And Diagnosis Of T-Cell Lymphoproliferative Disorders*," Lab. Hematol. 16(3):32-52; Vandewoestyne, M. et al. (Epub 2010 Aug. 3) *Laser Capture Microdissection In Forensic Research: A Review*," Int. J. Legal. Med. 124(6):513-521; Ornatsky, O. et al. (Epub 2010 Jul. 21) "*Highly Multiparametric Analysis By Mass Cytometry*," J. Immunol. Meth. 361(1-2):1-20; Mach, W. J. et al. (Epub 2010 Jul. 13) "*Flow Cytometry And Laser Scanning Cytometry, A Comparison Of Techniques*," J. Clin. Monit. Comput. 24(4):251-259; and Chattopadhyay, P. K. et al. (2010) "*Good Cell, Bad Cell: Flow Cytometry Reveals T-Cell Subsets Important In HIV Disease*," Cytometry A. 77(7):614-622; and in U.S. Pat. Nos. 7,876,436; 7,847,923; 7,842,244; 7,746,466; 7,590,500; 7,527,978; 7,507,548; 7,491,502; 7,486,387; 7,479,630; 7,465,543; 7,354,773; 6,794,152 and 6,784,981

Thus, the antibodies and fragments of the present invention have utility in the detection and diagnosis of a disease, disorder, or infection in a human. In one embodiment, such diagnosis comprises: a) administering to a subject (for example, parenterally, subcutaneously, or intraperitoneally) an effective amount of a labeled antibody or antigen-binding fragment that immunospecifically binds to B7-H1 or PD-1; b) waiting for a time interval following the administration for permitting the labeled molecule to preferentially concentrate at sites in the subject where B7-H1 or PD-1 is expressed (and for unbound labeled molecule to be cleared to background level); c) determining background level; and d) detecting the labeled antibody in the subject, such that detection of labeled antibody above the background level indicates that the subject has the disease, disorder, or infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Having now generally described the invention, the same will be more readily understood through reference to the following examples, which are provided by way of illustration and are not intended to be limiting of the present invention unless specified.

EXAMPLE 1

Isolation and Characterization of Anti-Human B7-H1 Antibodies

In order to isolate high affinity neutralizing anti-human B7-H1 antibodies, mice were first immunized and then boosted with human B7-H1-Fc. Splenocytes from anti-B7-

H1 positive animals were fused with myeloma cells following standard protocol. The resulting murine hybridomas were screened for those that express B7-H1-immunoreactive monoclonal antibodies. Antibodies were additionally evaluated to determine whether they were IgG or IgM antibodies. Accordingly, B7-H1-Fc or negative control was immobilized to a solid support. Hybridoma supernatants were then placed in contact with the support, and the presence of anti-B7-H1 antibody was determined using labeled anti-mouse IgG or anti-mouse IgM. FIG. 1 shows the results of tested hybridoma supernatants and indicates the isolation of multiple hybridoma lines that express antibody immunoreactive with human B7-H1.

Figure 2:
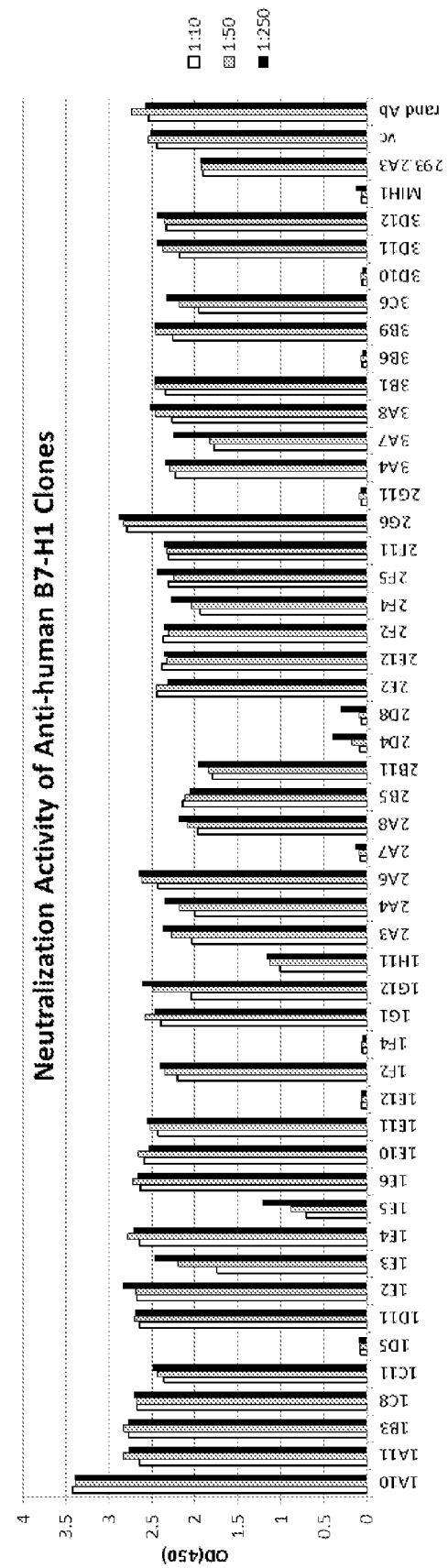
FIG. 2 shows the results of experiments for determining whether the isolated anti-B7-H1 antibodies are capable of modulating the binding of B7-H1 to PD-1. Positive control: clones MIH-1 and 29E.2A3 (both anti-human CD274 (B7-H1); Two negative controls: conditioned media from an unrelated hybridoma (random Ab) and vector control (VC).

The identified hybridomas were screened to determine whether their expressed antibodies were neutralizing antibodies and as such capable of blocking the binding between B7-H1 and PD-1. PD-1-Fc was immobilized to a solid support, which was then incubated in the presence of diluted conditioned media containing biotinylated B7-H1-Fc. The ability of the B7-H1 and PD-1 to bind to one another was detected by assaying for the binding of streptavidin-horse radish peroxidase (SA-HRP) to the solid support. Anti-B7-H1 antibody capable of modulating the binding of B7-H1 to PD-1 thus mediate a decrease in SA-HAS binding in this assay. The results of the experiment are shown in FIG. 2, and indicate that several of the isolated hybridomas expressed human B7-H1 neutralizing antibodies. Antibody MIH-1 (anti-human CD274 (B7-H1) (Chen, Y. et al. (Epub 2005 Nov. 11) "*Expression Of B7-H1 In Inflammatory Renal Tubular Epithelial Cells*," Nephron. Exp. Nephrol. 102(3-4):e81-e92) was used as a positive control. 29E.2AE is an anti-PD-1 antibody but was shown to be non-neutralizing in this assay. Conditioned media from an unrelated hybridoma (rand Ab) and a vector control (VC) were used as negative controls.

Figure 3:
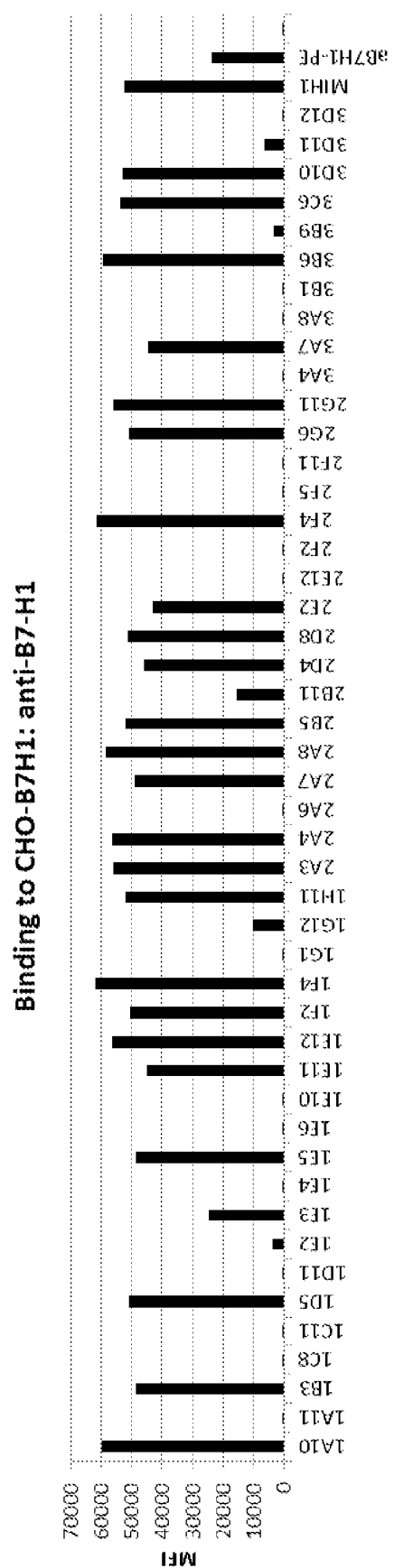
FIG. 3 shows the median fluorescence intensity (MFI) of tested anti-B7-H1 antibodies for binding to CHO-hB7-H1. None of the tested clones were found to cross-react with the parental CHO line, indicating that the expressed antibody was immunospecific for human B7-H1.

In order to determine whether the expressed neutralizing antibodies were capable of binding to B7-H1 that was arrayed on the surface of a cell, a cell binding assay was conducted. Supernatant from each hybridoma clone was diluted 1:4 and incubated in the presence of parental CHO cells and a clonal CHO line that overexpressed full length human B7-H1. After permitting binding to occur, the cells were washed and the presence of residual cell-bound anti-B7-H1 antibody was detected using fluorescently labeled anti-mouse IgG antibody. The median fluorescence intensity (MFI) for binding to CHO-hB7-H1 is shown in FIG. 3. None of the tested clones were found to cross-react with the parental CHO line, indicating that the expressed antibody was specific for human B7-H1.

Figure 4:
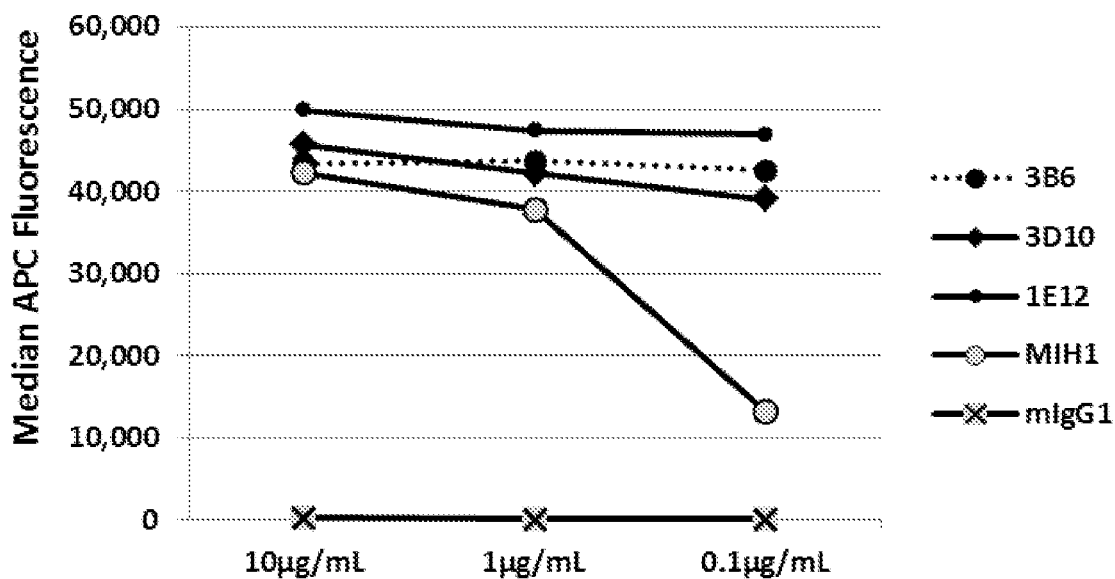
FIG. 4 shows the median fluorescence intensity (MFI) result of a human B7-H1-expressing CHO cell binding assay of selected anti-human B7-H1 antibodies.
Figure 5:
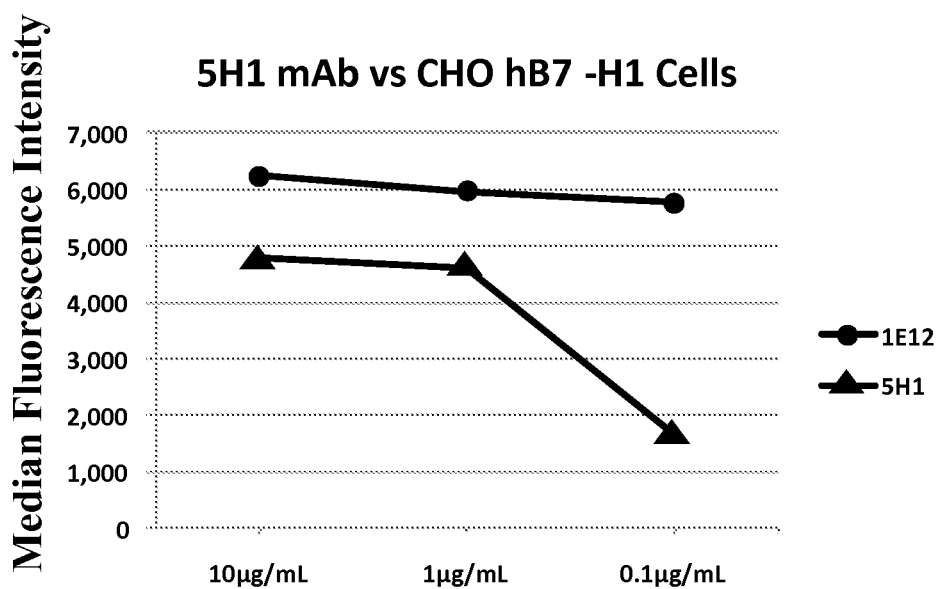
FIG. 5 compares the median fluorescence intensity (MFI) result of a human B7-H1-expressing CHO cell binding assay of anti-human B7-H1 antibodies 5H1 and 1E12.

As a further assessment, different concentrations of three clones were compared to anti-B7-H1 antibody MIH-1. Antibody was purified using protein G and assessed for ability to bind to B7-H1 when present at endogenous levels and as arrayed on the surface of an APC. CHO cells that expressed human B7-H1 were incubated with varying concentrations (10, 1 or 0.1 µg/ml) of anti-B7-H1 antibody followed by incubation with APC-conjugated donkey anti-mouse antibody. Binding was reported by measuring median fluorescence intensity. The results show that the tested antibodies exhibited greater avidity toward B7-H1 than the control antibody (MIH1) (FIG. 4) and that antibody 1E12 exhibited greater avidity toward B7-H1 than a control anti-B7-H1 antibody (5H1) (Dong, H. et al. (2002) "*Tumor-Associated B7-H1 Promotes T-Cell Apoptosis: A Potential Mechanism Of Immune Evasion*," Nature Med. 8(8):793-800) (FIG. 5).

In summary, the data show that multiple anti-human B7-H1-expressing hybridomas were obtained. All clones are IgG antibodies that recognize B7-H1-Fc. Clones 1B3, 1D11, 1E2, 1E4, 1E10, 2A6, 2E12, 2F2, 2F5, 2F11, 3A4, and 3B1 are weak in the screening binding assay. Low signal could be due to low expression levels and/or weak affinity.

Significantly, several clones (e.g., clones: 1D5, 1E12, 1F4, 2A7, 2G11, 3B6, 3D10) showed strong neutralizing activity. All are neutralizing at all concentrations tested and appear to bind to antigen well. MFI for binding to CHO-B7-H1 cells is as follows: 1D5=50,821; 1E12=56,152; 1F4=62,015; 2A7=49,008; 2G11=55,947; 3B6=59,638; 3D10=53,114.

EXAMPLE 2

Isolation and Characterization of Anti-Human PD-1 Antibodies

Figure 6:
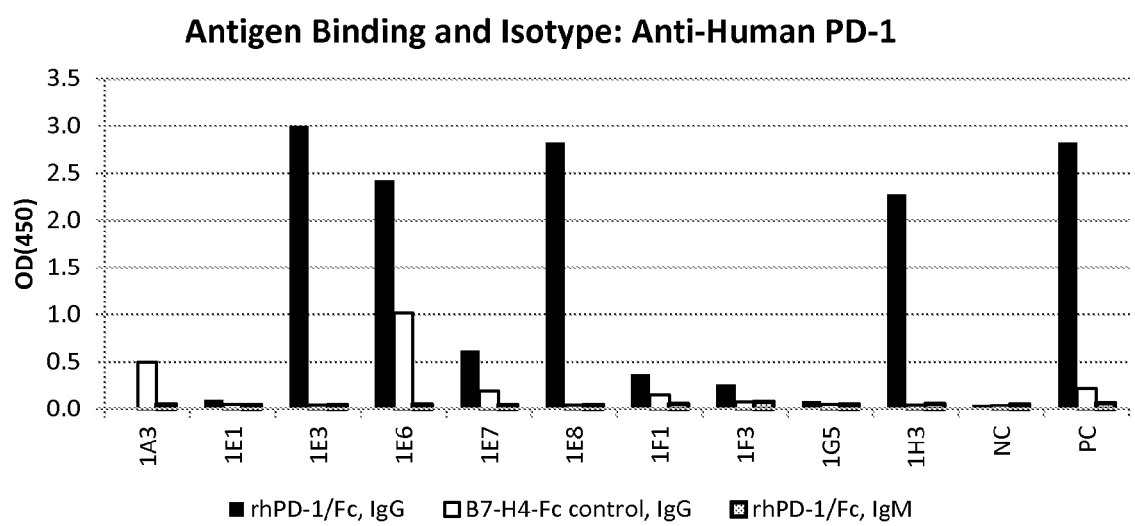
FIG. 6 shows the antigen binding and isotype of the isolated anti-human PD-1 antibodies.

In order to isolate high affinity neutralizing anti-human PD-1 antibodies, mice were first immunized and then boosted with human PD-1-Fc. Splenocytes from anti-PD-1 positive animals were fused with myeloma cells following standard protocol. The resulting murine hybridomas were screened for those that express high affinity human PD-1-immunoreactive monoclonal antibodies. Antibodies were additionally evaluated to determine whether they were IgG or IgM antibodies. Accordingly, PD-1-Fc or negative control (B7-H4-Fc) was immobilized to a solid support. Hybridoma supernatants were then placed in contact with the support, and the presence of anti-PD-1 antibody was determined using labeled anti-mouse IgG or anti-mouse IgM. FIG. 6 shows the antigen binding and isotype of the isolated anti-human PD-1 antibodies and indicates the isolation of multiple hybridoma lines that express antibody immunoreactive with human PD-1.

Figure 7A:
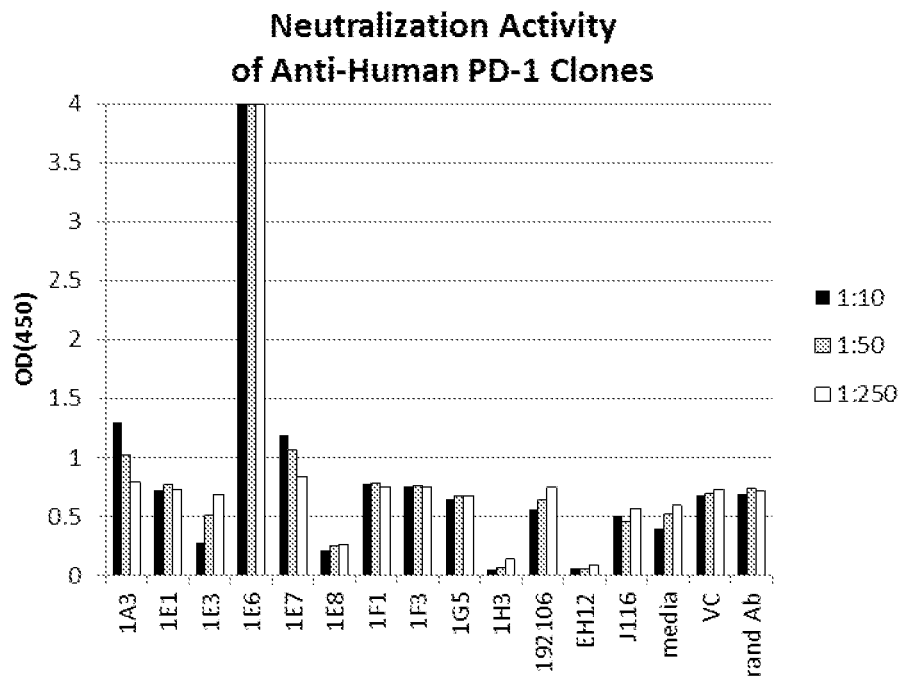
FIGS. 7A-7B show the results of experiments indicating that several of the isolated hybridomas expressed neutralizing anti-human PD-1 antibodies.
Figure 7B:
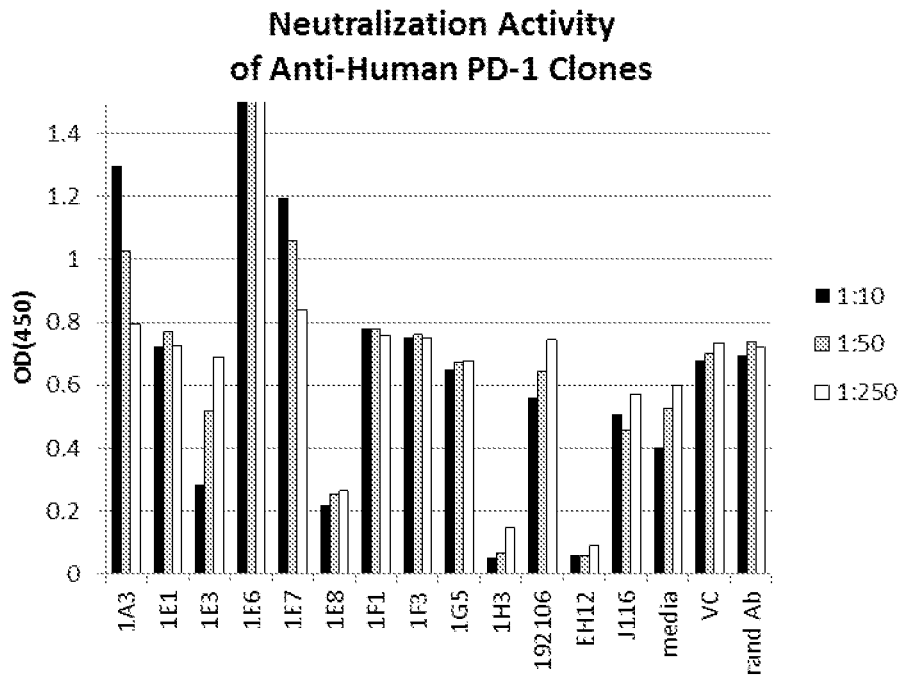

The identified hybridomas were screened to determine whether their expressed antibodies were neutralizing antibodies and as such capable of blocking the binding between B7-DC and PD-1. B7-DC-Fc, a fusion protein that binds PD-1, was immobilized to a solid support, which was then incubated in the presence of diluted conditioned media containing biotinylated PD-1-Fc. The ability of the B7-DC and PD-1 to bind to one another was detected by assaying for the binding of streptavidin-horse radish peroxidase (SA-HRP) to the solid support. Anti-PD-1 antibody capable of blocking the binding of B7-DC to PD-1 thus mediates a decrease in SA-HRP binding in this assay. The results of the experiment are shown in FIGS. 7A and 7B, and indicate that several of the isolated hybridomas expressed human PD-1 neutralizing antibodies (FIG. 7B shows the same graph as FIG. 7A, but at a different scale).

Figure 8:
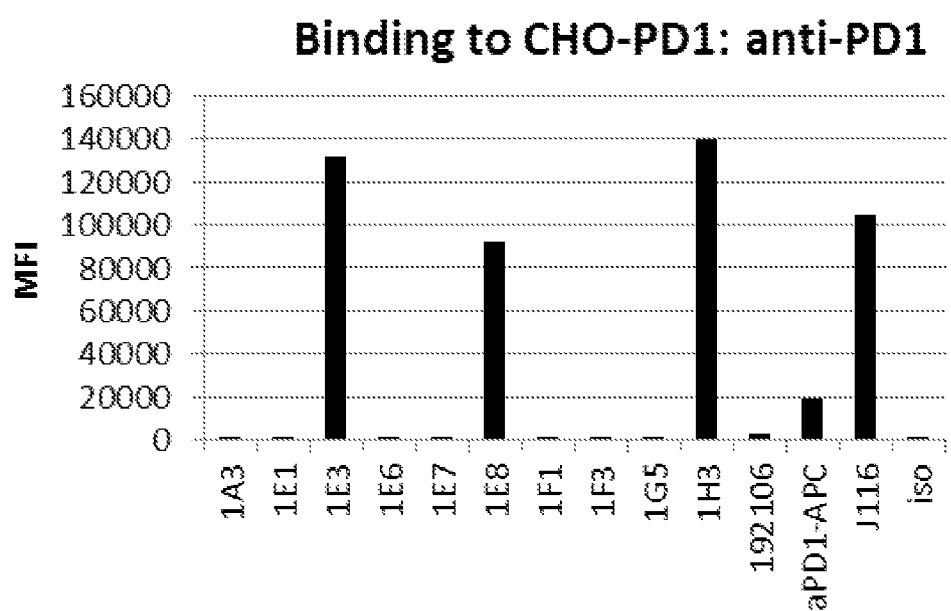
FIG. 8 shows the median fluorescence intensity (MFI) of tested anti-PD-1 antibodies for binding to CHO-hPD-1. None of the tested clones were found to cross-react with the parental CHO line, indicating that the expressed antibody was specific for human PD-1.

A cell binding assay was conducted in order to determine whether the expressed neutralizing antibodies were capable of binding to PD-1 arrayed on a cell surface. Supernatant from each hybridoma clone was diluted 1:4 and incubated in the presence of parental CHO cells and a clonal CHO line that overexpressed full length human PD-1. After permitting binding to occur, the cells were washed and the presence of residual cell-bound anti-PD-1 antibody was detected using fluorescently labeled anti-mouse IgG antibody. The median fluorescence intensity (MFI) for binding to CHO-hPD-1 is shown in FIG. 8. The results demonstrate that antibodies 1E3, 1E8, and 1H3 were particularly capable of binding to human PD-1 expressed on a cell surface. None of the tested clones were found to cross-react with the parental CHO line, indicating that the expressed antibody was specific for human PD-1. J116 is commercially available anti-human PD-1 con trol antibody (eBioscience, Inc.). Isotyping revealed that 1E3, 1E8, 1H3 are IgG1/kappa.

Figure 9:
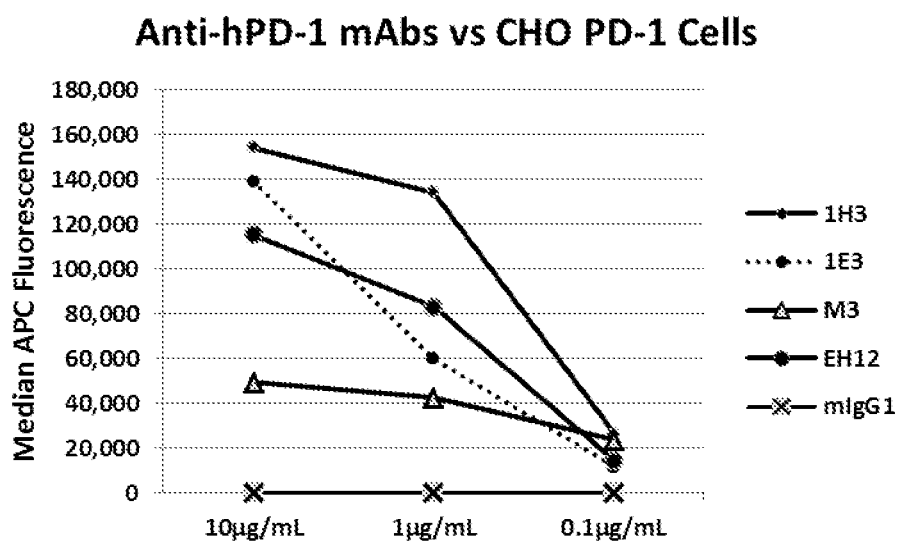
FIG. 9 shows the median fluorescence intensity (MFI) of a human PD-1-expressing CHO cell binding assay of selected anti-human PD-1 antibodies. Positive control: EH12 (a commercially available anti-human PD-1 antibody from BioLegend); mIgG1: murine IgG negative control.

Two clones (1E3 and 1H3) were selected for further study. As a further assessment, different concentrations of two clones were compared to anti-PD-1 antibodies M3 and EH-12. Antibody was purified using protein G and assessed for ability to bind to PD-1 expressed on the surfaces of CHO cells. CHO-hPD1 cells were stained with unlabeled anti-PD-1 antibody (10, 1, and 0.1 µg/mL) followed by APC-conjugated donkey anti-mouse antibody and the median fluorescence intensity was reported. The results of the assay are reported in FIG. 9. The negative control is murine IgG (mIgG1); the positive controls are M3 (a neutralizing monoclonal antibody against human PD-1 (Wu, K. et al. (2009) "*Kupffer Cell Suppression of CD8+ T Cells in Human Hepatocellular Carcinoma Is Mediated by B7-H1/Programmed Death-1 Interactions,*" Cancer Res 69(20):8067-8075) and anti-PD-1 antibody EH12 (Dorfman, D. M. et al. (2006) "*Programmed Death-1 (PD-1) Is A Marker Of Germinal Center-Associated T Cells And Angioimmunoblastic T-Cell Lymphoma,*" Am. J. Surg. Pathol. 30(7):802-810).

Figure 10:
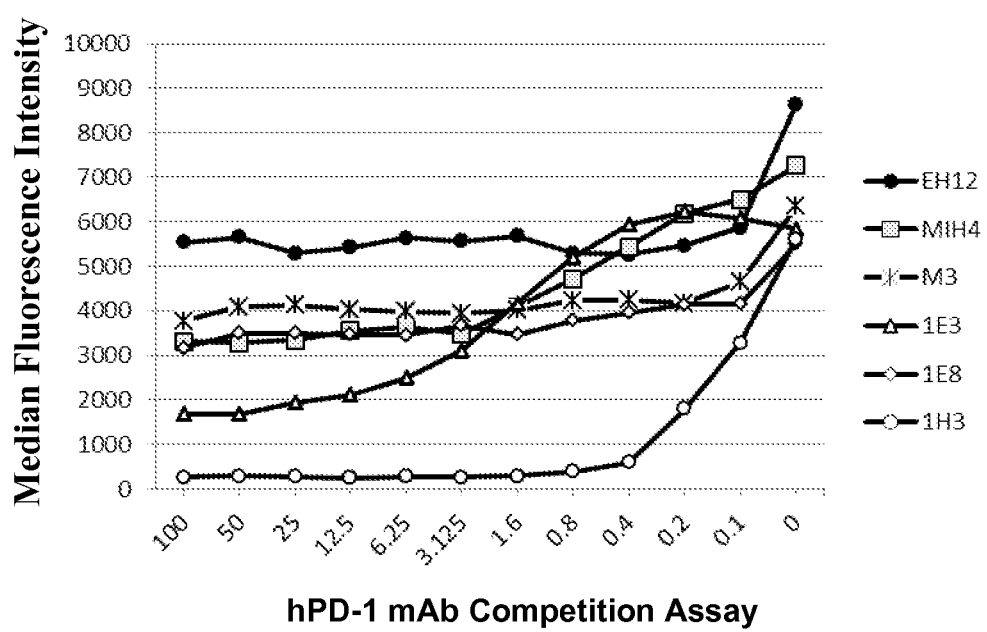
FIG. 10 shows the median fluorescence intensity (MFI) result of a cell-based competition assay at varying concentrations of anti-human PD-1 antibodies.
Figure 11:
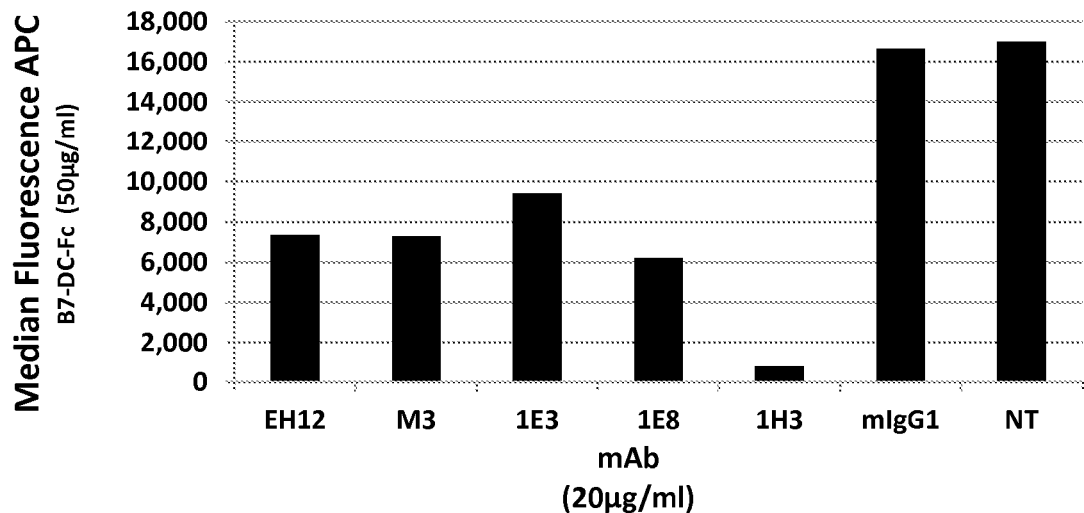
FIG. 11 shows the median fluorescence intensity (MFI) result of a cell-based competition assay at a concentration of 20 μg/ml anti-human PD-1 antibody.

A cell-based competition assay was performed by incubating 50,000 CHO-hPD1 cells for 30 minutes with anti-PD-1 antibody (present at concentrations ranging from 0-0.1 mg/ml). 10 µg/ml of APC-labeled B7-DC-Fc was then added and the incubation continued for an additional 30 minutes, after which the fluorescence of bound B7-DC-Fc was measured. The median fluorescence intensity is shown in FIG. 10. The competition was repeated at a fixed antibody concentration of 20 µg/mL (FIG. 11).

In summary, the results show that clones 1E3, 1E8, and 1H3 exhibit neutralizing activity and recognize antigen well. Clone 1E6 is able to cross-link PD-1 without neutralizing it, thereby giving enhanced binding. However this clone does not appear to bind PD-1 on the cell surface.

EXAMPLE 3

Production of Humanized Antibodies

General Methodology

As indicated above, for certain purposes, including for example, use in the in vivo treatment of human disease, it is preferred to employ a humanized derivative of the above-described anti-human B7-H1 and/or anti-human PD-1 antibodies.

To form such derivatives, the framework sequences of the 3D10 or 1H3 antibodies (the "Parental" sequences) were first aligned with framework sequences of a set of "Acceptor" human antibodies in order to identify differences in the framework sequences. Humanization was accomplished by substituting non-matching framework residues between the Parental and the Acceptor. Substitutions at potentially important positions such as those in the Vernier zone, the VH/VL inter-chain interface or CDR canonical class determining positions were analyzed for prospective back mutations (see, Foote, J. et al. (1992) "*Antibody Framework Residues Affecting The Conformation Of The Hypervariable Loops,*" J. Molec. Biol. 224:487-499). A total 14 humanized variant sequences were identified.

The Conserved Domain Database (COD) (Marchler-Bauer, et al. (2011) "*COD: A Conserved Domain Database For The Functional Annotation Of Proteins,*" Nucleic Acids Res. 39:D225-D229) was used to determine the domain content of each amino-acid chain and the approximate boundaries of each domain. Variable domain boundaries were exactly determined along with the boundaries of the complementarity-determining regions (CDRs) according to several commonly used definitions (Kabat, E. A. et al. (1991) "*Sequences of Proteins of Immunological Interest,*" Fifth Edition. NIH Publication No. 91-3242; Chothia, C. et al. (1987) "*Canonical Structures For The Hypervariable Regions Of Immunoglobulins,*" J. Mol. Biol. 196:901-917); Honegger, A. et al. (2001) "*Yet Another Numbering Scheme For Immunoglobulin Variable Domains: An Automatic Modeling And Analysis Tool,*" J. Molec. Biol. 309(3):657-670; Chothia's CDR definition (Chothia, C. et al. (1987) "*Canonical Structures For The Hypervariable Regions Of Immunoglobulins,*" J. Mol. Biol. 196:901-917) will be used below with respect to such humanized sequences.

Multiple alignments of the Parental sequence to the mouse and human germline sequences were generated using MAFFT (Katoh, K. et al. (2002) "*MAFFT: A Novel Method For Rapid Multiple Sequence Alignment Based On Fast Fourier Transform,*" Nucleic Acids Res. 30: 3059-3066) and entries in each alignment were ordered according to the sequence identity to the Parental sequence. Reference sets were reduced to a unique set of sequences by clustering at 100% sequence identity and excluding redundant entries.

The optimal Acceptor framework selection was based on the overall Parental antibodies sequence identity to the Acceptor across the framework of both chains; however the positions that compose the VH/VL inter-chain interface are of particular interest. Additionally, the CDR-loops lengths and CDR positions responsible for the discrete set of canonical structures that has been defined for 5 of the CDRs (Chothia, C. et al. (1987) "*Canonical Structures For The Hypervariable Regions Of Immunoglobulins,*" J. Mol. Biol. 196:901-917; Martin, A. C. et al. (1996) "*Structural Families In Loops Of Homologous Proteins: Automatic Classification, Modelling And Application To Antibodies,*" J. Molec. Biol 263:800-815; Al-Laziniki, B. et al. (1997) "*Standard Conformations For The Canonical Structures Of Immunoglobulins,*" J. Molec. Biol. 273:927-948) were compared to the germlines, in order to determine which germline frameworks had both the same interface residues and were known to support similar CDR-loop conformations. Table 6 and Table 7 show the conserved positions within the VH/VL interface and the positions which determine the CDR canonical class (respectively), with numbering according to Chothia's definition.

TABLE 6

Conserved Positions Within The VH/VL Interface of Antibody 1H3

| Domain | Positions |
|---|---|
| VL | 34, 36, 38, 43, 44, 46, 87, 88, 89, 91, 96, 98 |
| VH | 35, 37, 39, 45, 47, 91 , 93, 95 100-100K*, 101, 103 |

*The numbering of the position one N-terminal to position 101 differs by CDR H3 length

TABLE 7

Positions Determining CDR Canonical Class of Antibody 1H3

| Domain | Positions |
|---|---|
| L1 | 2, 25, 29, 30, 30D*, 33, 71 |
| L2 | 34 |
| L3 | 90, 94, 95, 97 |
| H1 | 24, 26, 29, 34, 94 |
| H2 | 54, 55, 71 |

*If CDR L1 is long enough to contain the position

Based on the parent antibody's sequence alignment to the human germlines the closest matching entries were identified. The choice of the preferred human germline was based on the ordered criteria: (1) Sequence identity across the framework; (2) Identical or compatible inter-chain interface residues; (3) Support loops with the Parental CDRs canonical conformations; (4) The combination of heavy and light germlines are found in expressed antibodies; and (5) Presence of N-glycosylation sites that have to be removed.

A structural model of antibody 1H3's Fv-region was generated. Candidate structural template fragments for the framework (FR) and complementarity-determining regions (CDRs) as well as the full Fv were scored, ranked and selected from an antibody database based on their sequence identity to the target, as well as qualitative crystallographic measures of the template structure such as the resolution, in Angstroms (Å).

In order to structurally align the CDRs to the FR templates, 5 residues on either side of the CDR were included in the CDR template. An alignment of the fragments was generated based on overlapping segments and a structural sequence alignment generated. The template fragments along with the alignment were processed by MODELLER (SalI, A. et al. (1993) "*Comparative Protein Modelling By Satisfaction Of Spatial Restraints*," J. Molec. Biol. 234:779-815). This protocol creates conformational restraints derived from the set of aligned structural templates. An ensemble of structures which satisfied the constraints was created by conjugate gradient and simulated annealing optimization procedures. Model structures were selected from this ensemble on the basis of an energy score, derived from the score of the proteins structure and the satisfaction of the conformational constraints. The models were inspected and the side chains of the positions which differed between the target and template were optimized using a side chain optimization algorithm and energy minimized. A suite of visualization and computational tools were used to assess the CDRs conformational variability, local packing and surface analysis to select one or more preferred models.

A structural model of the Parental antibody was constructed and inspected for imperfections such as poor atomic packing, strain in bond lengths, bond angles or dihedral angles. These imperfections may indicate potential issues with the structural stability of the antibody. The modeling protocol seeks to minimize such imperfections. The initial structural model of the Humanized Fv contains all safe substitutions (i.e., substitutions that should not affect binding affinity or stability) and cautious substitutions (i.e., the position substitution is made but the position may be important for binding affinity). Substitutions at positions that are considered to be associated with a risk a decreased binding affinity or reduced stability are not altered. The template search and selection was performed separately to the Parental template search in order to create a good stand-alone model rather than a closely matching variant model of the Parental. As the assessment of potential substitutions was performed the model was updated to reflect the preferred substitutions and the effect of back mutations.

EXAMPLE 4

Production of Humanized Anti-Human B7-H1 Antibodies

To illustrate the production of such humanized derivatives, humanized derivatives of anti-human B7-H1 antibody 3D10 was produced in accordance with the above-described procedure.

Sequence alignments comparing 3D10 light chain variable domains to the human germ lines were generated using: IGKV3 light chain germlines (IGKV3-11*01, IGKV3-11*02, IGKV3-NL5*01, IGKV3D-11*01, IGKV3-NL4*01, IGKV3D-7*01, IGKV3D-20*01, IGKV3-20*01, IGKV3-20*02, and IGKV3-15*01), IGKV1 light chain germlines (IGKV1-9*01, IGKV1-39*01, IGKV1D-13*01, IGKV1-16*01, IGKV1-8*01, IGKV1-13*02, IGKV1-NL1*01, IGKV1D-43*01, IGKV1-27*01, and IGKV1-12*01) and IGKJ light chain germlines (IGKJ4*01, IGKJ2*02, IGKJ2*01, IGKJ2*04, IGKJ2*03, IGKJ5*01, IGKJ1*01, and IGKJ3*01).

Sequence alignments comparing 3D10 heavy chain variable domains to the human germ lines were generated using: IGHV1 heavy chain germlines (IGHV1-2*02, IGHV1-2*04, IGHV1-f*01, IGHV1-48*01, IGHV1-2*03, IGHV1-2*01, IGHV1-46*02, IGHV1-2*05, IGHV1-3*01, and IGHV1-8*01), IGHV3 heavy chain germlines (IGHV3-49*04, IGHV3-49*01, IGHV3-49*02, IGHV3-49*03, IGHV3-64*01, IGHV3-64*02, IGHV3-72*01, IGHV3-66*01, and IGHV3-23*01), and IGHJ heavy chain germlines (IGHJ3*02, IGHJ6*01, IGHJ3*01, IGHJ6*03, IGHJ5*02, IGHJ5*01, IGHJ4*01, IGHJ1*01, IGHJ6*04, and IGHJ2*01).

(A) Humanization of the Light Chain

Based on the above criteria, the light chain of antibody 3D10 was found to be most similar to the light chain of germline

```
IGKV3-11*01 (SEQ ID NO: 78):
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ RSNWP
and

IGKV1-9*01 (SEQ ID NO: 79):
DIQLTQSPSF LSASVGDRVT ITCRASQGIS SYLAWYQQKP

GKAPKLLIYA ASTLQSGVPS RFSGSGSGTE FTLTISSLQP

EDFATYYCQQ LNSYP
``` with IGKV3-11*01 being preferred, as shown in Table 8 (CDR residues of antibody 3D10 are shown in italics, identical aligned residues are shown underlined):

TABLE 8

Alignment of Light Chain Variable Regions

| Light Chain | SEQ ID NO. | Sequence |
|---|---|---|
| | | 1          10          20          30          40 |
| 3D10 | 9 | QIVLSQSPAI LSASPGEKVT MTC*RASSSVS* *YIY*WFQQKPG |
| IGKV3-11*01 | 78 | <u>EIVLTQSPAT</u> <u>LSLSPGERAT</u> <u>LSCRASQSVS</u> <u>S</u>YLA<u>WYQQKPG</u> |
| IGKV1-9*01 | 79 | D<u>IQLT</u>QSPSF <u>LSASVG</u>D<u>RVT</u> <u>ITCRASQGISS</u> YLA<u>WYQQKPG</u> |

TABLE 8-continued

Alignment of Light Chain Variable Regions

| Light Chain | SEQ ID NO. | Sequence |
|---|---|---|
| | | 41          50          60          70          80 |
| 3D10 | 9 | SSPKPWIYAT FNLASGVPAR FSGSGSGTSY SLTISRVETE |
| IGKV3-11*01 | 78 | QA<u>PRLL</u>I<u>Y</u>DA S<u>N</u>RAT<u>GIPAR</u> <u>FSGSGSGT</u>DF <u>TLTISS</u>L<u>EPE</u> |
| IGKV1-9*01 | 79 | KA<u>P</u>KLL<u>I</u>YAA STL<u>QSGVPSR</u> <u>FSGSGSGT</u>EF <u>TLTISS</u>L<u>QPE</u> |
| | | 81          90          100         106 |
| 3D10 | 9 | DAATYYC*QQW* *SNNPLT*FGAG TKLELK |
| IGKV3-11*01 | 78 | <u>DF</u>A<u>VYYCQQ</u>R S<u>NW</u>P---- -------- |
| IGKV1-9*01 | 79 | <u>DF</u>A<u>TYYCQQ</u>L <u>N</u>SYP---- -------- |

The J-segment genes were compared to the Parental sequence over FR4, and J-segment IGKJ4*01 (SEQ ID NO:80: LTFGGGTKVEIK) was selected for the light chain.

As shown above, the light chain of antibody 3D10 has a short ten residue CDR L1 similar to canonical class I loops. Human germlines do not have such a short CDR L1. Each of the selected germlines, IGKV3-11*01 and IGKV1-9*01, have shorter L1 loops containing the correct framework residues to support this type of loop. A good overall sequence similarity is observed between both Acceptor frameworks and the Parental sequence, however important differences are observed at the interface positions Y33 and P45. Residue Y33 is in CDR L1 and whilst the two selected Acceptor families do not contain tyrosine at this position, other germline sequences do. The difference between the Acceptor frameworks and the Parental sequence at position P45 is a consequence of the Parental germline possessing a FR2 dissimilar to any human germline. As a result changes in this region were proposed regardless of the Acceptor framework chosen, so IGKV3-11*01 and IGKV1-9*01 were advanced as the Acceptor frameworks.

Three humanized chains were created for each of the two preferred Acceptor frameworks, IGKV3-11*01 and IGKV1-9*01. The three LC1 chains are derived from IGKV3-11*01; the three LC2 chains are derived from IGKV1-9*01. The first humanized chain for each Acceptor framework contained all humanizing substitutions deemed possible and is the most human of the three chains. The second humanized chain for each Acceptor framework contained several back mutations at positions that alter the charge, potentially interfere with the core packing or could affect the conformation of the CDRs. The third chain, for each of the Acceptor frameworks, contained the most back mutations, including substitutions that alter the charge and could potentially alter the binding affinity. The sequences of these six humanized chains are shown below.

LC1_1
(SEQ ID NO: 81)
EIVLTQSPAT LSLSPGERAT LSCRASSSVS YIYWFQQKPG

QAPRLLIYAA FNRATGIPAR FSGSGSGTDY TLTISSLEPE

DFAVYYCQQW SNNPLTFGQG TKVEIK

-continued

LC1_2
(SEQ ID NO: 82)
EIVLTQSPAT LSLSPGERAT LSCRASSSVS YIYWFQQKPG

QSPRPLIYAA FNRATGIPAR FSGSGSGTDY TLTISSLEPE

DFAVYYCQQW SNNPLTFGQG TKVEIK

LC1_3
(SEQ ID NO: 83)
QIVLTQSPAT LSLSPGERAT LSCRASSSVS YIYWFQQKPG

QSPRPLIYAT FNLASGIPAR FSGSGSGTSY TLTISRLEPE

DFAVYYCQQW SNNPLTFGQG TKVEIK

LC2_1
(SEQ ID NO: 84)
DIQLTQSPSS LSASVGDRVT ITCRASSGVS YIYWFQQKPG

KAPKLLIYAA FNLASGVPSR FSGSGSGTEY TLTISSLQPE

DFATYYCQQW SNNPLTFGQG TKVEIK

LC2_2
(SEQ ID NO: 85)
DIQLTQSPSS LSASVGDRVT ITCRASSGVS YIYWFQQKPG

KAPKPLIYAA FNLASGVPSR FSGSGSGTEY TLTISSLQPE

DFATYYCQQW SNNPLTFGQG TKVEIK

LC2_3
(SEQ ID NO: 86)
QIQLTQSPSI LSASVGDRVT ITCRASSSVS YIYWFQQKPG

KAPKPLIYAT FNLASGVPSR FSGSGSGTSY TLTISSLQPE

DFATYYCQQW SNNPLTFGQG TKVEIK

The sequences for these six humanized chains are shown in Table 9 with differences relative to the Parental 3D10 light chain shown in boldface and underline.

TABLE 9

Humanized Light Chains of Antibody 3D10

| Light Chain | SEQ ID NO | Sequence |
|---|---|---|
| LC1_1 | 81 | EIVLTQSPAT LSLSPGERAT LSCRASSSVS YIYWFQQKPG QAPRLLIYAA FNRATGIPAR FSGSGSGTDY TLTISSLEPE DFAVYYCQQW SNNPLTFGQG TKVEIK |
| LC1_2 | 82 | EIVLTQSPAT LSLSPGERAT LSCRASSSVS YIYWFQQKPG QSPRPLIYAA FNRATGIPAR FSGSGSGTDY TLTISSLEPE DFAVYYCQQW SNNPLTFGQG TKVEIK |
| LC1_3 | 83 | QIVLTQSPAT LSLSPGERAT LSCRASSSVS YIYWFQQKPG QSPRPLIYAT FNLASGIPAR FSGSGSGTSY TLTISRLEPE DFAVYYCQQW SNNPLTFGQG TKVEIK |
| LC2_1 | 84 | DIQLTQSPSS LSASVGDRVT ITCRASSGVS YIYWFQQKPG KAPKLLIYAA FNLASGVPSR FSGSGSGTEY TLTISSLQPE DFATYYCQQW SNNPLTFGQG TKVEIK |
| LC2_2 | 85 | DIQLTQSPSS LSASVGDRVT ITCRASSGVS YIYWFQQKPG KAPKPLIYAA FNLASGVPSR FSGSGSGTEY TLTISSLQPE DFATYYCQQW SNNPLTFGQG TKVEIK |
| LC2_3 | 86 | DIQLTQSPSI LSASVGDRVT ITCRASSGVS YIYWFQQKPG KAPKPLIYAT FNLASGVPSR FSGSGSGTSY TLTISSLQPE DFATYYCQQW SNNPLTFGQG TKVEIK |

(B) Humanization of the Heavy Chain

In light of the above-discussed criteria, two candidate germline Acceptor frameworks: IGHV1-2*02 (IGHV1 Germline) and IGHV3-49*04 (IGHV3 Germline) were selected for the humanization of the heavy chain of antibody 3D10.

Acceptor Framework IGHV 1-2*02 was selected due to its sequence similarity to the Parental sequence and the fact that it contained very similar residues involved in the core packing of the domain. Acceptor Framework IGHV3-49*04 was selected after consideration and rejection of other germline sequences similar to IGHV 1-2*02. As Acceptor Framework IGHV3-49*04 is slightly more dissimilar to the Parental sequence than IGHV 1-2*02, a greater number of substitutions were required, however this germline Acceptor framework can support the Parental CDRs. The sequences of Acceptor Framework IGHV 1-2*02 and Acceptor Framework IGHV3-49*04 are shown below:

Acceptor Framework IGHV 1-2*02 (SEQ ID NO: 87):
QVQLVQSGAE VKKPGASVKV SCKASGYTFT GYYMHWVRQA

PGQGLEWMGW INPNSGGTNY AQKFQGRVTM TRDTSISTAY

MELSRLRSDD TAVYYCAR

Acceptor Framework IGHV3-49*04 (SEQ ID NO: 88):
EVQLVESGGG LWQPGRSLRL SCTASGFTFG DYAMSWVRQA

PGKGLEWVGF IRSKAYGGTT EYAASVKGRF TISRDDSKSI

AYLQMNSLKT EDTAVYYCTR

Table 10 shows the alignment of these sequences with the heavy chain of antibody 3D10 (CDR residues of antibody 3D10 are shown in italics, identical aligned residues are shown underlined):

TABLE 10

Alignment of Heavy Chain Variable Regions

| Heavy Chain | SEQ ID NO. | Sequence |
|---|---|---|
| | | 1         10         20         30         40 |
| 3D10 | 10 | EVQLQQSGPD LVTPGASVRI SCQAS*GYTFP* *DYYMN*WVKQS |
| IGHV 1-2*02 | 87 | QVQLVQSGAE VKKPGASVKV SCKASGYTFT GYYMHWVRQA |
| IGHV3-49*04 | 88 | EVQLVESGGG LWQPGRSLRL SCTASGFTFG DYAMSWVRQA |
| | | 41         50         60         70         80 |
| 3D10 | 10 | HGKSLEWIGD *IDP*--*NYGGTTY* *NQKFKG*KAIL TVDRSSSTAY |
| IGHV 1-2*02 | 87 | PGQGLEWMGW INP--NSGGTNY AQKFQGRVTM TRDTSISTAY |
| IGHV3-49*04 | 88 | PGKGLEWVGF IRSKAYGGTTEY AASVKGRFTI SRDDSKSIAY |
| | | 81         90         100        110    114 |
| 3D10 | 10 | MELRSLTSED SAVYYCAR*GA L*TDWGQGTSL TVSS |
| IGHV 1-2*02 | 87 | MELSRLRSDD TAVYYCAR |
| IGHV3-49*04 | 88 | LQMNSLKTED TAVYYCTR |

The J-segment genes were compared to the Parental sequence over FR4, and J-segment IGHJ3*02 (SEQ ID NO:89: DAFDIWGQGTMVTVSS) was selected for the heavy chain.

Three humanized chains were created for each of the two preferred Acceptor frameworks, IGHV1-2*02 and IGHV3-49*04. The three HC1 chains are derived from IGHV1-2*02; the three HC2 chains are derived from IGHV3-49*04). The first humanized chain for each Acceptor framework contained all humanizing substitutions deemed possible and is the most human of the three chains. The second humanized chain for each Acceptor framework contained several back mutations at positions that alter the charge, potentially interfere with the core packing or could affect the conformation of the CDRs. The third chain, for each of the Acceptor frameworks, contained the most back mutations, including substitutions that alter the charge and could potentially alter the binding affinity. The sequences for these six humanized chains are shown below:

```
HC1_1
                                              (SEQ ID NO: 90)
QVQLVQSGAE VKKPGASVKV SCKASGYTFP DYYMNWVRQA

PGQGLEWMGD IDPNYGGTNY AQKFQGRVTM TRDTSISTAY

MELSRLRSDD TAVYYCARGA LTDWGQGTMV TVSS

HC1_2
                                              (SEQ ID NO: 91)
QVQLVQSGAE VKKPGASVKV SCKASGYTFP DYYMNWVRQA

PGQSLEWMGD IDPNYGGTNY NQKFQGRVTM TRDTSISTAY

MELSRLRSDD TAVYYCARGA LTDWGQGTMV TVSS

HC1_3
                                              (SEQ ID NO: 92)
EVQLVQSGAE VKKPGASVKV SCKASGYTFP DYYMNWVRQA

PGQSLEWMGD IDPNYGGTNY NQKFQGRVTM TVDRSSSTAY

MELSRLRSDD TAVYYCARGA LTDWGQGTMV TVSS

HC2_1
                                              (SEQ ID NO: 93)
EVQLVESGGG LVQPGRSLRL SCTASGYTFP DYYMNWVRQA

PGKGLEWVGD IDPNYGGTTY AASVKGRFTI SVDRSKSIAY

LQMSSLKTED TAVYYCTRGA LTDWGQGTMV TVSS

HC2_2
                                              (SEQ ID NO: 94)
EVQLVESGGG LVQPGRSLRL SCTASGYTFP DYYMNWVRQA

PGKGLEWVGD IDPNYGGTTY NASVKGRFTI SVDRSKSIAY

LQMSSLKTED TAVYYCARGA LTDWGQGTMV TVSS

HC2_3
                                              (SEQ ID NO: 95)
EVQLVESGGG LVQPGRSLRL SCTASGYTFP DYYMNWVRQA

PGKGLEWVGD IDPNYGGTTY NQSVKGRFTI SVDRSKSIAY

LQMSSLKTED TAVYYCARGA LTDWGQGTMV TVSS
```

The sequences for these six humanized chains are shown in Table 11 with differences relative to the Parental 3D10 heavy chain shown in boldface and underline.

TABLE 11

| Heavy Chain | SEQ ID NO | Sequence |
|---|---|---|
| HC1_1 | 90 | QVQLVQSGAE VKKPGASVKV SCKASGYTFP DYYMNWVRQA PGQGLEWMGD IDPNYGGTNY AQKFQGRVTM TRDTSISTAY MELSRLRSDD TAVYYCARGA LTDWGQGTMV TVSS |
| HC1_2 | 91 | QVQLVQSGAE VKKPGASVKV SCKASGYTFP DYYMNWVRQA PGQSLEWMGD IDPNYGGTNY NQKFQGRVTM TRDTSISTAY MELSRLRSDD TAVYYCARGA LTDWGQGTMV TVSS |
| HC1_3 | 92 | EVQLVQSGAE VKKPGASVKV SCKASGYTFP DYYMNWVRQA PGQSLEWMGD IDPNYGGTNY NQKFQGRVTM TVDRSSSTAY MELSRLRSDD TAVYYCARGA LTDWGQGTMV TVSS |
| HC2_1 | 93 | EVQLVESGGG LVQPGRSLRL SCTASGYTFP DYYMNWVRQA PGKGLEWVGD IDPNYGGTTY AASVKGRFTI SVDRSKSIAY LQMSSLKTED TAVYYCTRGA LTDWGQGTMV TVSS |
| HC2_2 | 94 | EVQLVESGGG LVQPGRSLRL SCTASGYTFP DYYMNWVRQA PGKGLEWVGD IDPNYGGTTY NASVKGRFTI SVDRSKSIAY LQMSSLKTED TAVYYCARGA LTDWGQGTMV TVSS |
| HC2_3 | 95 | EVQLVESGGG LVQPGRSLRL SCTASGYTFP DYYMNWVRQA PGKGLEWVGD IDPNYGGTTY NQSVKGRFTI SVDRSKSIAY LQMSSLKTED TAVYYCARGA LTDWGQGTMV TVSS |

(C) Humanized Derivatives of Antibody 3D10

A search confirmed that antibodies with a combination of germlines, similar to the pairing of IGKV3-11*01 with IGHV1-2*02, existed. The pairing is labeled Acceptor 1. Additionally, antibodies with a combination of germ lines, similar to the pairing of IGKV 1-9*01 with IGHV3-49*04 were found. The pairing is labeled Acceptor 2.

The above-described light and heavy humanized chains were combined to create 14 variant humanized antibodies, whose sequences are described in Table 12.

TABLE 12

Humanized 3D10 Antibodies

| Antibody | Light Chain | SEQ ID NO. | Heavy Chain | SEQ ID NO. |
|---|---|---|---|---|
| h3D10 Var 1 | LC1_1 | 81 | HC1_1 | 90 |
| h3D10 Var 2 | LC1_2 | 82 | HC1_2 | 91 |
| h3D10 Var 3 | LC1_3 | 83 | HC1_2 | 91 |
| h3D10 Var 4 | LC1_2 | 82 | HC1_3 | 92 |
| h3D10 Var 5 | LC1_3 | 83 | HC1_3 | 92 |
| h3D10 Var 6 | LC2_1 | 84 | HC2_1 | 93 |
| h3D10 Var 7 | LC2_2 | 85 | HC2_2 | 94 |
| h3D10 Var 8 | LC2_3 | 86 | HC2_2 | 94 |
| h3D10 Var 9 | LC2_2 | 85 | HC2_3 | 95 |
| h3D10 Var 10 | LC2_3 | 86 | HC2_3 | 95 |
| h3D10 Var 11 | LC1_1 | 81 | HC2_1 | 93 |
| h3D10 Var 12 | LC2_1 | 84 | HC1_1 | 90 |
| h3D10 Var 13 | LC1_3 | 83 | HC2_3 | 95 |
| h3D10 Var 14 | LC2_3 | 86 | HC1_3 | 92 |

EXAMPLE 5

Production of Humanized Anti-Human PD-1 Antibodies

To illustrate the production of such humanized derivatives, humanized derivatives of anti-human PD-1 antibody 1H3 were produced in accordance with the above-described procedure (a chimeric antibody incorporating the variable region of 1H3 and a human IgG1 Fc region was used as the Parental antibody).

Sequence alignments comparing 1H3 light chain variable domains to the human germ lines were generated using: IGKV3 light chain germlines (IGKV3-11*01, IGKV3-11*02, IGKV3D-11*01, IGKV3D-20*01, IGKV3-NL4*01, IGKV3D-7*01, IGKV3-20*01, IGKV3-NL5*01, IGKV3-15*01, IGKV3-NL1*01, IGKV3-20*01, IGKV3-NL2*01, IGKV3-NL3*01), IGKV1 light chain germlines (IGKV1-9*01, IGKV1D-43*01, IGKV1-39*01, IGKV1D-13*02, IGKV1-8*01, IGKV1D-13*01, IGKV1-12*01, IGKV1D-16*01, IGKV1-5*01, and IGKV1-NL1*01) and IGKJ light chain germlines (IGKJ2*02, IGKJ2*01, IGKJ2*04, IGKJ2*03, IGKJ5*01, IGKJ4*01, IGKJ3*01, and IGKJ1*01).

Sequence alignments comparing 1H3 heavy chain variable domains to the human germ lines were generated using: IGHV3 heavy chain germlines (IGHV3-48*01, IGHV3-48*02, IGHV3-48*03, IGHV3-11*01, IGHV3-21*01, IGHV3-11*03, IGHV3-30*03, IGHV3-9*01, IGHV3-7*01, and IGHV3-30*10), IGHV1 heavy chain germlines (IGHV1-3*01, IGHV1-69*08, IGHV1-69*11, IGHV1-46*01, IGHV1-69*05, IGHV1-69*06, IGHV1-69*01, IGHV1-46*02, IGHV1-69*02, and IGHV1-69*10), and IGHJ heavy chain germlines (IGHJ6*01, IGHJ6*03, IGHJ4*01, IGHJ6*04, IGHJ5*02, IGHJ3*02, IGHJ5*01, IGHJ3*01, IGHJ2*01, and IGHJ1*01).

Based on overall sequence identity, matching interface positions and similarly classed CDR canonical positions, two germline families were identified for each of the light and heavy chain as possible Acceptor frameworks (IGKV3 and IGKV1 for the light chain and IGHV3 and IGHV1 for the heavy chain). Antibody 1H3 was found to be most similar to the light chain germline 1GKV3-11*01 and heavy IGHV3-48*01. Based on overall sequence identity, matching interface positions and similarly classed CDR canonical positions, two germline families were identified for each of the light and heavy chain as possible Acceptor frameworks (IGKV3 and IGKV1 for the light chain and IGHV3, IGHV1 for the heavy chain.

(A) Humanization of the Light Chain

Antibody 1H3 has a short 10 residue CDR L1 and falls into canonical class I. No human germ line has such a short CDR L1, but the closest germlines in each selected family (IGKV3-II*01 and IGKV1-9*01 have short L1 loops and contain the correct framework residues to support a class I LI loop. The overall sequence similarity was good for both Acceptor frameworks; however there are differences at two interface positions (Y33 and P45). Y33 lies in CDR L1 and while the two Acceptor families do not contain tyrosine at this position other potential acceptor families do. The difference at P45 was tied in with a number of other differences in FR2 of the Parental light chain. In short, the Parental germline belongs to a mouse germline family with a FR2 dissimilar to anything in the human germlines.

Germ lines 1GKV3-11*01 and IGKV 1-9*01 were selected as light chain Acceptor frameworks. The sequences of the light chains of 1GKV3-11*01 and IGKV 1-9*01 are shown above as SEQ ID NO:78 and SEQ ID NO:79, respectively. The alignments of these sequences with the light chain of antibody 1H3 are shown in Table 13 (CDR residues of antibody 1H3 are shown in italics, identical aligned residues are shown underlined):

TABLE 13

Alignment of Light Chain Variable Regions

| Light Chain | SEQ ID NO. | Sequence |
|---|---|---|
|  |  | 1          10          20          30          40 |
| 1H3 | 15 | QIVLTQSPAL MSASPGEKVT MTC*SASSSVS YMY*WYQQKPR |
| IGKV3-11*01 | 78 | EIVLTQSPAT LSLSPGERAT LSCRASQSVSS YLAWYQQKPG |
| IGKV1-9*01 | 79 | DIQLTQSPSF LSASVGDRVT ITCRASQGISS YLAWYQQKPG |
|  |  | 41         50          60         70         80 |
| 1H3 | 15 | SSPKPWIY*LT SNLAS*GVPAR FSGSGSGTSY SLTISSMEAE |
| IGKV3-11*01 | 78 | QAPRLLIYDA SNRATGIPAR FSGSGSGTDF TLTISSLEPE |
| IGKV1-9*01 | 79 | KAPKLLIYAA STLQSGVPSR FSGSGSGTEF TLTISSLQPE |

TABLE 13-continued

Alignment of Light Chain Variable Regions

| Light Chain | SEQ ID NO. | Sequence |
|---|---|---|
| | | 81        90         100    106 |
| 1H3 | 15 | DAATYYCQQW SSNPFTFGSG TKLEIK |
| IGKV3-11*01 | 78 | D_F_AV_YY_C_QQ_R _S_N_W_P------ ------ |
| IGKV1-9*01 | 79 | D_F_AT_YY_C_QQ_L _N_S_Y_P------ ------ |

The J-segment genes were compared to the Parental sequence over FR4, and J-segment IGKJ2*02 (SEQ ID NO:96: CTFGQGTKLEIK) was selected for the light chain.

Two humanized chains were created for each of the two preferred Acceptor frameworks, IGKV3-11*01 and IGKV1-9*01. The two LC1 chains are derived from IGKV3-11*01; the two LC2 chains are derived from IGKV1-9*01. The first humanized chain for each Acceptor framework contained all humanizing substitutions deemed possible and is the most human of the three chains. The second humanized chain for each Acceptor framework contained several back mutations at positions that alter the charge, potentially interfere with the core packing or could affect the conformation of the CDRs. The sequences of these four humanized chains are shown below:

LC1_1
(SEQ ID NO: 97)
EIVLTQSPAT LSLSPGERAT LSCRASSSVS YMYWYQQKPG

QAPRLLIYLA SNRATGIPAR FSGSGSGTDY TLTISSLEPE

DFAVYYCQQW SSNPFTFGQG TKLEIK

LC1_2
(SEQ ID NO: 98)
QIVLTQSPAT LSLSPGERAT LSCSASSSVS YMYWYQQKPG

QAPRLLIYLT SNRATGIPAR FSGSGSGTDY TLTISSLEPE

DFAVYYCQQW SSNPFTFGQG TKLEIK

LC2_1
(SEQ ID NO: 99)
DIQLTQSPSS LSASVGDRVT ITCRASSSVS YMYWYQQKPG

KAPKLLIYLA SNLASGVPSR FSGSGSGTEY TLTISSLEPE

DFATYYCQQW SSNPFTFGQG TKLEIK

LC2_2
(SEQ ID NO: 100)
QIQLTQSPSS LSASVGDRVT ITCSASSSVS YMYWYQQKPG

KAPKLLIYLT SNLASGVPSR FSGSGSGTEY TLTISSLEPE

DFATYYCQQW SSNPFTFGQG TKLEIK

The sequences for these four humanized chains are shown in Table 14 with differences relative to the Parental 1H3 Var1 light chain shown in boldface and underline.

TABLE 14

Humanized Light Chains of Antibody 1H3

| Light Chain | SEQ ID NO | Sequence |
|---|---|---|
| LC1_1 | 97 | EIVLTQSPAT LSLSPGERAT LSCRASSSVS YMYWYQQKPG QAPRLLIYLA SNRATGIPAR FSGSGSGTDY TLTISSLEPE DFAVYYCQQW SSNPFTFGQG TKLEIK |
| LC1_2 | 98 | QIVLTQSPAT LSLSPGERAT LSCSASSSVS YMYWYQQKPG QAPRLLIYLT SNRATGIPAR FSGSGSGTDY TLTISSLEPE DFAVYYCQQW SSNPFTFGQG TKLEIK |
| LC2_1 | 99 | DIQLTQSPSS LSASVGDRVT ITCRASSSVS YMYWYQQKPG KAPKLLIYLA SNLASGVPSR FSGSGSGTEY TLTISSLEPE DFATYYCQQW SSNPFTFGQG TKLEIK |
| LC2_2 | 100 | QIQLTQSPSS LSASVGDRVT ITCSASSSVS YMYWYQQKPG KAPKLLIYLT SNLASGVPSR FSGSGSGTEY TLTISSLEPE DFATYYCQQW SSNPFTFGQG TKLEIK |

(B) Humanization of the Heavy Chain

In light of the above-discussed criteria, two candidate germline Acceptor frameworks: IGHV3-48*01 (IGHV3 Germline) and IGHV1-3*01 (IGHV1 Germline) were selected for the humanization of the heavy chain of antibody 1H3 Var1.

Acceptor Framework 1GHV3-48*01 was selected as the primary heavy Acceptor framework due to its overall sequence similarity. The interface residues match except for H35, a position at where some variation is allowed and it contains the correct residues for determining canonical class for CDR H1. CDR H2 does not fall into any sequence-based canonical class due to a tyrosine at position 56. The choice of the second heavy chain Acceptor framework was made after removing any germ line closely related to IGHV3-48*01. The closest germ line then became IGHV1-3*01. The number of differences to take into account becomes larger as the packing of the lower core is different, however the germline should support the CDRs and function as a suitable Acceptor framework. It was noted that the Parental sequence contains a cysteine at the conserved position 60, where all human germlines have a tyrosine. The sequences of Acceptor Framework 1 GHV3-48*01 and Acceptor Framework IGHV1-3*01 are shown below:

```
Acceptor Framework 1GHV3-48*01 (SEQ ID NO: 101):
EVQLVESGGG LVQPGGSLRL SCAASGFTFS SYSMNWVRQA

PGKGLEWVSY ISSSSSTIYY ADSVKGRFTI SRDNAKNSLY

LQMNSLRAED TAVYYCAR

Acceptor Framework IGHV1-3*01 (SEQ ID NO: 102):
QVQLVQSGAE VKKPGASVKV SCKASGYTFT SYAMHWVRQA

PGQRLEWMGW INAGNGNTKY SQKFQGRVTI TRDTSASTAY

MELSSLRSED TAVYYCAR
```

Table 15 shows the alignment of these sequences with the heavy chain of antibody 1H3 (CDR residues of antibody 1H3 are shown in italics, identical aligned residues are shown underlined):

TABLE 15

Alignment of Heavy Chain Variable Regions

| Heavy Chain | SEQ ID NO. | Sequence |
|---|---|---|
| | | 1          10         20         30         40 |
| 1H3 | 16 | EVQLVESGGG LVKPGGSLKL SCAAS*GFTFS* *DYGMH*WVRQA |
| IGHV3-48*01 | 101 | EVQLVESGGG LVQPGGSLRL SCAASGFTFS SYSMNWVRQA |
| IGHV1-3*01 | 102 | QVQLVQSGAE VKKPGASVKV SCKASGYTFT SYAMHWVRQA |
| | | 41         50         60         70         80 |
| 1H3 | 16 | PEKGLEWVA*y* *ISSGSYTIyy* *TDTVKG*RFTI SRDNAKNTLF |
| IGHV3-48*01 | 101 | PGKGLEWVSY ISSSSSTIYY ADSVKGRFTI SRDNAKNSLY |
| IGHV1-3*01 | 102 | PGQRLEWMGW INAGNGNTKY SQKFQGRVTI TRDTSASTAY |
| | | 81         90        100        110        120 |
| 1H3 | 16 | LQMTSLRSED TAMYYCAR*RG* *YGSFYEYYFD* *y*WGQGTTLTV SS |
| IGHV3-48*01 | 101 | LQMNSLRAED TAVYYCAR |
| IGHV1-3*01 | 102 | MELSSLRSED TAVYYCAR |

The J-segment genes were compared to the Parental sequence over FR4, and J-segment IGHJ6*01 (SEQ ID NO:103: WGQGTTVTV) was selected for the heavy chain.

Three humanized chains were created for each of the two preferred Acceptor frameworks, IGHV3-48*01 and IGHV1-3*01. The three HC1 chains are derived from IGHV3-48*01; the three HC2 chains are derived from IGHV1-3*01). The first humanized chain for each Acceptor framework contained all humanizing substitutions deemed possible and is the most human of the three chains. The second humanized chain for each Acceptor framework contained several back mutations at positions that alter the charge, potentially interfere with the core packing or could affect the conformation of the CDRs. The third chain, for each of the Acceptor frameworks, contained the most back mutations, including substitutions that alter the charge and could potentially alter the binding affinity. The sequences of these six humanized chains are shown below:

```
HC1_1
                                         (SEQ ID NO: 104)
EVQLVESGGG LVQPGGSLRL SCAASGFTFS DYGMHWVRQA

PGKGLEWVSY ISSGSSTIYY ADSVKGRFTI SRDNAKNTLY

LQMSSLRAED TAVYYCARRG YGSFYEYYFD YWGQGTTVTV

SS

HC1_2
                                         (SEQ ID NO: 105)
EVQLVESGGG LVQPGGSLRL SCAASGFTFS DYGMHWVRQA

PGKGLEWVAY ISSGSYTIYY ADSVKGRFTI SRDNAKNTLY

LQMSSLRAED TAVYYCARRG YGSFYEYYFD YWGQGTTVTV

SS

HC1_3
                                         (SEQ ID NO: 106)
EVQLVESGGG LVQPGGSLRL SCAASGFTFS DYGMHWVRQA

PGKGLEWVAY ISSGSYTIYS ADSVKGRFTI SRDNAKNTLY

LQMSSLRAED TAVYYCARRG YGSFYEYYFD YWGQGTTVTV

SS

HC2_1
                                         (SEQ ID NO: 107)
QVQLVQSGAE VKKPGASVKV SCKASGFTFS DYGMHWVRQA

-continued

PGQRLEWMGY ISSGSSTIYY SQKFQGRVTI TRDNSASTLY

MELSSLRSED TAVYYCARRG YGSFYEYYFD YWGQGTTLTV

SS
```

-continued

HC2_2
(SEQ ID NO: 108)
EVQLVQSGAE VKKPGASVKV SCAASGFTFS DYGMHWVRQA

PGQRLEWMGY ISSGSYTIYY SQKFQGRVTI TRDNSASTLY

MELSSLRSED TAVYYCARRG YGSFYEYYFD YWGQGTTLTV

SS

HC2_3
(SEQ ID NO: 109)
EVQLVQSGAE VKKPGASVKV SCAASGFTFS DYGMHWVRQA

PGQRLEWVAY ISSGSYTIYY SQKFQGRVTI TRDNSASTLY

MELSSLRSED TAVYYCARRG YGSFYEYYFD YWGQGTTLTV

SS

The sequences for these six humanized chains are shown in Table 16 with differences relative to the Parental 1H3 heavy chain shown in boldface and underline.

TABLE 16

Humanized Heavy Chains of Antibody 3H1

| Heavy Chain | SEQ ID NO | Sequence |
|---|---|---|
| HC1_1 | 104 | EVQLVESGGG LVQPGGSLRL SCAASGFTFS DYGMHWVRQA PGKGLEWVSY ISSGSSTIYY ADSVKGRFTI SRDNAKNTLY LQMSSLRAED TAVYYCARRG YGSFYEYYFD YWGQGTTVTV SS |
| HC1_2 | 105 | EVQLVESGGG LVQPGGSLRL SCAASGFTFS DYGMHWVRQA PGKGLEWVAY ISSGSYTIYY ADSVKGRFTI SRDNAKNTLY LQMSSLRAED TAVYYCARRG YGSFYEYYFD YWGQGTTVTV SS |
| HC1_3 | 106 | EVQLVESGGG LVQPGGSLRL SCAASGFTFS DYGMHWVRQA PGKGLEWVAY ISSGSYTIYS ADSVKGRFTI SRDNAKNTLY LQMSSLRAED TAVYYCARRG YGSFYEYYFD YWGQGTTVTV SS |
| HC2_1 | 107 | QVQLVQSGAE VKKPGASVKV SCKASGFTFS DYGMHWVRQA PGQRLEWMGY ISSGSSTIYY SQKFQGRVTI TRDNSASTLY MELSSLRSED TAVYYCARRG YGSFYEYYFD YWGQGTTLTV SS |
| HC2_2 | 108 | EVQLVQSGAE VKKPGASVKV SCAASGFTFS DYGMHWVRQA PGQRLEWMGY ISSGSYTIYY SQKFQGRVTI TRDNSASTLY MELSSLRSED TAVYYCARRG YGSFYEYYFD YWGQGTTLTV SS |
| HC2_3 | 109 | EVQLVQSGAE VKKPGASVKV SCAASGFTFS DYGMHWVRQA PGQRLEWVAY ISSGSYTIYY SQKFQGRVTI TRDNSASTLY MELSSLRSED TAVYYCARRG YGSFYEYYFD YWGQGTTLTV SS |

(C) Humanized Derivatives of Antibody 1H3

A search confirmed that antibodies with a combination of germlines close to the pairing of IGKV3-11*01 with heavy IGHV3-48*01 exist. The pairing is labeled Acceptor 1. Subsequently, antibodies with a similar pairing to IGKVI-9*01 with IGHVI-3*01 were found. The pairing is labeled Acceptor 2.

The above-described light and heavy humanized chains were combined to create 14 variant humanized antibodies, whose sequences are described in Table 17.

TABLE 17

Humanized 1H3 Antibodies

| Antibody | Light Chain | SEQ ID NO. | Heavy Chain | SEQ ID NO. |
|---|---|---|---|---|
| h1H3 Var 1 | LC1_1 | 97 | HC1_1 | 104 |
| h1H3 Var 2 | LC1_1 | 97 | HC1_2 | 105 |
| h1H3 Var 3 | LC1_1 | 97 | HC1_3 | 106 |
| h1H3 Var 4 | LC1_2 | 98 | HC1_1 | 104 |
| h1H3 Var 5 | LC1_2 | 98 | HC1_2 | 105 |
| h1H3 Var 6 | LC1_2 | 98 | HC1_3 | 106 |
| h1H3 Var 7 | LC2_1 | 99 | HC2_1 | 107 |
| h1H3 Var 8 | LC2_1 | 99 | HC2_2 | 108 |
| h1H3 Var 9 | LC2_1 | 100 | HC2_3 | 109 |
| h1H3 Var 10 | LC2_2 | 100 | HC2_1 | 107 |
| h1H3 Var 11 | LC2_2 | 99 | HC2_2 | 108 |
| h1H3 Var 12 | LC2_2 | 99 | HC2_2 | 108 |
| h1H3 Var 13 | LC1_1 | 96 | HC2_1 | 107 |
| h1H3 Var 14 | LC2_1 | 98 | HC1_1 | 104 |

EXAMPLE 6

Characterization of 1H3 Anti-Human PD-1 Antibody

In order to evaluate the properties of the anti-PD-1 antibodies of the present invention, a construct was produced which possesses chimeric ("ch") murine anti-human PD-1 Fab regions of antibody 1H3 and a human IgG1 Fc region (1H3 Construct). The construct was tested for its ability to bind human PD-1.

Figure 12:
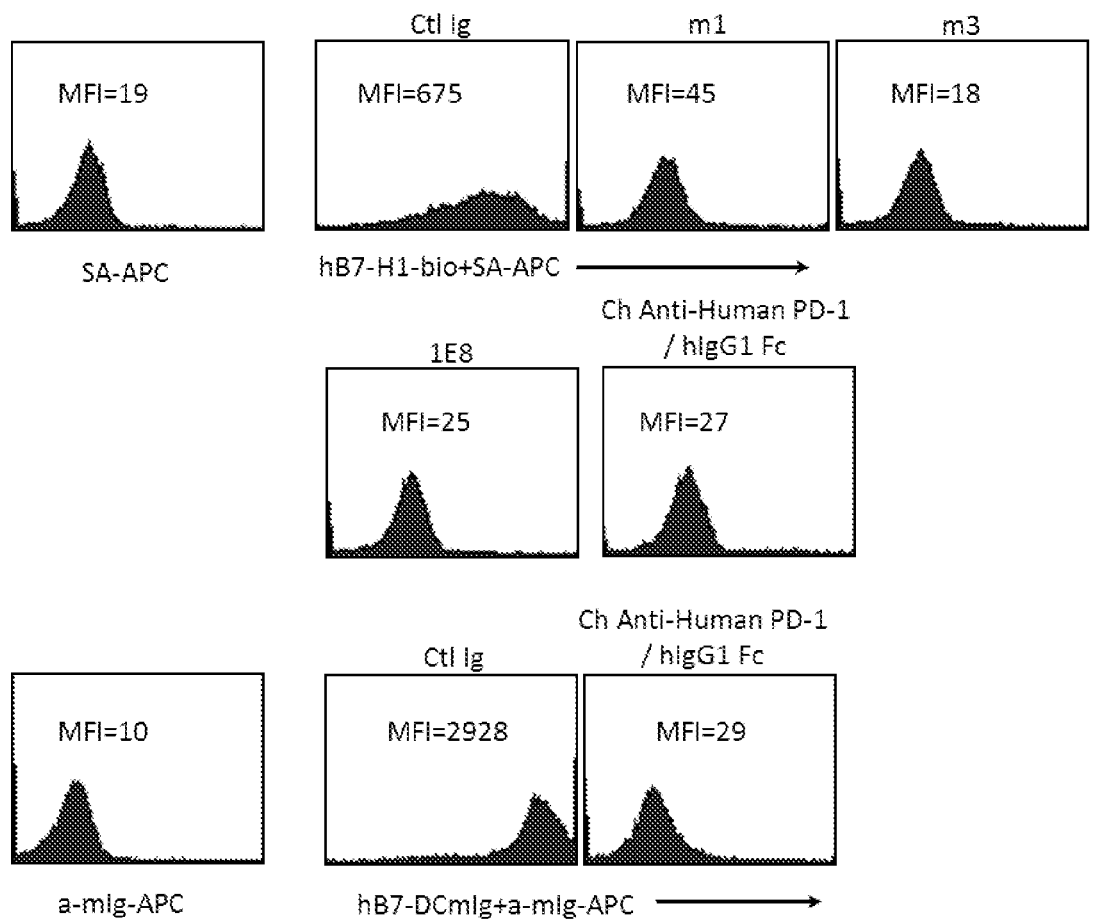
FIG. 12 shows the results of an experiment in which CHO cells transfected with human full length PD-1 were pre-incubated with a saturating dose of anti-human PD-1 monoclonal antibodies (mAbs) or control Ig before being stained by biotin-labeled hB7-H1-FC or hB7-DC mIg.

FIG. 12 shows the results of an experiment in which CHO cells transfected with human full length PD-1 were pre-incubated with a saturated dose of PD-1 mAbs before being stained by biotin-labeled anti-hB7-H1-Fc or anti-hB7-DC mFc. FIG. 12, shows that a murine monoclonal antibody construct which possesses chimeric ("ch") murine anti-human PD-1 Fab regions of antibody 1H3 and a human IgG1 Fc region blocks binding of B7-H1-Fc and B7-DC-Fc to cells expressing human PD-1, as a result of antibody binding to the cells. M1, m3 and 1E8 are all positive control anti-PD-1 antibodies. On non-reducing gels, the Construct migrated as a single band of approximately 200 MW; this band was replaced with band at approximately 52 MW under reducing conditions.

Figure 13:
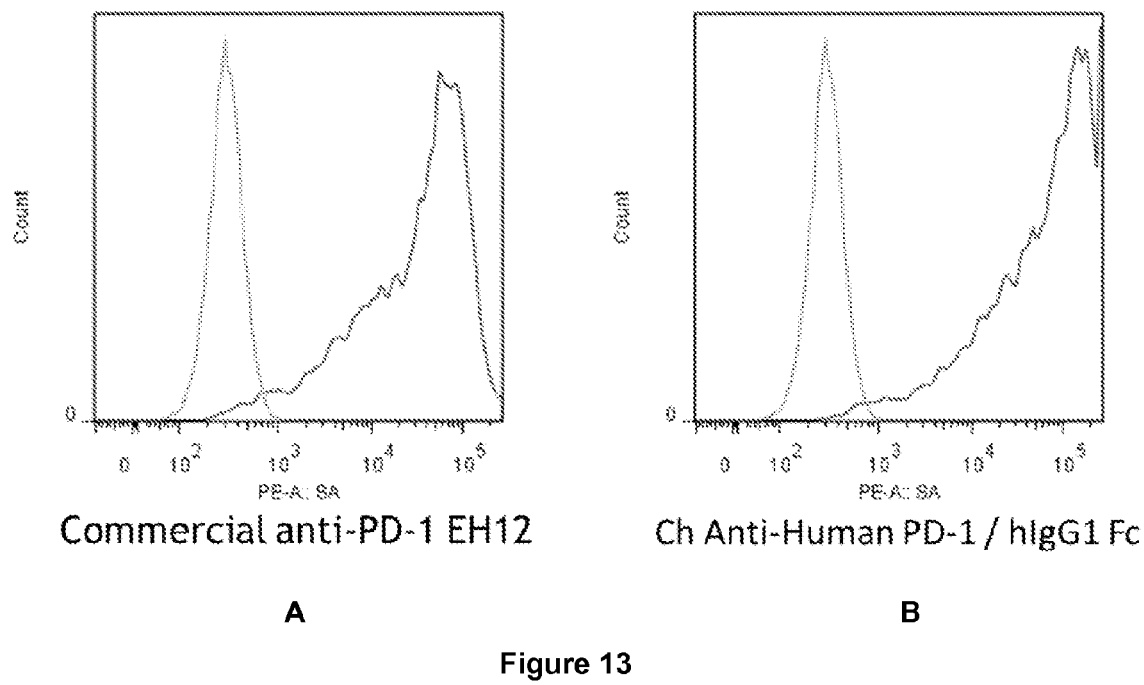
FIG. 13, Panels A-B show the comparative binding of: (A) the commercially available anti-PD-1 antibody, EH12 with (B) a murine monoclonal antibody which possesses chimeric ("ch") murine anti-human PD-1 Fab regions and a human IgG1 Fc region.
Figure 14:
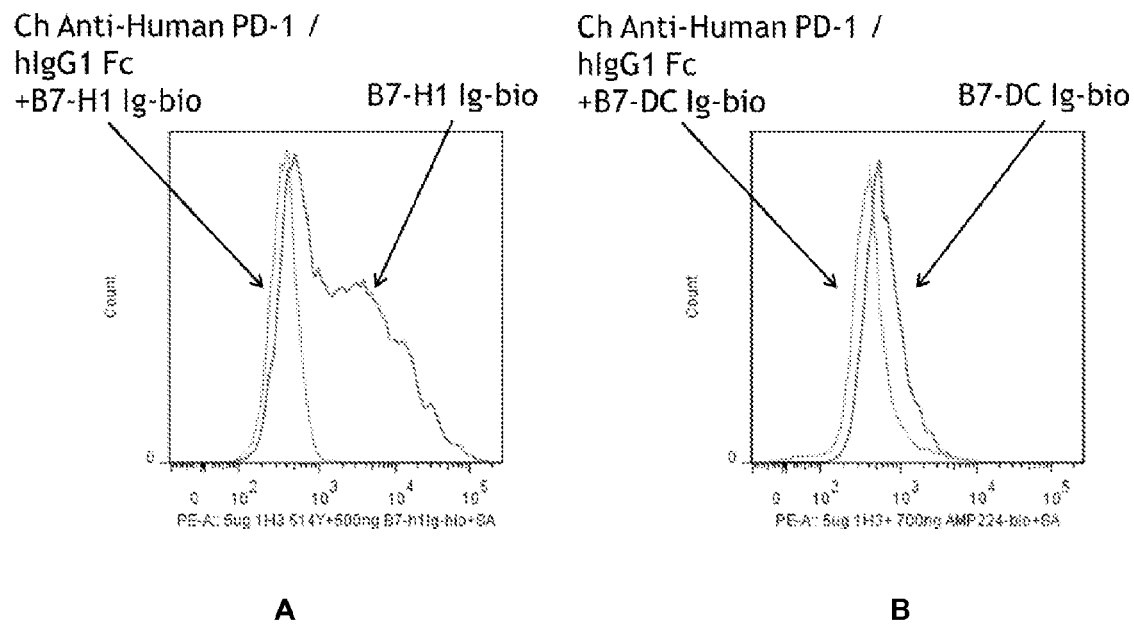
FIG. 14, Panels A-B show the ability of the anti-PD-1 antibodies of the present invention to exert a blocking effect on biotinylated B7-H1-Fc and biotinylated B7-DC-Fc binding to PD-1.
Figure 15:
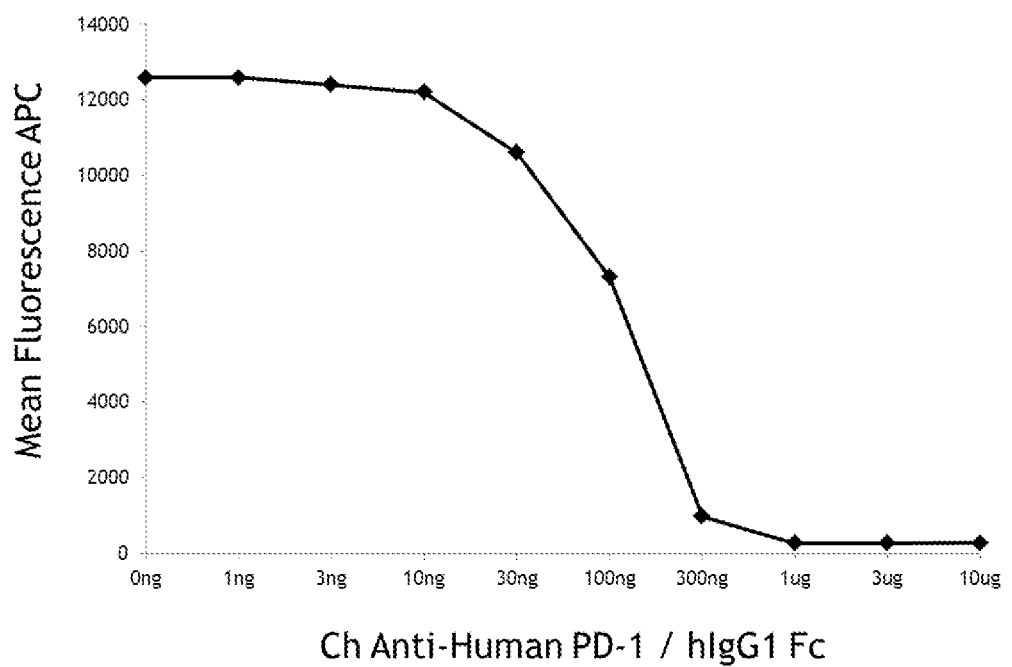
FIG. 15 shows that a binding curve of 1H3 anti-human PD-1 chimeric antibody to CHO.hPD-1 cells, as detected by anti-hIg antibody.

The 1H3 Construct exhibited an Affinity $K_D$ of 2.19 nM, an "on rate" $K_a$ of $0.734 \times 10^{-5}$/Ms, and an "off rate" $K_d$ of $1.61 \times 10^{-4}$/s. The $EC_{50}$ of the construct was found to be 75 ng. FIG. 13 compares the binding obtained with this construct to that of the commercially available anti-PD-1 antibody, EH12. The construct was found to be capable of completely blocking the ability of hPD-1 (expressed by CHO cells) to bind to B7-H1-Fc or B7-DC-Fc as shown in FIG. 14. FIG. 15 shows that the chimeric 1H3 Construct was able to bind to hPD-1-Fc and block the binding of such hPD-1-Fc to hB7-H1 expressed by CHO cells.

Figure 16A:
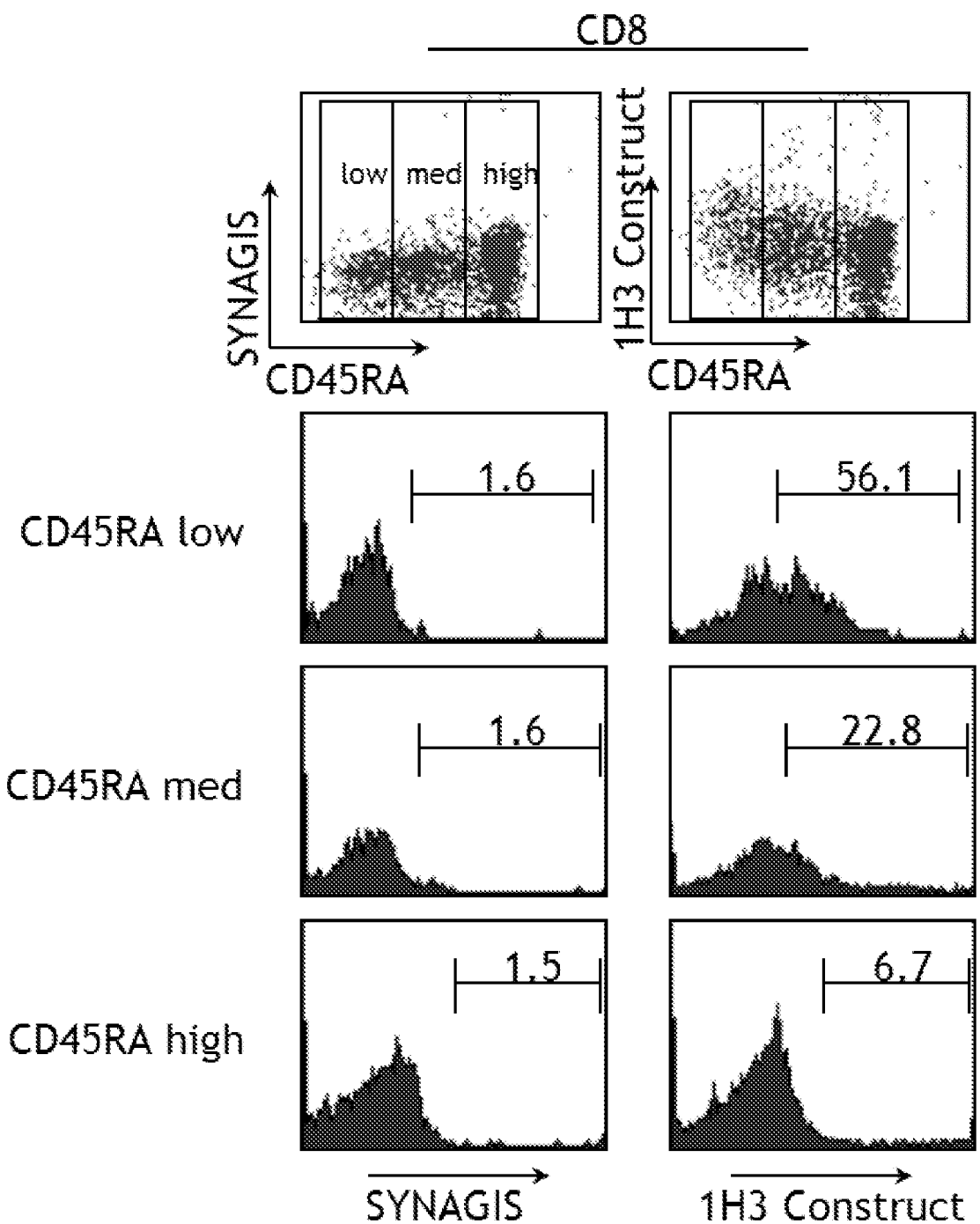
FIGS. 16A-16B shows the results of studies of the ability of the 1H3 anti-human PD-1 chimeric antibody to bind to human primary T cells CD8+ (FIG. 16A) and CD4+ (FIG. 16B) relative to the negative control antibody (palivizumab; SYNAGIS®, Medimmune, Inc.).
Figure 16B:
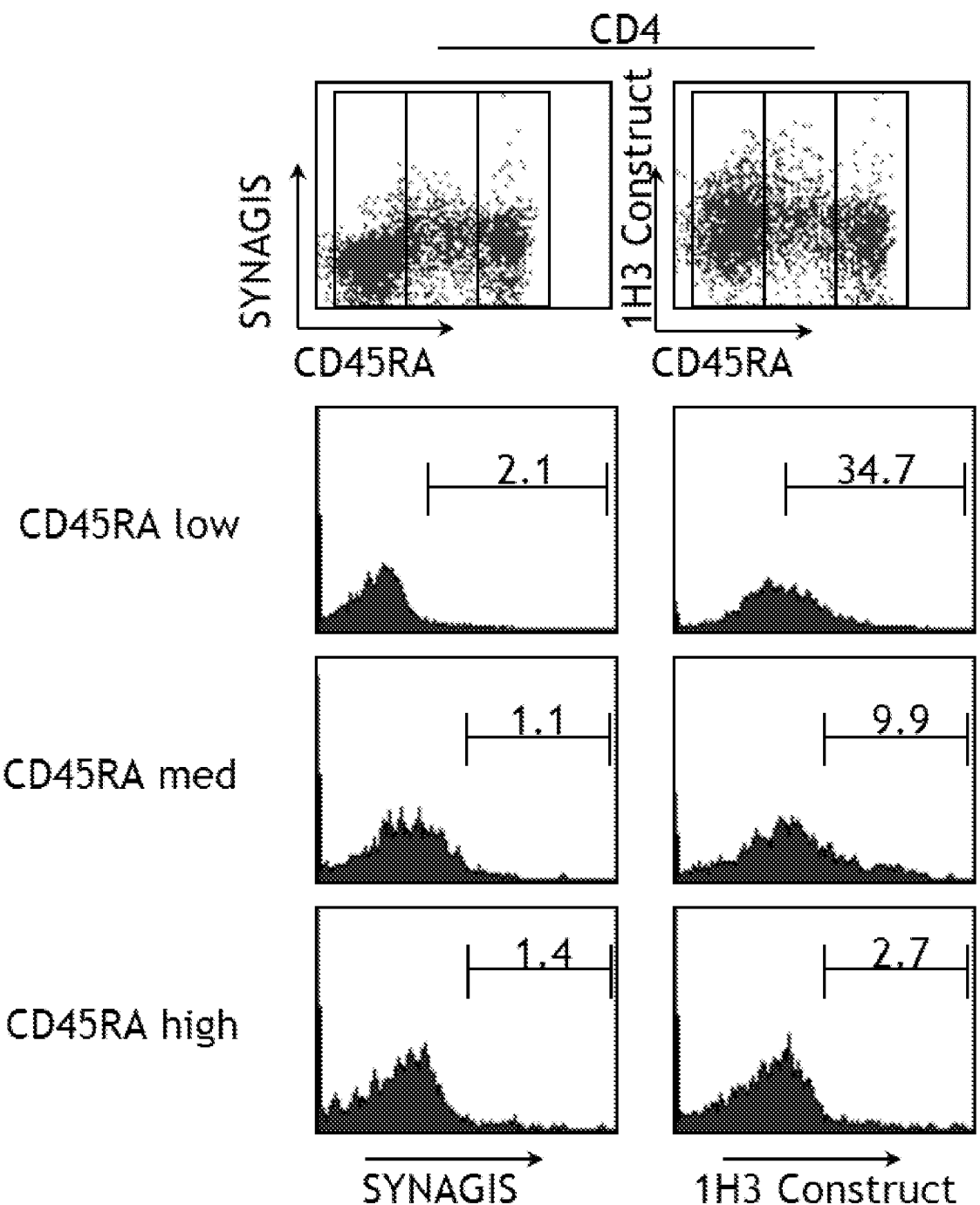

The ability of the 1H3 Construct to bind to human primary T cells was assessed relative to a control antibody (palivizumab; SYNAGIS®, Medimmune, Inc.); 1H3 demonstrated enhanced binding to both CD8 and CD4 cells (FIGS. 16A-16B).

Figure 17:
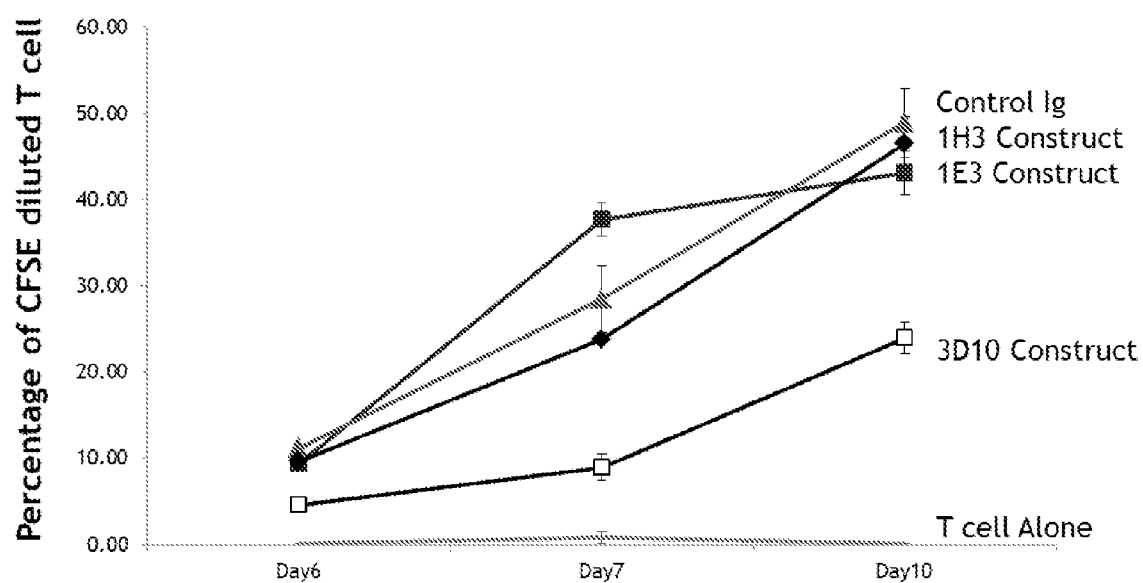
FIG. 17 shows the ability of the antibodies of the present invention to enhance antigen specific T cell response as measured by CFSE dilution upon tetanus toxin (TT) recall.
Figure 18A:
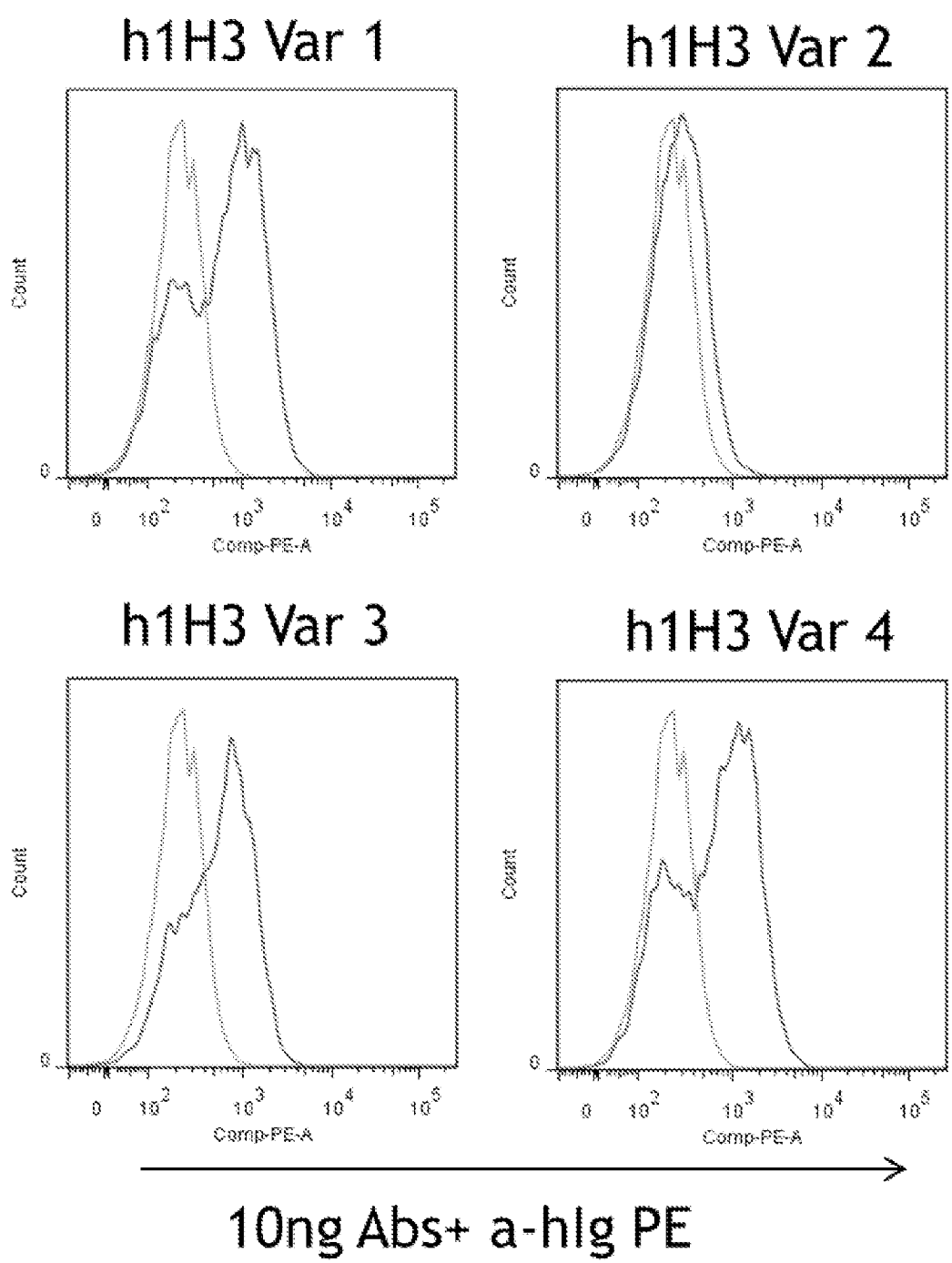
FIGS. 18A-18D demonstrate the ability of the humanized 1H3 Variants (h1H3 Var 1-h1H3 Var 14 to bind to CHO.hPD1 cells.
Figure 18B:
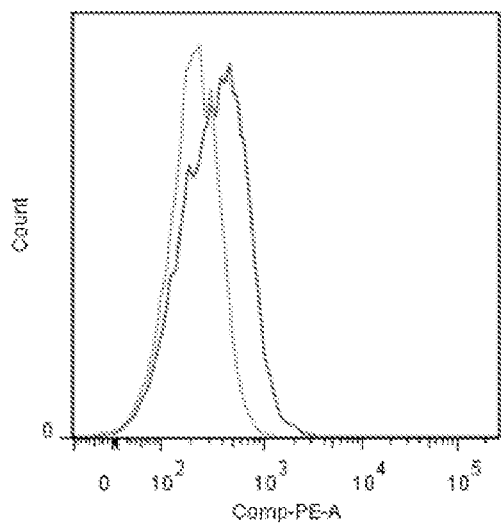
Figure 18B:
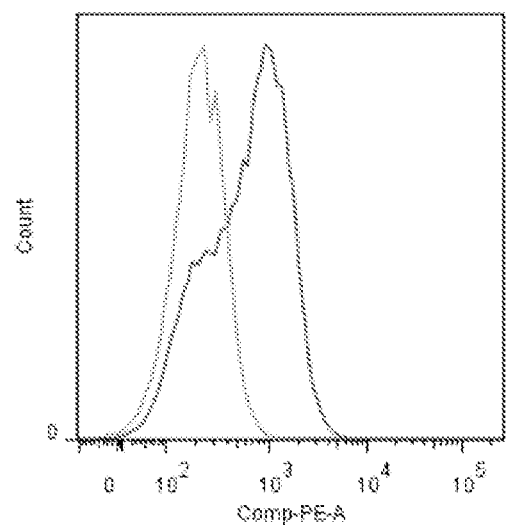
Figure 18B:
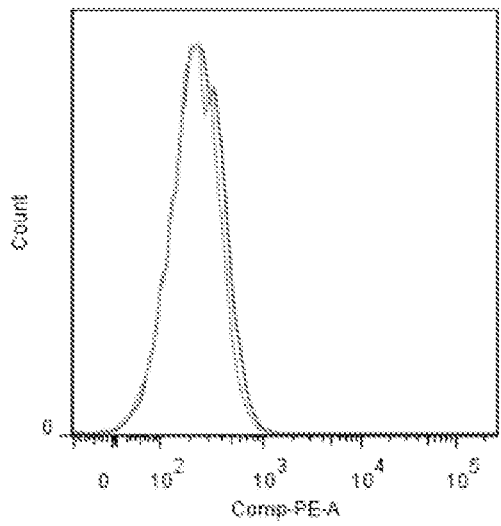
Figure 18B:
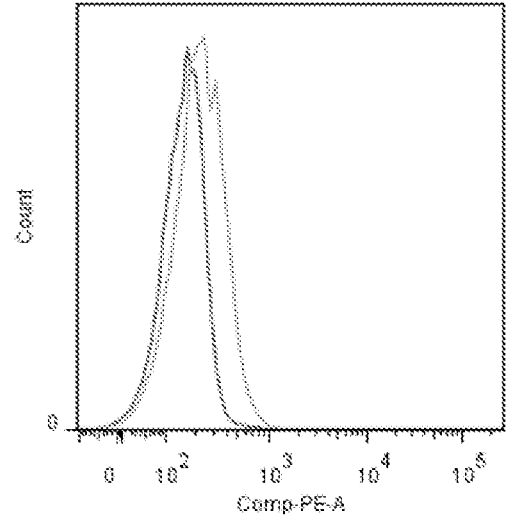
Figure 18C:
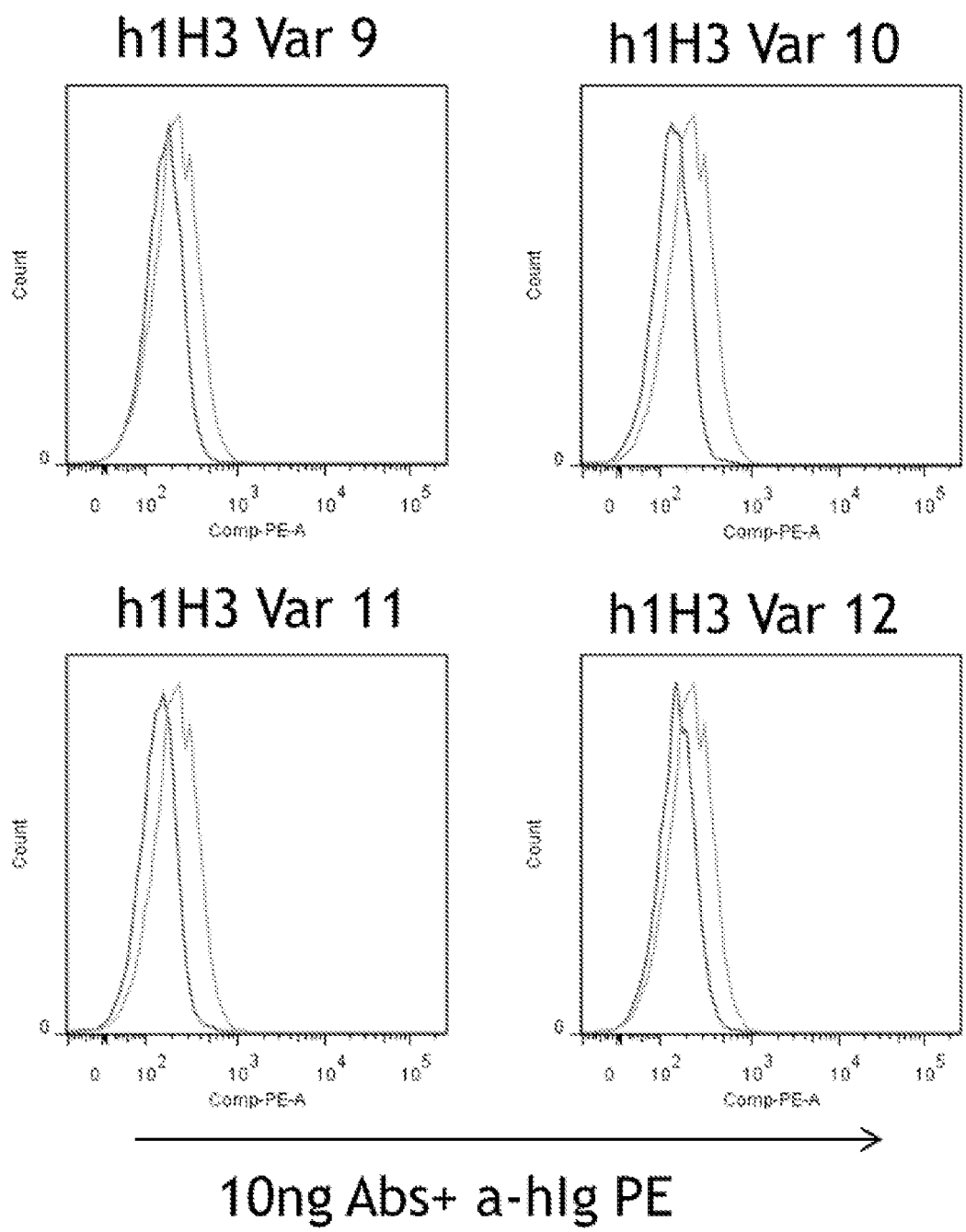
Figure 18D:
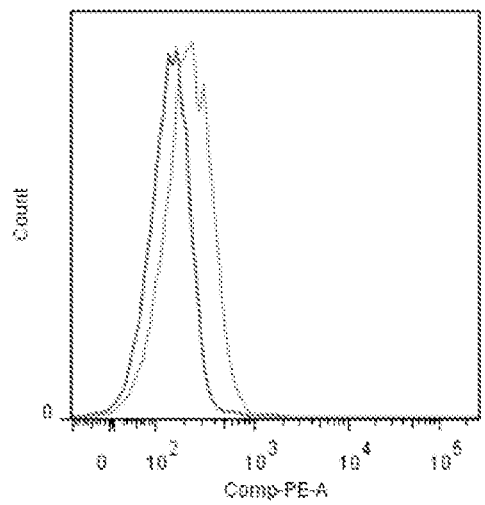
Figure 18D:
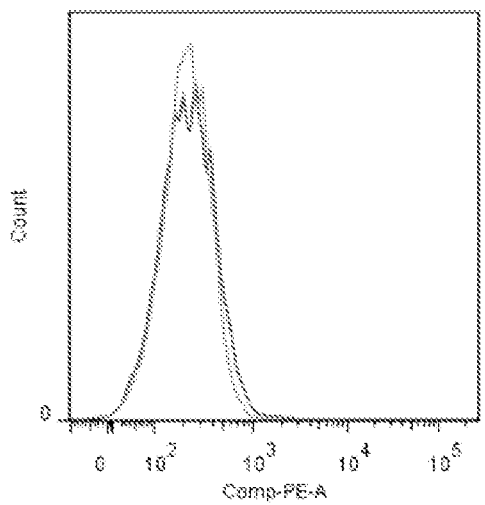
Figure 18D:
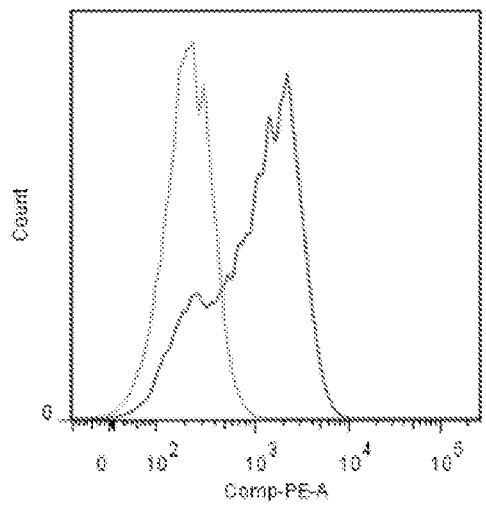

To illustrate the functional characteristics of the antibodies of the present invention, the ability of Construct 1H3, and of chimeric antibody constructs having the FAB regions of antibody 1H3 ("1H3 Construct"), 1E3 ("1E3 Construct"), and antibody 3D10 ("3D10 construct") to enhance T cell activity was assessed. Immature dendritic cells (DC) were exposed to TNFα and PGE2 for two days (cells were incubated in the presence of 50 μg/ml tetanus toxoid (TT) overnight at the second day of maturation). The resultant cells were found to have become mature DC as determined by their acquired ability to express B7-H1 and B7-DC. The matured DC cells were then incubated for two weeks in the presence of carboxyfluorescein succinimidyl ester (CFSE)-labeled autologous T cells and 100 ng/ml TT and the above-described antibody constructs. As shown in FIG. 17, the antibodies of the present invention were capable of block B7-H1-PD-1 interactions as measured by expansion of antigen-specific memory T cells. At Day 7, an analysis of the cytokines present in the cell supernatants was conducted (Table 18).

TABLE 18

| Cytokine (pg/ml) | Control Ig | 1H3 Construct | 1E3 Construct | 3H10 Construct |
|---|---|---|---|---|
| G-CSF | 8.04 | 18.41 | 17.39 | 20.40 |
| GM-CSF | 35.12 | 379.05 | 162.30 | 445.78 |
| IFN-γ | 61.78 | 5967.64 | 1247.81 | 5337.78 |
| IL-2 | 12.72 | 12.25 | 9.45 | 13.96 |
| IL-4 | 3.16 | 9.93 | 6.98 | 9.59 |
| IL-5 | 3.51 | 31.34 | 9.40 | 110.40 |
| IL-6 | 125.40 | 418.24 | 134.56 | 124.31 |
| IL-7 | 7.88 | 21.81 | 13.67 | 11.93 |
| IL-8 | 5027.28 | 7978.03 | 5010.73 | 4292.56 |
| IL-10 | 6.99 | 29.45 | 15.30 | 18.33 |
| IL-12p70 | 23.18 | 106.55 | 74.84 | 110.13 |
| IL-13 | 18.90 | 378.05 | 79.33 | 738.62 |
| IL-17 | 368.98 | 503.01 | 407.81 | 421.37 |
| MCP-1 | 2174.36 | 9954.89 | 4792.30 | 5895.81 |
| MIP-1β* | 1453.85 | 5750.63 | 9197.32 | 8511.53 |
| TNF-α | 51.75 | 486.39 | 353.89 | 949.85 |

*day 6

As shown in Table 18, both of the anti-hPD-1 antibody constructs promoted both Th1 and Th2 responses. Very low amount of IL-10, IL-2, IL-4, IL-7, IL-10 and G-CSF were found in the supernatants. All mAbs have very low endotoxin, less than 0.01 EU/mg; additionally, the DC and T cells were kept in serum-free media. Intracellular IFN-γ staining of Day 7 cells revealed that whereas only 0.15% of control cells were IFN-γ⁺, 1.9% of cells that had been incubated with the 1H3 Construct, 0.91% of cells that had been incubated with the 1E3 Construct, and 3.2% of cells that had been incubated with the 3D10 Construct were IFN-γ⁺.

Thus, in sum, the 1H3 Construct was found to mediate approximately a 7-fold increase in T cell proliferation and approximately a 12 fold increase in IFN-γ production per cell. The cumulative effect of such action is an approximately 100 fold increase in IFN-γ secretion.

As further functional characterization, monocyte-derived DC were matured by incubation with TNFα and PGE2. Cells were then pulsed for 2 hours in the presence of a pool of mixed class I and class II restricted CEF peptides (i.e., peptides of Cytomegalovirus, Epstein-Barr virus and influenza virus), and incubated with CFSE-labeled autologous T cell (LD column, 95% purify) for two weeks. The treated cells were then incubated for two weeks in the presence of CFSE-labeled autologous T cells (LD column, 95% purify) and the above-described antibody constructs. On Day 7, the percentage of CFSE-diluted T cells was found to be 40% for cells incubated with the control antibody, 37% for cells incubated with the 1H3 Construct, 50% for cells incubated with the 3D10 Construct and 57% for cells incubated with antibody CA-18C3 (an anti-IL-1α-specific monoclonal antibody). On Day 11, the percentage of CFSE-diluted T cells was again assessed. The percentage of CFSE-diluted T cells was then found to be 17% for cells incubated with the control antibody and 38% for cells incubated with the 1H3 Construct. The percentage of CFSE-diluted T cells was then found to be 27% for cells incubated with antibody CA-18C3.

The supernatants of the treated cells were also analyzed for IL-2 and IFN-γ cytokines on day 7 (Table 19).

TABLE 19

| Cytokine (pg/ml) | Control Ig | 1H3 Construct | 1E3 Construct | 3H10 Construct |
|---|---|---|---|---|
| IFN-γ | 26816.44 | 39423.11 | 39658.19 | 31954.72 |
| IL-2 | 432.03 | 868.17 | 1182.30 | 1379.07 |

The supernatants of the treated cells were also analyzed for IFN-γ, TNFα and GM-CSF cytokines on day 11. The 1H3 Construct was found to mediate an enhancement of all three cytokines relative to a control antibody (Table 20).

TABLE 20

| Cytokine (pg/ml) | Control Ig | 1H3 Construct | 3H10 Construct |
|---|---|---|---|
| GM-CSF | 52.75 | 150.66 | 70.71 |
| IFN-γ | 223.15 | 786.11 | 228.50 |
| TNF-α | 21.06 | 46.26 | 51.75 |

As further functional characterization, monocyte-derived DC (obtained from HLA-A2 positive donor PBMCs) were matured by exposure to TNFα and PGE2, and the matured DC were then pulsed with HLA-A2 restricted MART-1 and Flu M1 peptides for 2 hours. Afterwards, the cells were incubated for two weeks in the presence of CFSE-labeled autologous T cell (LD column, 95% purify) and the above-described 1H3 Construct or 3D10 Construct. The effect of the MART-1 and M1 peptides on cytokine production is shown in Table 21.

TABLE 21

| Cytokine (pg/ml) | Control Ig | 1H3 Construct | 3H10 Construct |
|---|---|---|---|
| IFN-γ | 0 | 357.64 | 0 |
| IL-17 | 0 | 225.81 | 19.76 |

EXAMPLE 7

Characterization of Humanized Anti-PD-1 Antibodies

The above-described humanized 1H3_var 1-1H3_var 14 antibodies (see Table 17) were evaluated to confirm their ability to bind to human PD-1 and their therapeutic capabilities. Polypeptides encoding the antibodies were expressed in CHO cells and the titers of functional antibodies were determined by ELISA (Table 22).

TABLE 22

| Antibody | Light Chain | Heavy Chain | Antibody Titer (ng/ml) |
|---|---|---|---|
| h1H3 Var 1 | LC1_1 | HC1_1 | 623 |
| h1H3 Var 2 | LC1_1 | HC1_2 | 6520 |
| h1H3 Var 3 | LC1_1 | HC1_3 | 1344 |
| h1H3 Var 4 | LC1_2 | HC1_1 | 1160 |
| h1H3 Var 5 | LC1_2 | HC1_2 | 8840 |
| h1H3 Var 6 | LC1_2 | HC1_3 | 1906 |
| h1H3 Var 7 | LC2_1 | HC2_1 | 35 |
| h1H3 Var 8 | LC2_1 | HC2_2 | 22 |
| h1H3 Var 9 | LC2_1 | HC2_3 | 4 |
| h1H3 Var 10 | LC2_2 | HC2_1 | 232 |
| h1H3 Var 11 | LC2_2 | HC2_2 | 66 |
| h1H3 Var 12 | LC2_2 | HC2_2 | 17 |
| h1H3 Var 13 | LC1_1 | HC2_1 | 219 |
| h1H3 Var 14 | LC2_1 | HC1_1 | 134 |
| 1H3 Parental Control Antibody | — | — | 158 |
| Control | — | — | 11 |

To ensure that binding was specific for human PD-1, binding was assessed using CHO cells that had been transfected to express human PD-1. The results of such binding experiments are shown in FIGS. 18A-18D. By repeating such binding experiments in the presence of 1, 3, 10, 30, 100, 300, 1000 or 3000 ng of the h1H3 variant, it was found that the ability of such humanized antibodies to bind to PD-1 was in all cases dependent upon antibody concentration.

Figure 19A:
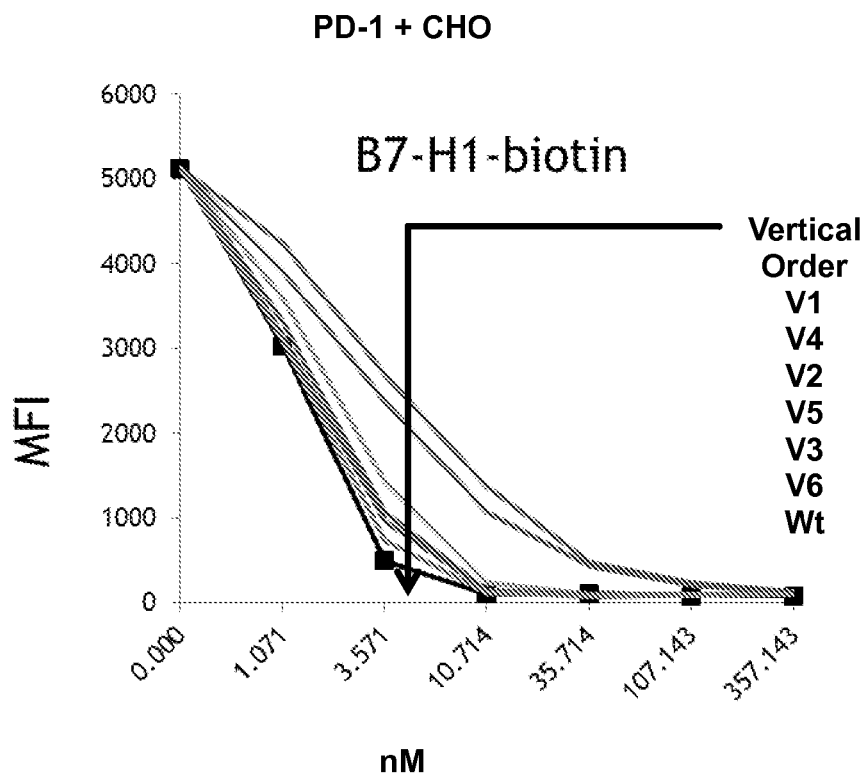
FIGS. 19A-19B demonstrate the ability of humanized anti-PD-1 antibodies to block interactions between hPD-1-Fc and HEK293 cells expressing B7-H1 (FIG. 19A) or B7-DC (FIG. 19B).
Figure 19B:
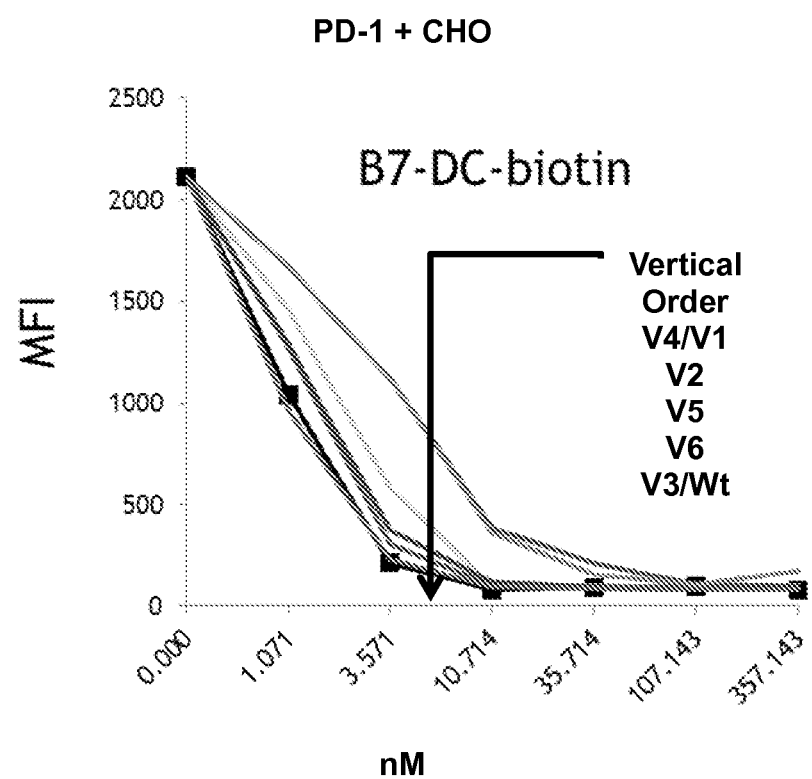

In order to demonstrate the ability of the humanized anti-PD-1 antibodies of the present invention to block interactions between PD-1 and its natural ligands, PD-1-expressing HEK293 cells were incubated in the presence of B7-H1 (or B7-DC) and selected h1H3 variants. The h1H3 variant antibodies were found to be capable of blocking the binding of the B7-H1 to the HEK293 cells (FIG. 19A (B7-H1); FIG. 19B (B7-DC) (Ctl=synagis, WT=chimeric 1H3).

Table 23 provides the results obtained in a 500 ml scale transient expression and purification procedure. Non-reducing gels showed that the expressed antibodies predominantly migrated as a single band of approximately 160 kD; when analyzed in reducing gels, this band was replaced by bands of approximately 60 kD and 30 kD. The results show that Acceptor 1 h1H3 variants: h1H3 Var1, h1H3 Var3, h1H3 Var4 and h1H3 Var6 exhibited good binding to human PD-1 whereas Acceptor 2 h1H3 variants: h1H3 Var7-h1H3 Var14 exhibited poorer binding to human PD-1. Accordingly, the heavy and light chains from Acceptor 1 h1H3 variants: h1H3 Var1-h1H3 Var6 were cloned into the Double Gene Vector (DGV; Lonza Biologics, Berkshire, UK; Bebbington, C. R. et al. (1992) "*High-Level Expression Of A Recombinant Antibody From Myeloma Cells Using A Glutamine Synthetase Gene As An Amplifiable Selectable Marker*," Biotechnology (NY) 10(2): 169-175) and transfected into CHO cells to permit the production of stable antibody-producing cell lines.

TABLE 23

| h1H3 Variant | Concentration (mg/ml) | Volume (ml) | Total (mg) | EU/μg | EC$_{50}$ (nM) |
|---|---|---|---|---|---|
| h1H3 Var 1 | 1.31 | 1.5 | 2.0 | 0.012 * | 6 |
| h1H3 Var 2 | 0.99 | 1.7 | 1.7 | 0.003 | 3 |
| h1H3 Var 3 | 0.61 | 1.6 | 1.0 | 0.005 | 3 |
| h1H3 Var 4 | 1.67 | 1.6 | 2.7 | 0.003 | 6 |
| h1H3 Var 5 | 1.44 | 1.5 | 2.2 | 0.003 | 3 |
| h1H3 Var 6 | 0.69 | 1.6 | 1.1 | 0.008 | 3 |
| Parental | | | | | 3 |

* Commercial very low endotoxin level <0.01 EU/μg

Figure 20:
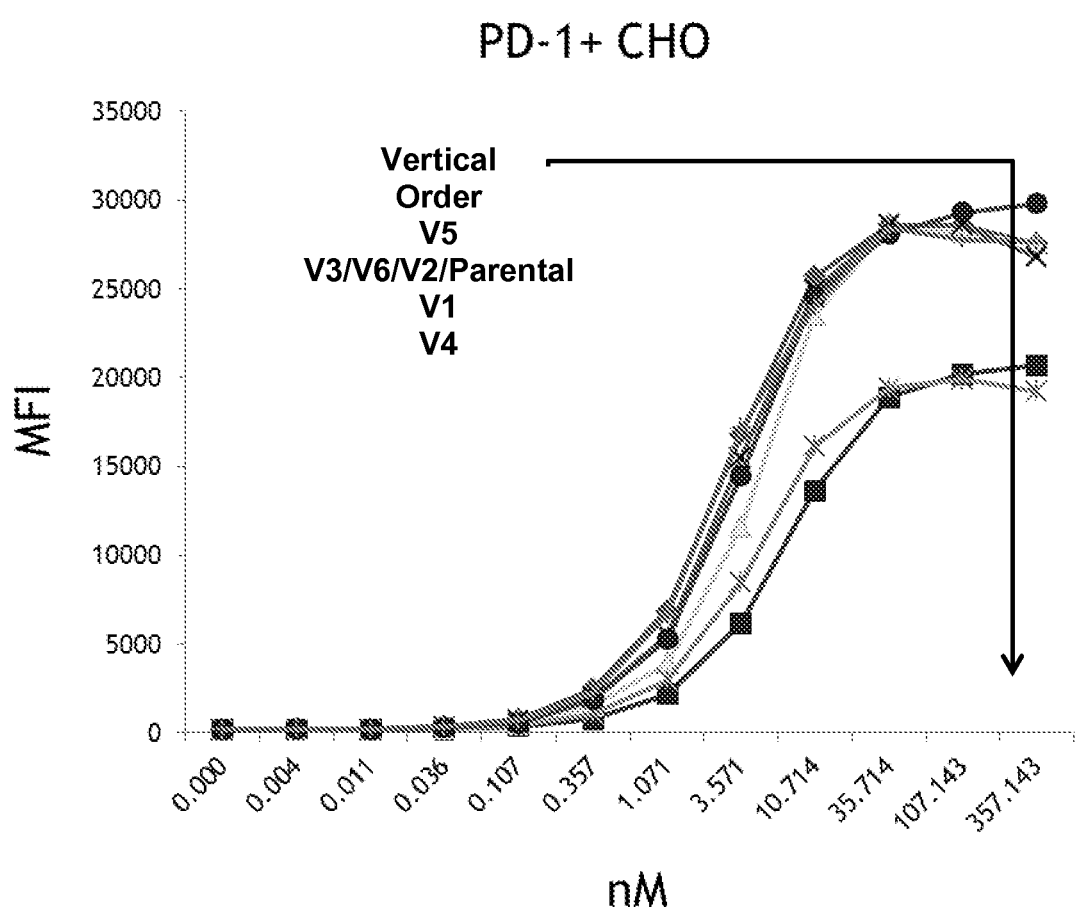
FIG. 20 shows binding curves for h1H3 Var 1-h1H3 Var 6.

Analysis of binding at antibody concentrations of 0.5, 1.5, 5, 15, 50, 150, and 500 ng/ml as well as 1.5, 5, 15, and 50 μg/ml revealed that binding was concentration dependent. The PD-1-specific binding ability of the variants was determined at antibody concentrations ranging from 0 to approximately 350 nM. FIG. 20 shows the resultant curves for h1H3 Var 1-h1H3 Var 6, and indicate that these antibodies bind PD-1. Antibodies h1H3 Var 1 and h1H3 Var 4 exhibit reduced binding relative to the Parental antibody. In contrast, h1H3 Var 2, h1H3 Var 3, h1H3 Var 5 and h1H3 Var 6 exhibited binding that was comparable to that of the Parental antibody. The EC50 data for these antibodies is shown in Table 23.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An antibody or an antigen-binding fragment thereof comprising six complementarity determining regions (CDRs),
   wherein the CDRs comprise the three light chain CDRs of SEQ ID NO:98 and the three heavy chain CDRs of SEQ ID NO:106, and
   wherein the antibody or antigen-binding fragment thereof immunospecifically binds PD-1.

2. The antibody or antigen-binding fragment thereof of claim 1, wherein the immunospecifically bound PD1 is expressed on the surface of a live cell at an endogenous or transfected concentration.

3. The antibody or antigen-binding fragment thereof of claim 1, wherein the PD1 is human PD-1.

4. The antibody or antigen-binding fragment thereof of claim 2, wherein the live cell is a T cell.

5. The antibody or antigen-binding fragment thereof molecule of claim 1, wherein the antibody is a monoclonal antibody, a human antibody, a chimeric antibody or a humanized antibody.

6. The antibody or antigen-binding fragment thereof of claim 5, wherein the antibody is a bispecific, trispecific or multispecific antibody.

7. The antibody or antigen-binding fragment thereof of claim 1, wherein the antibody or antigen-binding fragment thereof is detectably labeled or comprises a conjugated toxin, drug, receptor, enzyme, receptor ligand.

8. The antibody or antigen-binding fragment thereof of claim 1, wherein the antibody or antigen-binding fragment thereof:
   (A) attenuates or blocks the ability of PD1 to bind to a PD1 ligand;
   (B) antagonizes PD1 mediated signal transduction;
   (C) increases T cell proliferation;
   (D) enhances the production of IFN-γ; or
   (E) a combination thereof.

9. A pharmaceutical composition comprising a therapeutically effective amount of the antibody or antigen-binding fragment thereof of claim 8, and a physiologically acceptable carrier or excipient.

10. The antibody or antigen binding fragment thereof of claim 1, wherein the three light chain CDRs comprise a first light chain CDR comprising amino acids 24-33 of SEQ ID NO:98, a second light chain CDR comprising amino acids 49-55 of SEQ ID NO:98, and a third light chain CDR comprising amino acids 88-96 of SEQ ID NO:98.

11. The antibody or antigen binding fragment thereof of claim 1, wherein the three heavy chain CDRs comprise a first heavy chain CDR comprising amino acids 26-35 of SEQ ID NO:106, a second heavy chain CDR comprising amino acids 50-66 of SEQ ID NO: 106, and a third heavy chain CDR comprising amino acids 99-111 of SEQ ID NO: 106.

12. The antibody or antigen binding fragment thereof of claim 1 comprising a light chain variable region comprising the amino acid sequence of SEQ ID NO:98.

13. The antibody or antigen binding fragment thereof of claim 1 comprising a heavy chain variable region comprising the amino acid sequence of SEQ ID NO:106.

14. The antibody or antigen binding fragment thereof of claim 1 comprising a light chain variable region comprising the amino acid sequence of SEQ ID NO:98 and a heavy chain variable region comprising the amino acid sequence of SEQ ID NO:106.

15. The antibody or antigen binding fragment thereof of claim 1 comprising one or more constant domains from an immunoglobulin constant region (Fc).

16. The antibody or antigen binding fragment thereof of claim 15, wherein the constant domains are human constant domains.

17. The antibody or antigen binding fragment thereof of claim 16, wherein the human constant domains are IgA, IgD, IgE, IgG or IgM domains.

18. The antibody or antigen binding fragment thereof of claim 17, wherein human IgG constant domains are IgG1, IgG2, IgG3, or IgG4 domains.

19. A humanized antibody or antigen binding fragment thereof comprising a light chain variable region comprising the amino acid sequence of SEQ ID NO:98, a heavy chain variable region comprising the amino acid sequence of SEQ ID NO:106, or the combination thereof, and one or more human IgG4 constant domains.

20. A method of increasing an immune response in a subject in need thereof comprising administering an effective amount of the pharmaceutical composition of claim 9 to the subject.

21. The method of claim 20, wherein the subject has cancer or an infectious disease.

22. The method of claim 21, wherein the treatment is is provided in advance of any symptom of the cancer, or the infectious disease.

* * * * *